US007893033B2

(12) United States Patent
Hung et al.

(10) Patent No.: US 7,893,033 B2
(45) Date of Patent: Feb. 22, 2011

(54) TARGETING PROTEINS TO DELIVER THERAPEUTIC OR DIAGNOSTIC REAGENTS

(75) Inventors: Mien-Chie Hung, Houston, TX (US); Keng-Li Lan, Houston, TX (US); Keng-Hsin Lan, Taipei (TW); Jaw-Ching Liu, Houston, TX (US); Fu Ou-Yang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/430,503

(22) Filed: May 6, 2003

(65) Prior Publication Data

US 2004/0005684 A1 Jan. 8, 2004

Related U.S. Application Data

(60) Provisional application No. 60/380,063, filed on May 6, 2002.

(51) Int. Cl.
*A61K 48/00* (2006.01)
*C12N 5/09* (2010.01)
*C12N 5/10* (2006.01)

(52) U.S. Cl. ................................. 514/44 R; 424/93.21

(58) Field of Classification Search .................. 514/44, 514/44 R; 435/455, 320.1, 325; 424/93.21
See application file for complete search history.

(56) References Cited

U.S. PATENT DOCUMENTS 5,994,104 A 11/1999 Anderson et al.
6,413,513 B1 7/2002 Holaday et al.
6,537,554 B1 3/2003 Shimkets et al.
6,552,005 B1 * 4/2003 Buchsbaum et al. .......... 514/44
2002/0090374 A1 7/2002 Yarkoni et al.

FOREIGN PATENT DOCUMENTS

WO WO-99/16889 A1 4/1999
WO WO-99/30741 A2 6/1999
WO WO99/16889 * 8/1999 .................... 15/62
WO WO-99/39741 A2 8/1999
WO WO-99/47690 A2 9/1999
WO WO-99/65515 A2 12/1999
WO WO-0011033 3/2000
WO WO-00/71078 A2 11/2000
WO WO-00/74629 A2 12/2000
WO WO-0105826 1/2001
WO WO-0151523 7/2001
WO WO-01/87348 A2 11/2001
WO WO-0244328 6/2002

OTHER PUBLICATIONS

Helfrich et al. (2000) A rapid and versatile method for harnessing scFv antibody fragments with various bilogical effector functions. J. Immun. Meth. 237:131-145.*
Gyorffy et al. (2001) Cobined treatment of a murine Breast Cancer model with type 5 Adenovirus Vectors Expressing Murine Angiostatin and IL-12: Arole for combined Anti-Angiogenesis and Immunotherapy. J. Immun. 166:6212-6217.*
Chen et al. (1999) Liposomes Complexed to Plasmids Encoding Angiostatin and Endostatin Inhibit Breast Cancer in Nude Mice. Cancer Research 59:3308-3312.*
Marshall., Gene Therapy's Growing Pains (1995) Science 269:1050-1055.*
Guhaniyogi et al. (2001) Regulation of mRNA stability in mammalian cells. Gene. 265:11-23.*
Strieter et al. (2002) CXC Chemkines in Angiogenesis Related to Pulmonary Fibrosis. Chest. 122:298S-301S.*
Dickson et al. (2001) Angiogenesis in Acute Chronic Leukemias. Leukemia and Lymphoma 42:847-853.*
Kuo et al. (2001) Comparitive evaluation of the antitumor activity of antiangiogenic proteins delivered by gene transfer. PNAS. 98:4605-4610.*
Orkin et al., Report and Reccommendations of the Panel to assess the NIH invextment in Research on Gene Therapy (1998) 1-41.*
Verma et al., Gene therapy-promises, problems and prospects. (1997) Nature. 389:239-242.*
Claesson-Welsh et al. (1998) Angiostatin induces endothelial cell apoptosis and activation of focal adhesion kinase independently of the integrin-binding motif RGD. PNAS 95:5579-5583.*
Ninck et al. (2003) Expression profiles of angiogenic growth factors in squamous cell carcinomas. In. J. Cancer. 106:34-44.*
Henschke et al. (2005) Surg Oncol Clin N Am. ;14:761-76.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Bowie et al (1990) Science, 247:1306-1310.*
Azar et al. (2000) Apoptosis, vol. 5, 531-542.*
Verma et al. (2001) J. Biol. Chem., vol. 276(7), 4671-4676.*
Niethammer, Andreas G., et al.; Targeted Interleukin 2 Therapy Enhances Protective Immunity Induced by an Autologous Oral DNA Vaccine against Murine Melanoma; Cancer Research 61:6178-6184, Aug. 15, 2001.
Dreier, Torsten, et al.; Recombinant Immunocytokines Targeting the Mouse Transferrin Receptor: Construction and Biological Activities; Bioconjugate Chem. 9:482-489, 1998.

(Continued)

*Primary Examiner*—Anne Marie S Wehbe
(74) *Attorney, Agent, or Firm*—Fulbright & Jaworski, L.L.P.

(57) ABSTRACT

The present invention is directed to compositions comprising an angiogenesis inhibitor coupled to a therapeutic or diagnostic agent. In a specific embodiment, the composition is a fusion gene or fusion gene product encoding the angiogenesis inhibitor coupled to a therapeutic or diagnostic agent. In a particular embodiment, the composition is used for methods to treat angiogenesis-related diseases, such as cancer.

8 Claims, 8 Drawing Sheets

OTHER PUBLICATIONS

Ruehlmann, J. Michael, et al.; MIG (CXCL9) Chemokine Gene Therapy Combines with Antibody-Cytokine. Fusion Protein to Suppress Growth and Dissemination of Murine Colon Carcinoma; Cancer Research 61:8498-8503, Dec. 1, 2001.
Lode, Holger N., et al.; Synergy between an antiangiogenic integrin av antagonist and an antibody—cytokine fusion protein eradicates spontaneous tumor metastases; Proc. Natl. Acad. Sci. USA (Medical Sciences) 96:1591-1596, Feb. 1999.
Penichet, Manuel L., et al.; Antibody—cytokine fusion proteins for the therapy of cancer; Journal of Immunological Methods 248:91-101, 2001.
Kreitman, Robert J.; Immunotoxins in cancer therapy; Current Opinion in Immunology 11:590-578; 1999.
Hotz, Hubert G., et al.; Specific Targeting of Tumor Vasculature by Diphtheria Toxin-Vascular Endothelial Growth Factor Fusion Protein Reduces Angiogenesis and Growth of Pancreatic Cancer; J. Gastrointest Surg 6:159-166, 2002.
Veenendaal, Liesbeth M., et al.; In vitro and in vivo studies of a VEGF121/rGelonin chimeric fusion toxin targeting the neovasculature of solid tumors; PNAS 99(12):7866-7871, Jun. 11, 2002 .
Scappaticci, Frank A., et al.; Statin-AE: A n ovel angiostatin-endostatin fusion protein with enhanced antiangiogenic and antitumor activity; Angiogenesis 4:263-268, 2001.
Camemolla, Barbara, et al.; Enhancement of the antitumor properties of interleukin-2 by its targeted delivery to the tumor blood vessel extracellular matrix; Blood 99:1659-1665, 2002.
Halin, C., et al.; Enhancement of the antitumor activity of interleukin-12 by targeted delivery to neovasculature; Nature Biotechnology 20:264-269, Mar. 2002.
Kirsch, Matthias, et al.; Angiogenesis, metastasis, and endogenous inhibition; Journal of Neuro-Oncology 50:173-180, 2000.
Cao, Yihal; Endogenous angiogenesis inhibitors and their therapeutic implications; The International Journal of Biochemistry & Cell Biology 33:357-369, 2001.
Herbst, Roy S., et al.; Phase I Study of Recombinant Human Endostatin in Patients With Advanced Solid Tumors; J Clin Oncol 20(18):1-12, Sep. 15, 2002.
Eder, Jr., Joseph P., et al.; Phase I Clinical Trial of Recombinant Human Endostatin Administered as a Short Intravenous Infusion Repeated Daily; J Clin Oncol 20(18):1-13, Sep. 15, 2002.
Thomas, James P., et al.; Phase I Pharmacokinetic and Pharmacodynamic Study of Recombinant Human Endostatin in Patients with Advanced Solid Tumors; J Clin Oncol 21(2):223-231, Jan. 15, 2003.
Tarabolette, Giulia, et al.; Antiangiogenic and antivascular therapy for cancer; Current Opinion in Pharmacology 1:378-384, 2001.
Boehm, Thomas, et al.; Antiangiogenic therapy of experimental cancer does not induce acquired drug resistance; Nature 390:404-407, Nov. 1997.
Burke, Patricia A., et al.; Antiangiogenic agents and their promising potential in combined therapy; Critical Reviews in Oncology/Hematology 39:155-171, 2001.
Kerbel, Robert S.; Clinical Trials of Antiangiogenic Drugs: Opportunities, Problems, and Assessment of Initial Results; Journal of Clinical Oncology 19(18s):45s-51s, Sep. 15 Supplement, 2001.
Turner, Richard; Gastric cancer gets the run-around; Nature Medicine 8(5):449, May 2002.
Brem, Steven; Angiogenesis and Cancer Control: From Concept to Therapeutic Trial; Cancer Control 6(5):436-458 1999.
Huang, Xianming, et al.; Tumor Infarctin in Mice by Antibody-Directed Targeting of Tissue Factor to Tumor Vasculature; Science 275:547-550, Jan. 24, 1997.
Molema, Grietje, et al.; The use of bispecific antibodies in tumor cell and tumor vasculature directed immunotherapy; Journal of Controlled Release 64:229-239, 2000.
Lode, Holger N., et al.; Synergy between an antiangiogenic integrin av antagonist and an antibody-cytokine fusion protein eradicates spontaneous tumor metastases; Proc. Natl. Acad. Sci. USA (Medical Sciences)96:1591-1596, Feb. 1999.
Arora, Naveen, et al.; Vascular Endothelial Growth Factor Chimeric Toxin Is Highly Active against Endothelial Cells; Cancer Research 59:183-188, Jan. 1, 1999.
Yang, David J., et al.; Assessment of Antiangiogenic Effect Using 99mTc-EC-Endostatin; Cancer Biotherapy & Radiopharmaceuticals 17(2):233-246, 2002 (date of mailing was May 9, 2002).
Yukihiro, Masashi, et al.; Assessment of angiogenesis using 99mTc-labeled endostatin and angiostatin; Abstract No. 4456, American Association for Cancer Research 2002 Meeting, San Francisco, CA; Abstract available online early Mar. 2002.
Aqueilan, R. S., et al.; Interleukin 2-Bax: A novel prototype of human chimeric proteins for targeted therapy. FEBS Lett, (1999) vol. 457, No. 2, pp. 271-276.
Azar, Y., et al.; GnRH-Bik/Bax/Bak chimeric proteins target and kill adenocarcinoma cells; the general use of pro-apoptotic proteins of the Bcl-2 family as novel killing components of targeting chimeric proteins. Apoptosis (2000) vol. 5, No. 6, pp. 531-542.
Gillies, S.D., et al.; Antibody-IL-12 fusion proteins are effective in SCID mouse models of prostate and colon carcinoma metastases. J. Immunol. (1998), vol. 160, No. 12, pp. 6195-6203.
Lode, H. N., et.al. Immunocytokines: a promising approach to cancer immunotherapy. Pharmacol Ther. (1998), vol. 80, No. 3, pp. 277-292.
Communication of the Patent Office of the State Intellectual Property Office of the People's Republic of China issued Sep. 19, 2008, during the prosecution of Japanese Application No. 03816004.8.
European Patent Office Communication pursuant to Article 94(3) EPC issued Sep. 10, 2008, during the prosecution of EP Patent application No. 03 733 952.0-2404.
Niculescu-Duvaz et al., "Recent developments in gene-directed enzyme prodrug therapy (GDEPT) for cancer", Current Opinion in Molecular Therapeutics, 1999, 480-486, Vo. 1(4).
Sauter, et al., "Adenovirus-mediated gene transfer of endostatin in vivo results in high level of transgene expression and inhibition of tumor growth and metastases", PNAS, 2000, 4802-4807, vol. 97.
Communication pursuant to Article 96(2) EPC issued Sep. 27, 2007 during the prosecution of European Application No. 03 733 952.0-2404.
Supplementary European Search Report re European Application No. 03733952, issued Apr. 26, 2007.
Ou-Yang et al., "Endostatin-Cytosine Deaminase Fusion Protein Suppresses Tumor Growth by Targeting Neovascular Endothelial Cells"; Cancer research; 2006, vol. 66(1), pp. 378-384.
Notice for Reasons for Rejection (Translation) issued Jun. 8, 2009 during the prosecution of Japanese Application No. 2004-501442.

* cited by examiner

TARGETING PROTEINS TO DELIVER THERAPEUTIC OR DIAGNOSTIC REAGENTS

This application claims priority to U.S. Provisional Patent Application 60/380,063, filed May 6, 2002, which is incorporated by reference herein in its entirety.

FIELD OF THE INVENTION

The present invention is directed to the fields of cell biology, molecular biology, cancer biology, and medicine. More particularly, the present invention relates to compositions comprising an angiogenesis inhibitor coupled to a therapeutic or diagnostic agent, and the use of such compositions in therapeutics and cancer therapy.

BACKGROUND OF THE INVENTION

A growing body of evidence reveals that many diseases ranging from age-related macular degeneration, artherosclerosis, rheumatoid arthritis, to cancer are related to angiogenesis, the formation of new blood vessels (Folkman, 2001). Among these angiogenesis-dependent diseases, cancer is the most targeted disease (Brem, 1999; Ferrara and Alitalo, 1999; Keshet and Ben-Sasson, 1999; Carmeliet and Jain, 2000). There are tens of new therapeutic reagents under development based on the theory of antiangiogenesis. In the seminal publication by Folkman, the growth of tumors in both the primary and metastatic sites relies on angiogenesis to support both nutrients and oxygen to tumors (Folkman, 1971). In the following three decades, it has become increasingly convincing that angiogenesis plays a pivotal role in the malignant phenotype. New blood vessel formation has been demonstrated as a critical prognostic factor as well as a therapeutic target in many tumors.

The understanding that tumor growth and metastasis closely relate to the extent of angiogenesis has prompted research laboratories and pharmaceuticals to develop strategies to inhibit angiogenesis, thereby cutting off the blood supply to tumors (Brem, 1999; Ferrara and Alitalo, 1999; Keshet and Ben-Sasson, 1999; Kerbel, 2001; Risau, 1998; Klohs and Hamby, 1999; Rosen, 2000; Burke and DeNardo, 2001; Taraboletti and Margosio, 2001; Glaspy, 2002). Despite the promise of the scientific rationales and scores of experimental drugs being studied in clinical trials, researchers have yet to see significantly positive results from these studies, given the exciting anticancer effects that were demonstrated in the preclinical animal experiments.

Two of the most followed clinical studies involved two endogenous angiogenesis inhibitors, endostatin and angiostatin. These proteins have been shown to be cancer-angiogenesis specific and have no effects on normal blood vessel growth. They have been shown to inhibit cancer growth in animal studies without significant side effects and induction of drug resistance. (Boehm et al., 1997). However, the results from human cancer clinical trials did not match the stunning outcome from the preclinical test (Thomas et al., 2003; Herbst et al., 2002; Eder et al., 2002). Tumor responses in these trials are extremely rare. If there are tumor responses, the rate of the tumor regression is very slow. In some cases, it took more than one year for a patient to see a tumor regress more than 25%. So far, no rapid tumor shrinkage has been demonstrated in clinical trial using these angiogenesis inhibitors. Although tumor responses were not commonly demonstrated in these clinical studies, these endogenous angiogenesis inhibitors did show a very favorable safety profile.

As opposed to the tumor-specific angiogenesis seen in the animal model, tumor-specific blood vessels have been developed for a considerably longer period of time. Therefore, the blood vessels in human tumors are more mature than those in mice tumors. In some embodiments, it will require a longer time of angiogenesis inhibition for these endogenous inhibitors to block the blood flow to tumor to the extent that apoptosis of cancer cells are triggered. These angiogenesis inhibitors exert their function by inhibiting the growth of cancer cells instead of killing the cancer cells. The mechanism of their effect is so called "cytostatic" instead of "cytotoxic". As opposed to cytotoxic reagents such as chemotherapy drugs, these cytostatic angiogenesis inhibitors can not efficiently attack well-established tumor blood vessels often seen in late stage tumor. Thus, these reagents so far did not demonstrate dramatic anticancer effect in clinical trials where most of the patients enrolled are in late stage and exhausted most of the available treatments In contrast to the relatively non-toxic yet less potent anti-angiogenic proteins, described elsewhere herein, various potent therapeutic proteins or polypeptides, and the nucleic acids encoding them, have been used in attempts to treat cancers (not necessarily just kill cancer cells) or were suggested for such use. These include, for example, suicidal proteins, apoptosis-inducing proteins, cytokines, interleukines, TNF family proteins, and nucleic acids encoding them. Specific examples include: GM-CSF, Interferon Alpha, Interferon beta, Interferon gamma, Interleukin-1 Beta, Interleukin-2, Interleukin-4, Interleukin-5, Interleukin-6, Interleukin-8, Interleukin-10, Interleukin-12, Interleukin-13, Interleukin-14, Interleukin-16, Interleukin-18, Interleukin-23, Interleukin-24, Tumor Necrosis Factor SuperFamily member 14, Tumor Necrosis Factor SuperFamily member 13B, Tumor Necrosis Factor Alpha, Tumor Necrosis Factor SuperFamily member 12, Intercellular Adhesion Molecule-1, Lymphocyte Function-Associated antigen-3, Co-Stimulatory Molecule B7-1, Co-Stimulatory Molecule B7-2, FMS-related tyrosine kinase 3 ligand, CD40 Ligand, Surface antigen CD70, T-cell activation cell surface glycoprotein ligand, Co-Stimulatory Molecule OX-40 ligand, TNF-related activation-induced cytokine, Tumor Necrosis Factor SuperFamily member 11, TNF-related activation-induced cytokine, Tumor Necrosis Factor SuperFamily member 11, Cytosine deaminase, HSV Thymidine Kinase, Fas ligand, Caspase 3, TGF-$\alpha$1, TGF-$\alpha$2, TRAIL, Bax, Bak, Bik, Bok, Noxa, a Bcl-2 family protein, Granulysin (NKG5), Granzyme A, Granzyme B, and Perforin.

For example, IL2 and Interferon-$\alpha$ (Glaspy, 2002) have been used in the treatment for renal cell carcinoma and melanoma. However, significant systemic toxicity is usually seen in the cancer patients, thereby limiting the increase of dose and their clinical effects. IL12 has demonstrated potent and broad anticancer effects (Trinchieri, 2003). However, unacceptable side effects have manifested in some clinical trials (Leonard et al., 1997), which hamper its promise as an anticancer reagent.

To minimize the systemic side effects of cytokines, such as interleukin, as well as those therapeutic proteins listed in Table 1, many proteins have been used to target these otherwise considerably toxic therapeutic proteins to tumor-specific blood vessel. In addition, small molecules have been also utilized for tumor imaging while coupled to proteins specific for targeting tumor angiogenic blood vessels. Some of these approaches are summarized in Table 1.

TABLE 1

| Targeting Tool | Therapeutic/ Diagnostic Agent | Comments |
|---|---|---|
| Endostatin (Yang et al., 2002) | 99mTc | Small molecule 99mTC was used as imaging molecule. The inventors used proteins as fused molecule, which could be utilized in gene therapy without having to purify proteins. |
| antibody fragment specific to ED-B domain of fibronectin (Halin et al, 2002) | IL-12 | The targeting antibody fragment is specific to one of angiogenesis markers, ED-B domain of fibronectin. However, it does not possess antiangiogenic activity. |
| antibody fragment specific to ED-B domain of fibronectin (Carnemolla et al., 2002) | IL-2 | Similar approach as (Hahn et al., 2002) |
| angiostatin-endostatin (Scappaticci et al., 2001) | Angiostatin-Endostatin | Two antiangiogenic proteins were fused together and demonstrated better antiangiogenic effect than single molecule. ThE new fusion protein still cytostatic, but not cytotoxic. |
| VEGF (Veenendaal et al., 2002; Arora et al., 1999; Hotz et al., 2002) | Gelonin diphtheria (Veenendaal et al., 2002) Toxin (Arora et al., 1999; Hotz et al., 2002) | VEGF is specific to VEGF receptors, which are expressed abundantly in tumor vasculatures. It can trigger the angiogenic pathway. VEGF is not an antiangiogenic protein. |
| antibody B21-2 to target I-$A^d$, a marker of tumor specific blood vessel (Huang et al., 1997) | truncated form of tissue factor (tTF) | This approach again uses an antibody specific for tumor blood vessel as targeting tool without intrinsic antiangiogenic property. tTF induces thrombosis, thereby blocking blood flow. |

Additional targeting strategies have involved the preparation of immunotoxins (Kreitman, 1999) by coupling antibodies specific to markers of tumor (CD20 of B-cell lymphoma, Her-2/neu of breast cancers, EGFR of colon, head and neck etc.) or tumor-specific blood vessels (ED-B domain of fibronectin, integrin $\alpha v\beta 3$, VEGF receptors, etc.) to therapeutic reagents, such as interleukins, cytokines, gelonin, diphtheria toxin, radio-isotopes, etc. However, most of the immunotoxin strategies have yet to enjoy clinical success, except very few have been approved, such as Zevalin™ (ibritumomab tiuxetan) (IDEC Pharmaceuticals; San Diego, Calif.) and Baxxar (Corixa; Seattle, Wash.).

WO 99/16889 describes fusion proteins having an angiostatin amino acid sequence linked to a second moiety having different or complementary activity. In particular embodiments, the second moiety is selected from endostatin, human type I interferon, thrombospondin, interferon-inducible protein 10 (IP-10) and platelet factor 4. In other particular embodiments, the fusion proteins are used for anti-tumor treatment.

In view of the above, there is a need for compositions and methods that overcome the problems in the art and allow for the treatment of angiogenesis-dependent diseases.

BRIEF SUMMARY OF THE INVENTION

The current invention overcomes the problems listed above and results in compounds and therapies that allow for the diagnosis and treatment of angiogenesis-dependent diseases.

In the context of the invention, angiogenesis inhibitors are coupled to therapeutic or diagnostic agents. In many embodiments, the angiogenesis inhibitors are anti-angiogenesis proteins or polypeptides. Given their affinities to new cancer blood vessels, but not to normal blood vessels, these protein and polypeptides can be used as targeting proteins to deliver therapeutic or diagnostic reagents to the vicinity of diseased cells and/or tissues.

Therapeutic proteins/reagents linked to angiogenesis inhibitors have significantly enhanced therapeutic effects, as compared with angiogenesis inhibitors or therapeutic proteins/reagents used alone. Using angiogenesis inhibitors as a delivery (home-in) protein or agent brings the therapeutic reagents to the vicinity of cancer cells and/or tissues, because the angiogenesis inhibitors associate with and/or bind with angiogenesis-specific disease-specific blood vessels. The therapeutic effects of these therapeutic agents are enhanced as a result of the increased local concentrations.

In addition, angiogenesis inhibitors may also be coupled to diagnostic reagents. For example, they may be coupled to green fluorescent proteins, luciferase, radioisotopes, or combinations thereof. These angiogenesis inhibitor-diagnostic reagent conjugates will facilitate diagnosis of patients.

In broad embodiments, the invention related to compositions comprising an angiogenesis inhibitor coupled to a therapeutic or diagnostic agent. Some preferred aspects of the invention related to fusion proteins comprising an antiangiogenesis polypeptide region linked to a therapeutic protein or polypeptide region or a diagnostic protein or polypeptide region and to nucleic acids encoding such fusion proteins. However, in other embodiments, an angiogenesis inhibitor can be chemically cross-linked to a therapeutic or diagnostic agent.

Those of ordinary skill will understand, in view of this specification that any antiangiogenesis protein currently know, or in the future discocere, that allows for the aims of the invention to be achieved, will be of use in the contents of the invention. Specific antiangiogenesis proteins or polypeptides employed in the context of the invention are discussed in greater detail in other portions of this specification. Some specific examples, which are presently preferred, include endostatin, tumstatin, angiostatin, and a soluble portion of VEGF Receptor 2.

Therapeutic agents useful in the context of the invention will be well understood by those of skill in the art in view of this specification. In some cases, the therapeutic agent is a therapeutic protein or polypeptide. However small molecules, chemotherapeutic drugs, toxins, radioactive compounds, and any other form of therapeutic agent that may be employed in the invention to achieve a therapeutic benefit are also within the scope of the invention.

As described in greater detail in other portions of this specification, exemplary therapeutic proteins and polypeptides of the invention include, but are in no way limited to, those of the classes of suicidal proteins, apoptosis-inducing proteins, cytokines, interleukins, and TNF family proteins. Exemplary diagnostic proteins or peptides, include for example, a green fluorescent protein and luciferase. The above are only examples of therapeutic proteins that might be fused with an antiangiogenic sequence. One skilled in the art would appreciate that other therapeutic and diagnostic proteins may be used.

In some preferred embodiments of the invention, the angiogenesis inhibitor is an antiangiogenesis polypeptide, such as described elsewhere in this specification. Some preferred embodiments involve endostatin, tumstatin, angiostatin, or a soluble VEGF Receptor 2, as the antiangiogenesis polypeptide. Some preferred therapeutic embodiments of the invention involve, as a therapeutic protein or polypeptide, an interleukin protein or polypeptide, such as, for example, an interleukin-12, a suicide protein, such as, for example, a cytosine deaminase, or an apoptosis-inducing protein, such as, for example, a native or mutant bik protein. Some preferred diagnostic embodiments of the invention involve, as a diagnostic protein or polypeptide, a green flouresncent protein or luciferase. Some specifically preferred therapeutic embodiments include: endostatin/interleukin-12, angiostatin/interleukin-12, tumstatin/interleukin-12, soluble VEGF Receptor 2/interleukin-12, endostatin/cytosine deaminase, angiostatin/cytosine deaminase, tumstatin/cytosine deaminase, soluble VEGF Receptor 2/cytosine deaminase, endostatin/mutant bik, angiostatin/mutant bik, tumstatin/mutant bik, and soluble VEGF Receptor 2/mutant bik. While some specifically preferred diagnostic embodiments include: endostatin/green flourescent protein, angiostatin/green flourescent protein, tumstatin/green flourescent protein, soluble VEGF Receptor 2/green flourescent protein, endostatin/luciferase, angiostatin/luciferase, tumstatin/luciferase, and soluble VEGF Receptor 2/luciferase.

While the simplest embodiments of the invention relate to one angiogenesis inhibitor coupled to one therapeutic or diagnostic agent, there is no reason why more elaborated compositions may not be constructed according to the invention. For example, it is possible to couple two or more angiogenesis inhibitors to a single therapeutic or diagnostic agent, a single angiogenesis inhibitor to two or more therapeutic or diagnostic agents; or even two or more angiogenesis inhibitors to two or more therapeutic or diagnostic agents. In some cases, multiple angiogenesis inhibitors, therapeutic agents, and/or diagnostic agents coupled in the context of the invention will be the same, for example two endostatin polypeptides coupled to a single interleukin-12 polypeptide. Alternatively, multiple angiogenesis inhibitors, therapeutic agents, and/or diagnostic agents coupled in the context of the invention will be the same, for example one endostatin polypeptide coupled to an interleukin-12 polypeptide and a cytosine deaminase polypeptide. Those of skill will be able to follow the teachings of the specification to make any such embodiments of the invention.

In embodiments of the invention relating to fusion proteins, those skilled in the art would appreciate that, typically, the fusion proteins will be expressed from a nucleic acid sequence encoding an antiangiogenesis polypeptide region linked to a therapeutic protein or polypeptide region or a diagnostic protein or polypeptide region. In such nucleic acids, it is possible that the nucleic acid sequence encoding an antiangiogenesis polypeptide region could be placed at either the 5' or the 3' end of the nucleic acid sequence encoding the therapeutic protein or polypeptide region or a diagnostic protein or polypeptide region. Furthermore, the invention is not restricted in regard to how nucleic acids encoding these fusion proteins should be constructed into an expression vector. The antiangiogenic nucleic acid and the therapeutic or diagnostic nucleic acid may be constructed into a vector in separate construction steps. Alternatively, they may be first fused, then constructed into an expression vector. The invention also relates to nucleic acids encoding a fusion protein comprising an antiangiogenesis polypeptide region linked to a therapeutic protein or polypeptide region or a diagnostic protein or polypeptide region. Such nucleic acids may be comprised in a vector, complexed with a lipid, and/or comprised in a pharmaceutically acceptable excipient.

Some specific embodiments of the invention relating to methods of making fusion proteins and nucleic acids encoding such fusion proteins comprise: obtaining a first nucleic acid encoding a fusion protein comprising an antiangiogenesis polypeptide region or complement thereof; obtaining a second nucleic acid encoding a therapeutic protein or polypeptide region or a diagnostic protein or polypeptide region or complement thereof; and using the first nucleic acid and the second nucleic acid to create a nucleic acid encoding a fusion protein comprising an antiangiogenesis polypeptide region linked to a therapeutic protein or polypeptide region or a diagnostic protein or polypeptide region. These methods may further comprise testing the nucleic acid encoding the fusion protein for an ability to, under appropriate conditions, express the fusion protein and/or for diagnostic or therapeutic activity. Such methods may also, further comprise administering the nucleic acid encoding the fusion protein to a subject.

In addition to using a fusion protein approach, the therapeutic or diagnostic proteins or small molecule reagents may be cross-linked to an antiangiogenic protein, polypeptide, or peptide using chemical cross-linking reagents. One skilled in the art would know that various cross-linking reagents that are specific for certain amino acid side chains are available from commercial sources. The choice of a particular cross-linking reagent would depend on the proteins (or small molecule therapeutic or diagnostic agents) involved.

With a chemical cross-linking approach, one could practice a method comprising: obtaining an angiogenesis inhibitor; obtaining a therapeutic or diagnostic agent; chemically cross-linking the angiogenesis inhibitor to the therapeutic or diagnostic agent to create an angiogenesis inhibitor coupled to the therapeutic or diagnostic agent. Such a method might further comprise testing the angiogenesis inhibitor coupled to the therapeutic or diagnostic agent for diagnostic or therapeutic activity and/or administering the angiogenesis inhibitor coupled to the therapeutic or diagnostic agent to a subject. In an exemplary embodiment, one could express the antiangiogenic gene product, cross link it with the desired molecule (therapeutic or diagnostic), purify the cross-linked product, and administer the product to patients (such as, for example, for therapeutic purposes or a diagnostic purpose, or both) or to laboratory animals (for research purpose).

Some aspects of the invention relate to methods comprising treating a cell with a composition comprising an angiogenesis inhibitor coupled to a therapeutic or diagnostic agent. The cell may be comprised in a subject, or in the alternative, in cell culture. In some embodiments, the cell is comprised in a test subject, such as a mouse. In other embodiments, the subject is a human.

Preferred aspects of the invention related to methods of treating or diagnosing an angiogenesis-dependent disease, for example, but not limited to cancer, age-related macular degeneration, artherosclerosis, angiofibroma, neovascular glaucoma, arteriovenous malformations, nonunion fractures, arthritis, rheumatoid arthritis, lupus, connective tissue, disorders, Osler-Weber syndrome, psoriasis, corneal graft neovascularization, pyogenic granuloma, delayed wound healing, retrolental fibroplasia, diabetic retinopathy, scleroderma, granulations, hemangioma, trachoma, hemophilic joints, vascular adhesions, hypertrophic scars, multiple sclerosis, restenosis, and obesity. Those of skill in the art will, in the context of the invention, understand the definition of "angiogenesis-dependent disease." Some particular embodiments relate to the treatment of cancer, for example, but not limited to the cancer is head and neck cancer, ovarian cancer, thyroid cancer, oral cancer, prostate cancer, melanoma, colon cancer, breast cancer, angioma, sarcoma, lung cancer, brain cancer, pancreatic cancer, liver cancer, bladder cancer, gastrointestinal cancer, leukemia, lymphoma, and myeloma. Some embodiments of these methods comprise administering to a subject an angiogenesis inhibitor coupled to a therapeutic or diagnostic agent, for example, but not limited to, a fusion protein, comprised in pharmacologically acceptable excipient. Other embodiments, comprise administering to the subject a nucleic acid encoding a fusion protein comprising an antiangiogenesis polypeptide region linked to a therapeutic protein or polypeptide region or a diagnostic protein or polypeptide region. In such cases, nucleic acid may comprised in a plasmid, a retroviral vector, an adenoviral vector, an adeno-associated viral vector, or associated with a lipid. Further, the nucleic acid may be dispersed in a pharmacologically acceptable excipient.

Specific aspects of the invention relate to methods of treating or diagnosing cancer comprising: obtaining a fusion protein comprising an antiangiogenesis polypeptide region linked to a therapeutic protein or polypeptide region or a diagnostic protein or polypeptide region or a nucleic acid encoding a fusion protein comprising an antiangiogenesis polypeptide region linked to a therapeutic protein or polypeptide region or a diagnostic protein or polypeptide region; and administering the fusion protein or nucleic acid encoding the fusion protein to a patient.

Other specific aspects of the invention relate to diagnostic and/or therapeutic kits that comprise a composition, fusion protein, or nucleic acid encoding a fusion protein of the invention in an appropriate container.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1A demonstrates anti-endostatin antibody Western blot of supernatants collected from 293 cells (18 KD endostatin(□), 58 KD endostatin-CD (◀), and 93 KD endo-IL12(←)). In FIG. 1B, an ELISA kit (specific for endostatin) was utilized.

In FIGS. 2A through 2C, HUVEC cell tube formation was studied, and in FIGS. 2E through 2G, cell migration was studied. In FIGS. 2D and 2H, five fields were viewed; and the respective tubes or migrated cells were counted and averaged.

FIGS. 3A and 3B show an MTT assay. FIG. 3C shows green fluorescent protein expression in 293T cells transfected with Endo-GFP fusion gene. In FIG. 3D, the cell proliferation of NSF60 was studied for stimulation by conditional medium from COS-7 transfected by Endostatin-GM-CSF plasmid.

FIG. 5A provides GFP detection in an experimental group utilizing tumor of B-16 endostatin-GFP stable cell lines. FIG. 5B provides GFP detection in contra-lateral tumor to A (from B-16 parental cell lines) in blood vessel wall (◀). FIG. 5C shows GFP detection in tumors from bilateral B-16 parental cell lines in a control group.

FIG. 7A provides intratumoral gene therapy against B16F10 tumor. FIG. 7B shows similar intratumoral gene therapy as in FIG. 7A against B16F10 tumor, except original distant tumor was challenged at $2\times10^5$ cell. FIG. 7C provides illustration comparing endo-IL12 versus IL12 and endostatin alone.

FIG. 8A shows ex vivo treatment of endostatin-CD fusion gene of antiangio-chemotherapy (Endo: endostatin; CD: cytosine deaminase; Endo-CD: fusion gene). FIG. 8B shows that ex vivo treatment of Tum5-IL12 fusion gene of antiangio-immunotherapy showed better tumor inhibitory effect on distant tumor (Tum5: tumstatin antiangiogenic deletion mutant, IL12: interleukin-12, Tum5-IL12: fusion gene). FIG. 8C illustrates distant CT26 colon cancer growths in the presence of the fusion genes. Various genes were injected into CT26 tumor sites distant from the measured tumors, which were not treated with direct injection of genes. In FIG. 8D stable line treatment of endostatin-IL12 against distant tumor is provided.

DETAILED DESCRIPTION OF THE INVENTION

Definitions

Figure 1:
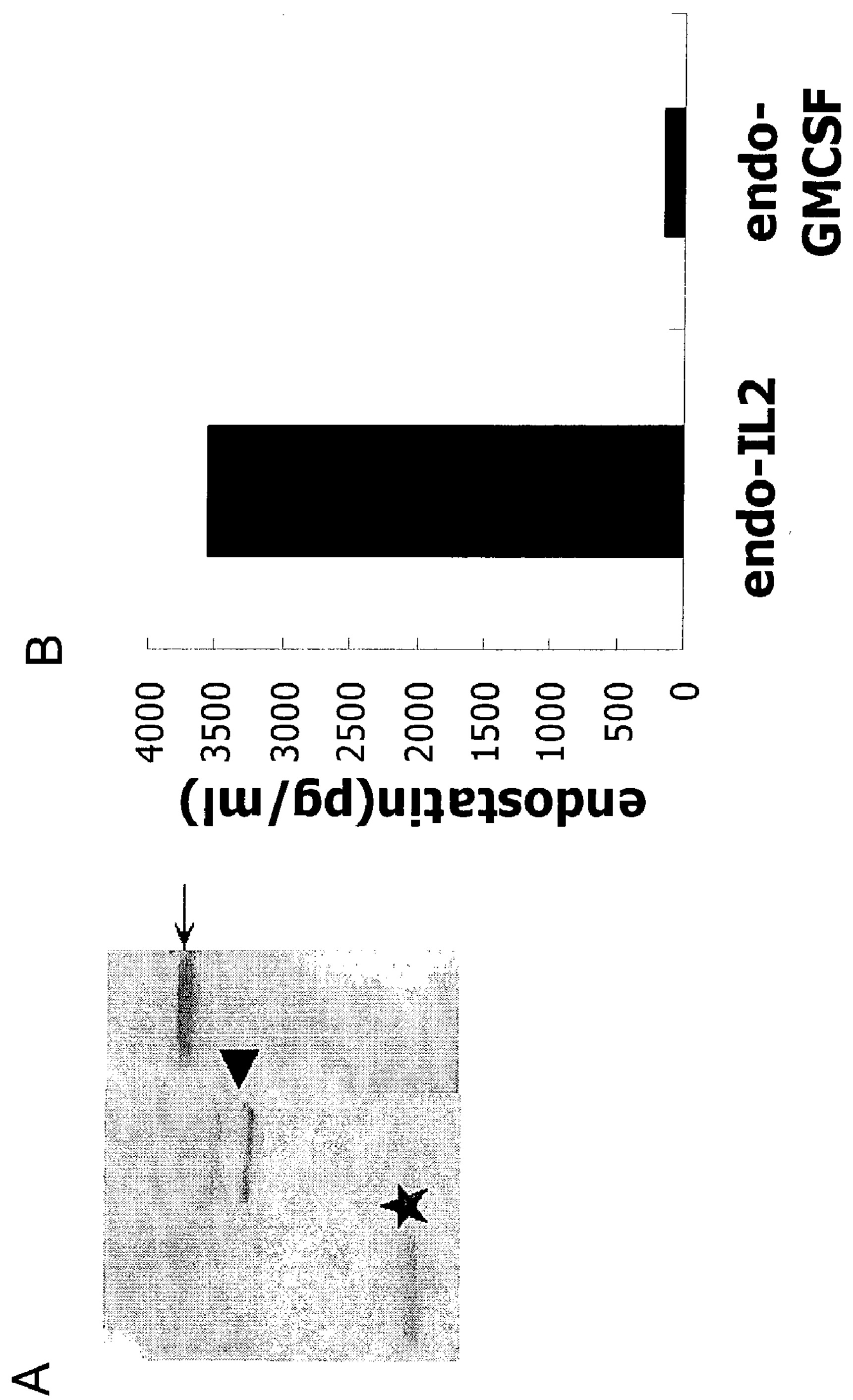
FIGS. 1A and 1B show that antiangiogenic-therapeutic/diagnostic fusion protein could be detected.

As used herein the specification, "a" or "an" may mean one or more. As used herein in the claim(s), when used in conjunction with the word "comprising", the words "a" or "an" may mean one or more than one. As used herein "another" may mean at least a second or more.

The term "therapeutically effective" as used herein refers to the amount of a compound required to improve some symptom associated with a disease. For example, in the treatment of cancer, a compound that improves the cancer to any degree or arrests any symptom of the cancer would be therapeutically effective. For example, the improvement of the cancer may be inhibition of angiogenesis of a cancer cell and/or tissue, inhibition or retardation of cell growth, facilitation of cell death, or a combination thereof. A therapeutically effective amount of a compound is not required to cure a disease but will provide a treatment for a disease.

This application incorporates by reference herein in its entirety PCT International Application WO 99/16889.

The Present Invention

To provide useful compositions and methods for use in the art of cancer therapy, the inventors exploit endogenous angiogenesis inhibitors, which are tumor vessel-specific. In exemplary embodiments, the inventors construct an angiogenesis inhibitor coupled to a therapeutic or diagnostic agent. In some exemplary embodiments, the angiogenesis inhibitor coupled to a therapeutic or diagnostic agent is a fusion of two components: the antiangiogenic component and the therapeutic (or diagnostic) component. In a specific embodiment, the angiogenesis inhibitor coupled to a therapeutic or diagnostic agent is a fusion gene that encodes a fusion protein comprising the two protein components. Thus, the fusion genes may be generated by connecting coding sequences of both antiangiogenic and therapeutic (or diagnostic) protein, thereby transforming cytostatic antiangiogenic proteins into cytotoxic fusion proteins. In addition, antiangiogenic protein could be also fused with diagnostic proteins, such as green fluorescent protein and luciferase, which could be led by antiangiogenic protein to tumor-specific blood vessels. In the alternative embodiment, the antiangiogenic protein component and the therapeutic or diagnostic protein component are chemically linked by standard means in the art. In exemplary embodiments, fusion gene constructs are generated by fusing the nucleic acid encoding at least one antiangiogenic protein with at least one therapeutic or diagnostic nucleic acid.

Given the affinities of angiogenesis inhibitors to newly formed cancer blood vessels, but not to normal blood vessels, these proteins are used as targeting proteins to deliver therapeutic reagents to the vicinity of cancer cells without expansion of toxicity. Therapeutic proteins/reagents linked to these angiogenesis inhibitor will have significantly enhanced cancer killing and anti-cancer effects as compared with angiogenesis inhibitor or the therapeutic proteins/reagents used alone.

Antiangiogenic Proteins

Any antioangiogenic protein, polypeptide, or peptide may be utilized for the angiogenesis inhibitor coupled to a therapeutic or diagnostic agent, such as the exemplary targeting fusion gene products of the present invention. Angiogenic inhibitors (also referred to as antiangiogenic compounds) are those that inhibit, reduce, halt, retard, impede, prevent, deter, slow down, reverse, or hinder angiogenesis. In a specific embodiment, the angiogenesis in a tissue imparts deleterious effects on the tissue in which the blood vessels are generating, such as to a tumor or a retina.

Exemplary embodiments include Angiopoietin-2, Angiostatin, AntiThrombin III (AT3), Amino-terminal fragment of Urokinase, Calreticulin, Endostatin, VEGF Receptor 2 (soluble fragment) (prepared by removal of a transmembrane region), VEGF Receptor 1 (soluble fragment) (prepared by removal of a transmembrane region), Interferon-alpha Inducible Protein 10, the 5 Kringle domains of plasminogen, Kringle-5 domain of plasminogen, Mammary serine protease inhibitor, Monokine-induced by Interferon-gamma, Angiostatic chemokines Fusion Gene, Pigment Epithelium-Derived Factor, C-term hemopexin domain of MMP-2, Platelet Factor 4 (CXCL4), Proliferin-Related Protein, Endothelium-specific receptor tyrosine kinase, Tissue inhibitor of metalloproteinase-1, Tissue inhibitor of metalloproteinase-2, Tissue inhibitor of metalloproteinase-3, Tissue inhibitor of metalloproteinase-4, Troponin I-2 (fast-twitch skeletal muscle), Ser94-Gln471 fragment of Tryptophanyl-tRNA synthetase, Thrombospondin, Tumstatin, or a combination thereof. A skilled artisan recognizes how to obtain the sequences for these proteins, polypeptides, or peptides, and the nucleic acid sequences that encode them, by accessing their publically available sequences in the GenBank database provided by the National Center for Biotechnology Information, using well-known means in the art. Exemplary embodiments of antiangiogenic sequences include (accompanied, where appropriate, with their GenBank sequence): endostatin (AF333247; SEQ ID NO:37); angiostatin (SEQ ID NO:38); tumstatin (AF258351; SEQ ID NO:39) and thrombospondin (M81339; SEQ ID NO:40).

Any of these antiangiogenic nucleic acids, as well as others in the art or identified at a later date and not listed herein, could be delivered as a component of gene therapy reagents against cancer or angiogenesis-dependent diseases as fusions with a therapeutic and/or diagnostic protein, as listed herein or as is well known in the art or that may be identified at a later date. Alternatively, fusion proteins encoded by these fusion nucleic acids, and those not listed herein, could be expressed and purified for protein therapy targeting cancer and other angiogenesis-dependent diseases.

A skilled artisan recognizes that, in some embodiments, an antiangiogenic sequence may provide therapy for the disease and/or may provide diagnostic capability for the disease.

Therapeutic/Diagnostic Proteins

Many compositions of the present invention comprise a therapeutic or diagnostic protein or polypeptide, or nucleic acids encoding therefore. Any such therapeutic or diagnostic protein or polypeptide, or nucleic acid encoding such may be used in the present invention, whether presently know to those of skill or discovered after the filing of this application.

One skilled in the art is aware of a variety of therapeutic proteins or polypeptides, and the nucleic acids encoding them that will be beneficial for the treatment of angiogenesis-dependent diseases, including cancer therapy. In specific embodiments, such therapeutic proteins or polypeptides may can include, but not be limited to, suicide proteins, toxin proteins, pro-apoptotic proteins, cytokine proteins, and/or anti-angiogenic proteins.

In specific methods and compositions of the present invention, the therapeutic polypeptide or protein is a "suicide protein" that causes cell death by itself or in the presence of other compounds. A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, β-glucuronidase, penicillin-V-amidase, penicillin-G-amidase, β-lactamase, nitroreductase, carboxypeptidase A, linamarase (also referred to as β-glucosidase), the *E. coli* gpt gene, and the *E. coli* Deo gene, although others are known in the art. In some embodiments, the suicide protein converts a prodrug into a toxic compound. As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-β-D-arabinofuranosyl)-5-iodouracil) for thymidine kinase; ifosfamide for oxidoreductase; 6-methoxypurine arabinoside for VZV-TK; 5-fluorocytosine for cytosine deaminase; doxorubicin for β-glucuronidase; CB1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug. In specific embodiments, the prodrug is administered in a dose of from about 1-20 mg/day/kg body weight, from about 1-50 mg/day/kg body weight, or about 1-100 mg/day/kg body weight.

In some embodiments, a therapeutic protein or polypeptide, is a cancer suppressor, for example p53 or Rb, or a nucleic acid encoding such a protein or polypeptide. Of course, those of skill know of a wide variety of such cancer suppressors and how to obtain them and/or the nucleic acids encoding them.

Other examples of therapeutic proteins or polypeptides include pro-apoptotic therapeutic proteins and polypeptides, for example, p15, p16, or $p21^{WAF-1}$. One specific embodiment, involves pro-apotoptic proteins or polypeptides which are wild-type Bik or mutant Bik comprising similar or greater activity compared to wild-type Bik. In some specific embodiments further specific embodiment, the Bik mutant comprises a substitution at $Thr^{33}$, $Ser^{35}$, or both $Thr^{33}$and $Ser^{35}$. In an additional specific embodiment, the substitution is with Asp. U.S. Provisional Patent Application No. 60/459,901, filed Apr. 2, 2003, which is incorporated by reference herein in its entirety, describes Bik, mutant Biks, and nucleic acid sequences encoding them.

Cytokines, and nucleic acid encoding them may also be used as therapeutic proteins and polypeptided. Examples include: GM-CSF (granulocyte macrophage colony stimulating factor); TNFα (Tumor necrosis factor α); Interferons including, but not limited to, IFN α and IFN γ; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24), although other embodiments are known in the art.

An exemplary, but not limiting or comprehensive list of therapeutic proteins or polypeptides includes (followed in some cases by the a GenBank Accession No. for a nucleic acid encoding them): Herpes simplex virus type 1 (mutant KG111) thymidine kinase (SEQ ID NO:1; J04327); Herpes simplex virus type 2 (strain 9637) thymidine kinase (tk) (SEQ ID NO:2; M29941); Varicella zoster thymidine kinase (SEQ ID NO:3; M36160); *Escherichia coli* cytosine deaminase (SEQ ID NO:4; S56903); p450 oxidoreductase (SEQ ID NO:5; D17571); carboxypeptidase G2 (SEQ ID NO:6; M12599); β-glucuronidase (SEQ ID NO:7; M15182); penicillin-V-amidase (SEQ ID NO:8; M15660); penicillin-G-amidase (SEQ ID NO:9; AF161313); β-lactamase (SEQ ID NO:10; AY029068); nitroreductase (SEQ ID NO:11; A23284); carboxypeptidase A (SEQ ID NO:12; M27717); linamarase (SEQ ID NO:13; S35175); *E.coli* gpt (SEQ ID NO:14; X00221); *E. coli* Deo (SEQ ID NO:15; X03224); p53 (SEQ ID NO:16; AF307851); Rb (SEQ ID NO:17; XM_053409); p15 (SEQ ID NO:18; U19796); p16 [(SEQ ID NO:19; U12818) (SEQ ID NO:20; U12819) and (SEQ ID NO:21; U12820)]; $p21^{WAF-1}$ (SEQ ID NO:22; AF497972); GM-CSF (SEQ ID NO:23; M10663); TNF α (SEQ ID NO:24; AY066019); IFN α (SEQ ID NO:25; M34913); IFN α (SEQ ID NO:26; J00219); Interferon gamma; Interferon beta; IL1 (SEQ ID NO:27; M28983); IL-beta; IL2 (SEQ ID NO:28; K02056); IL3 (SEQ ID NO:29; M14743); IL4 (SEQ ID NO:30; M23442); IL5; IL6 (SEQ ID NO:31; M29150); IL7 (SEQ ID NO:32; J04156); IL8; IL10 (SEQ ID NO:33; U16720); IL12A (SEQ ID NO:34; NM_000882); IL12B (SEQ ID NO:35; NM_002187); IL13; IL14; IL15 (SEQ ID NO:36; U14407); IL16; IL18; IL23; IL24; Tumor Necrosis Factor SuperFamily member 14; Tumor Necrosis Factor SuperFamily member 13B (also called BlyS, BAFF, THANK); soluble form; Tumor Necrosis Factor Alpha; Tumor Necrosis Factor SuperFamily member 12 (also called Apo3L); Intercellular Adhesion Molecule-1; Lymphocyte Function-Associated antigen-3; Co-Stimulatory Molecule B7-1; Co-Stimulatory Molecule B7-2; FMS-related tyrosine kinase 3 ligand; CD40 Ligand; Surface antigen CD70; T-cell activation cell surface glycoprotein ligand; Co-Stimulatory Molecule OX-40 ligand (formerly gp34); TNF-related activation-induced cytokine; full-length (isoform 1, ODF; RANKL). Tumor Necrosis Factor SuperFamily member 11; TNF-related activation-induced cytokine; soluble form (isoform 2, sODF, sRANKL). Tumor Necrosis Factor SuperFamily member 11; Granulysin (NKG5); Granzyme A; Granzyme B; and Perforin.

Examples of diagnostic proteins include Green fluorescent protein (M62653; SEQ ID NO:41), Luciferase (SEQ ID NO:42), or a combination thereof.

In specific embodiments of the present invention, a nucleic acid segment encoding a therapeutic or diagnostic protein or polypeptide is comprised in a vector, such as a nonviral vector, a viral vector, or a combination thereof. The viral vector may be an adenoviral vector, a retroviral vector, or an adeno-associated viral vector. The nonviral vector may be a plasmid or a liposome. The nucleic acid segment may also be comprised in a pharmaceutical composition.

Any combinations of the therapeutic or diagnostic fusion nucleic acids could be delivered as gene therapy reagents to use against cancer or angiogenesis-dependent diseases as one component along with an antiangiogenic gene product listed herein or known in the art. Alternatively, fusion proteins encoded by these fusion genes could be expressed and purified for protein therapy targeting cancer and other angiogenesis dependent diseases.

A skilled artisan recognizes that a therapeutic sequence may also serve as a diagnostic sequence, and vice versa. In other embodiments, an angiogenesis inhibitor coupled to a diagnostic agent is used prior to angiogenesis inhibitor coupled to a therapeutic agent.

General Embodiments

The present invention regards targeting anti-angiogenic fusion polypeptides and/or the nucleic acids that encode them, as well as methods regarding the use of same. Thus, in exemplary embodiments, the present inventors demonstrate that endogenous angiogenesis inhibitors, such as endostatin, tumstatin, angiostatin, etc., could specifically target new blood vessel formation, which is a hallmark of angiogenesis-dependent diseases, including cancer. Although any cancer may be treated or prevented in accordance with the present invention, some examples include head and neck, ovarian, thyroid, oral, prostate, melanoma, colon cancer, breast cancer, angioma, sarcoma, lung cancer, brain cancer, pancreatic cancer, liver cancer, bladder cancer, gastrointestinal cancer, leukemia, lymphoma, and myeloma.

Specifically, these antiangiogenic proteins could be fused with therapeutic or diagnostic proteins and serve as a guiding tool to deliver the fusion protein to the vicinity of pathological angiogenic sites. These fusion proteins encoded by fusion gene constructs enhanced the therapeutic effects by combining functions of both antiangiogenic and therapeutic proteins. In addition, the targeting property contributed by antiangiogenic proteins could minimize the systemic toxic effect of therapeutic proteins by targeting the fusion proteins to the disease site(s).

In a specific embodiment, the present invention regards anti-angiogenic targeting fusion proteins to treat cancer in a mammal. For example, human ovarian cancer, pancreatic cancer, breast cancer, prostate cancer, and other cancers may be treated with compositions described herein or taught to a skilled artisan by analogous procedures described herein. In some embodiments, it is delivered by, for example, either a viral or non-viral delivery system into an appropriate recipient animal to inhibit angiogenesis, suppress tumor growth and development, or a combination thereof.

Exemplary anti-angiogenic targeting fusion proteins were generated. These fusions in preferred embodiments of the present invention, selectively inhibit angiogenesis, inhibit cell proliferation, inhibit cancer cell growth, or a combination thereof. One skilled in the art following the teachings of this specification can generate other exemplary anti-angiogenic targeting fusion proteins.

In some embodiments of the present invention, there are methods of preventing growth of a cell in an individual comprising administering to the individual an anti-angiogenic targeting fusion polypeptide. In specific embodiments, the polypeptide is administered in a liposome and/or the polypeptide further comprises a protein transduction domain (Schwarze et al., 1999). In some embodiments, an anti-angiogenic targeting fusion protein is administered as a polynucleotide, wherein the polynucleotide comprises an alteration that effects modification at the amino acid level, such as may be generated by site-directed mutagenesis. The modified anti-angiogenesis targeting fusion polynucleotide may be administered in a vector such as a plasmid, retroviral vector, adenoviral vector, adeno-associated viral vector, liposome, or a combination thereof.

There are also embodiments of the present invention wherein there are methods of treating a cell comprising contacting the cell with an anti-angiogenic targeting fusion polypeptide. In specific embodiments, the cell is a human cell, the cell is comprised in an animal, and/or the animal is human.

Targeting Fusion Production

While the chimeric proteins of the present invention may be produced by chemical synthetic methods or by chemical linkage between the two moieties, it is preferred that they are produced by fusion of a coding sequence of an antiangiogenic moiety and a coding sequence of a therapeutic or diagnostic moiety under the control of a regulatory sequence that directs the expression of the fusion polynucleotide in an appropriate host cell. In preferred embodiments, each of the components of the chimeric protein comprise functional activity for their respective parts being an antiangiogenic moiety and a therapeutic or diagnostic moiety.

The fusion of two full-length coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two separate encoded products. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a linker. In a specific embodiment, a linker for connecting the antiangiogenic and therapeutic/diagnostic proteins comprises either VPGVG (elastin Val-Pro-Gly-Val-Gly) or Gly-Gly-Gly-Ser-Gly. Other linkers are known to those of skill in the art, such as are described in WO 99/16889, which is incorporated by reference herein in its entirety.

In accordance with the objects of the present invention, a polynucleotide that encodes a fusion protein may be used to generate recombinant DNA molecules that direct the expression of the fusion protein, fusion peptide fragments, or a functional equivalent thereof, in appropriate cells. Due to the inherent degeneracy of the genetic code, other DNA sequences that encode substantially the same or a functionally equivalent amino acid sequence, may be used in the practice of the invention of the cloning and expression of the fusion protein. Such DNA sequences include those capable of hybridizing to the fusion sequences or their complementary sequences under stringent conditions, which are well known to a skilled artisan.

Altered DNA sequences that may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a fusion sequence, which result in a silent change thus producing a functionally equivalent fusion protein. Such amino acid substitutions may be made on the basis of similarity in polarity, charge, solubility, hydrophobicity, hydrophilicity, and/or the amphipathic nature of the residues involved, which is well known to a skilled artisan.

The DNA sequences of the invention may be engineered in order to alter a fusion coding sequence for a variety of ends, including but not limited to, alterations that modify processing and expression of the gene product, as described elsewhere in greater detail. For example, mutations may be introduced using techniques which are well known in the art, e.g., site-directed mutagenesis, to insert new restriction sites, to alter glycosylation patterns, phosphorylation, etc.

In one embodiment of the invention, the coding sequence of the fusion protein could be synthesized in whole or in part, using chemical methods well known in the art. (See, for example, Caruthers et al., 1980; Crea and Horn, 1980; and Chow and Kempe, 1981). For example, active domains of the moieties can be synthesized by solid phase techniques, cleaved from the resin, and purified by preparative high performance liquid chromatography followed by chemical linkage to form a chimeric protein. (e.g., see Creighton, 1983, Proteins Structures And Molecular Principles, W. H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y. pp. 34-49). Alternatively, the two moieties of the fusion protein produced by synthetic or recombinant methods may be conjugated by chemical linkers according to methods well known in the art (Brinkmann and Pastan, 1994).

In order to express a biologically active fusion protein, the nucleotide sequence coding for a chimeric protein, or a functional equivalent, is inserted into an appropriate expression vector, i.e., a vector which contains the necessary elements for the transcription and translation of the inserted coding sequence, as described elsewherein in greater detail. The fusion gene products as well as host cells or cell lines transfected or transformed with recombinant fusion expression vectors can be used for a variety of purposes. These include but are not limited to generating antibodies (i.e., monoclonal or polyclonal) that bind to epitopes of the proteins to facilitate their purification.

Methods that are well known to those skilled in the art can be used to construct expression vectors containing the fusion protein coding sequence and appropriate transcriptional/translational control signals, as discussed elsewhere in greater detail. These methods include in vitro recombinant DNA techniques, synthetic techniques and in vivo recombination/genetic recombination.

A variety of host-expression vector systems may be utilized to express the fusion protein coding sequence, and these are well known in the art.

Specific initiation signals may be required for efficient translation of the inserted fusion protein coding sequence. These signals include the ATG initiation codon and adjacent sequences. In cases where the entire fusion gene, including its own initiation codon and adjacent sequences, is inserted into the appropriate expression vector, no additional translational control signals may be needed. However, in cases where the fusion protein coding sequence does not include its own initiation codon, exogenous translational control signals, including the ATG initiation codon, must be provided. Furthermore, the initiation codon must be in phase with the reading frame of the fusion protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

Definitions and Techniques Affecting Targeting Fusion Gene Products and Genes

Targeting Fusion Gene Products and Genes

As used herein, the terms "targeting fusion gene product" and "targeting fusion" refer to proteins or polypeptides having amino acid sequences that comprise at least one anti-angiogenesis component and at least one therapeutic and/or diagnostic component in said fusion and that are biologically active in that they are capable performing similar activities to at least one of their native components, and in some embodiments both components are capable of performing activities similar to the native separate components. For example, they are preferably capable of anti-angiogenesis activity, pro-apoptotic activity, anti-cell proliferative activity, anti-tumor activity and/or cross-reactive antibody activity with an anti-targeting fusion antibody raised against at least one component of the targeting fusion gene product. The term "targeting fusion gene product" includes analogs of targeting fusion molecules that exhibit at least some biological activity in common with native targeting fusion. Furthermore, those skilled in the art of mutagenesis will appreciate that other analogs, as yet undisclosed or undiscovered, may be used to construct targeting fusion analogs.

The term "mutant form of targeting fusion" refers to any DNA sequence that is substantially identical to a DNA sequence encoding at least a part of the targeting fusion gene product as defined above. The term also refers to RNA or antisense sequences compatible with such DNA sequences. A "targeting fusion gene" may also comprise any combination of associated control sequences.

The term "substantially identical", when used to define either a targeting fusion amino acid sequence or targeting fusion nucleic acid sequence, means that a particular subject sequence, for example, a mutant sequence, varies from the sequence of its separate components by, for example, one or more substitutions, deletions, additions, or a combination thereof, the net effect of which is to retain at least some biological activity of at least part of the respective component part. Alternatively, DNA analog sequences are "substantially identical" to specific DNA sequences disclosed herein if: (a) the DNA analog sequence is derived from at least part of a coding region of the targeting fusion gene; or (b) the DNA analog sequence is capable at least in part of hybridization of DNA sequences of (a) under moderately stringent conditions and which encode biologically active targeting fusion; or (c) DNA sequences that are degenerative as a result of the genetic code at least part of to the DNA analog sequences defined in (a) or (b). Substantially identical analog proteins will be greater than about 80% similar to the corresponding sequence of the native protein component. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of targeting fusion nucleic acids, genes and gene products, or the corresponding protein, polypeptide, or peptide. The term "a sequence essentially as targeting fusion" means that the sequence substantially corresponds to at least a portion of the targeting fusion gene and has relatively few bases or amino acids (whether DNA or protein) that are not identical to those of targeting fusion (or a biologically functional equivalent thereof, when referring to proteins). The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to at least part of the amino acids of targeting fusion will be sequences that are "essentially the same".

Targeting fusion nucleic acids that have at least part of their sequence comprising functionally equivalent codons are covered by the invention. The term "functionally equivalent codon" is used herein to refer to codons that encode the same amino acid, such as the six codons for arginine or serine, and also refers to codons that encode biologically equivalent amino acids (Table 1).

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

-continued

| Amino Acids | | | Codons |
|---|---|---|---|
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments that are complementary, or essentially complementary, to the sequences set forth in the specification. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in at least part of the structure of angiogenesis inhibitor coupled to a therapeutic or diagnostic agent, such as an anti-angiogenesis targeting fusion, and still obtain a molecule having like or otherwise desirable characteristics. In a specific embodiment, a skilled artisan recognizes that the scope of the angiogenesis inhibitor coupled to a therapeutic or diagnostic agent comprises an antiangiogenesis polypeptide region linked to a therapeutic protein or polypeptide region or a diagnostic protein or polypeptide region or a nucleic acid encoding a fusion protein comprising an antiangiogenesis polypeptide region linked to a therapeutic protein or polypeptide region or a diagnostic protein or polypeptide region.

For example, certain amino acids may be substituted for other amino acids in a protein structure without appreciable loss of activity. Since, in many embodiments, it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic vs. agonistic). It is thus contemplated by the inventors that various changes may be made in at least part of the sequence of the targeting fusion proteins or peptides (or underlying DNA) without appreciable loss of their desired biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Amino acid substitutions, such as those that might be employed in modifying targeting fusion, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those that are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Combination Treatments

In order to increase the effectiveness of an angiogenesis inhibitor coupled to a therapeutic or diagnostic agent, such as an anti-angiogenic targeting fusion protein, or expression construct coding therefore, it may be desirable to combine these compositions with other agents effective in the treatment of disease related to angiogenesis, such as, for example, anti-cancer agents for cancer. An "anti-cancer" agent is capable of negatively affecting cancer in a subject, for example, by inhibiting angiogenesis for a cancer cell and/or tissue, killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that targeting fusion gene therapy could be used similarly in conjunction with chemotherapeutic, radiotherapeutic, or immunotherapeutic intervention, in addition to other pro-apoptotic or cell cycle regulating agents.

Alternatively, the combination therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations, in an exemplary embodiment, may be employed, although gene therapy is "A" and the secondary agent, such as radiotherapy, chemotherapy, surgery, or immunotherapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

Nucleic Acid-Based Expression Systems

Vectors

In one embodiment, a targeting fusion nucleic acid is comprised on a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202; U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In a specific embodiment, a promoter is utilized that is tissue-specific and/or specific to the microenvironment surrounding the diseased tissue (such as the tumor), cell-specific, or cell type-specific. In a specific embodiment, a promoter such as one described in U.S. Provisional Patent Application Ser. No. 60/377,672, filed May 5, 2002, and entitled "BIPARTITE T-CELL FACTOR (TCF)-RESPONSIVE PROMOTER" and in U.S. Nonprovisional Patent Application Ser. No. 10/429,802, filed May 5, 2003 under Express Mail number EU 110397859US, both of which are incorporated by reference herein in their entirety, is utilized in the present invention.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Nucleic Acid Delivery

The general approach to the aspects of the present invention concerning compositions and/or therapeutics is to provide a cell with a gene construct encoding a specific and/or desired protein, polypeptide and peptide, thereby permitting the desired activity of the proteins to take effect. In the present invention, the desired protein, polypeptide, or peptide is a targeting fusion comprising an angiogenesis inhibitor and a therapeutic or diagnostic sequence. While it is conceivable that the gene construct and/or protein may be delivered directly, a preferred embodiment involves providing a nucleic acid encoding a specific and desired protein, polypeptide and peptide to the cell. Following this provision, the proteinaceous composition is synthesized by the transcriptional and translational machinery of the cell, as well as any that may be provided by the expression construct. In providing antisense, ribozymes and other inhibitors, the preferred mode is also to provide a nucleic acid encoding the construct to the cell.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments and "episomes" encode sequences sufficient to permit maintenance and replication independent of and in synchronization with the host cell cycle. How the expression construct is delivered to a cell and/or where in the cell the nucleic acid remains is dependent on the type of expression construct employed.

DNA Delivery Using Viral Vectors

The ability of certain viruses to infect cells and enter cells via receptor-mediated endocytosis, and to integrate into host cell genome and/or express viral genes stably and/or efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and/or in the range of cells they infect, these viruses have been demonstrated to successfully effect gene expression. However, adenoviruses do not integrate their genetic material into the host genome and/or therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles and endotoxins and other pyrogens such that it will not cause any untoward reactions in the cell, animal and/or individual receiving the vector construct. A preferred means of purifying the vector involves the use of buoyant density gradients, such as cesium chloride gradient centrifugation Adenoviral Vectors A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and/or (b) to ultimately express a tissue and/or cell-specific construct that has been cloned therein.

The expression vector comprises a genetically engineered form of adenovirus. Knowledge of the genetic organization and adenovirus, a 36 kb, linear, double-stranded DNA virus, allows substitution of large pieces of adenoviral DNA with foreign sequences up to 7 kb (Grunhaus and Horwitz, 1992).

In contrast to retrovirus, the adenoviral infection of host cells does not result in chromosomal integration because adenoviral DNA can replicate in an episomal manner without potential genotoxicity. Also, adenoviruses are structurally stable, and/or no genome rearrangement has been detected after extensive amplification.

Adenovirus is particularly suitable for use as a gene transfer vector because of its mid-sized genome, ease of manipulation, high titer, wide target-cell range and/or high infectivity. Both ends of the viral genome contain 100-200 base pair inverted repeats (ITRs), which are cis elements necessary for viral DNA replication and/or packaging. The early (E) and/or late (L) regions of the genome contain different transcription units that are divided by the onset of viral DNA replication. The E1 region (E1A and/or E1B) encodes proteins responsible for the regulation of transcription of the viral genome and/or a few cellular genes. The expression of the E2 region (E2A and/or E2B) results in the synthesis of the proteins for viral DNA replication. These proteins are involved in DNA replication, late gene expression and/or host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and/or all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and constitutively expresses E1 proteins (E1A and/or E1B; Graham et al., 1977). Since the E3 region is dispensable from the adenovirus genome (Jones and Shenk, 1978), the current adenovirus vectors, with the help of 293 cells, carry foreign DNA in either the E1, the D3 and both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and/or E3 regions, the maximum capacity of the current adenovirus vector is under 7.5 kb, and/or about 15% of the total length of the vector. More than 80% of the adenovirus viral genome remains in the vector backbone.

Helper cell lines may be derived from human cells such as human embryonic kidney cells, muscle cells, hematopoietic cells and other human embryonic mesenchymal and epithelial cells. Alternatively, the helper cells may be derived from the cells of other mammalian species that are permissive for human adenovirus. Such cells include, e.g., Vero cells and other monkey embryonic mesenchymal and/or epithelial cells. As stated above, the preferred helper cell line is 293.

Recently, Racher et al (1995) disclosed improved methods for culturing 293 cells and/or propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l ) is employed as follows. A cell inoculum, resuspended in 5 ml of medium, is added to the carrier (50 ml) in a 250 ml Erlenmeyer flask and/or left stationary, with occasional agitation, for 1 to 4 h. The medium is then replaced with 50 ml of fresh medium and/or shaking initiated. For virus production, cells are allowed to grow to about 80% confluence, after which time the medium is replaced (to 25% of the final volume) and/or adenovirus added at an MOI of 0.05. Cultures are left stationary overnight, following which the volume is increased to 100% and/or shaking commenced for another 72 h.

Other than the requirement that the adenovirus vector be replication defective, and at least conditionally defective, the nature of the adenovirus vector is not believed to be crucial to the successful practice of the invention. The adenovirus may be of any of the 42 different known serotypes and subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) and in the E4 region where a helper cell line and helper virus complements the E4 defect.

Adenovirus growth and/or manipulation is known to those of skill in the art, and/or exhibits broad host range in vitro and in vivo. This group of viruses can be obtained in high titers, e.g., 109 to 1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and/or therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and/or stereotactic inoculation into the brain (Le Gal La Salle et al., 1993). Recombinant adenovirus and adeno-associated virus (see below) can both infect and transduce non-dividing human primary cells.

AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) and in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and/or U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus and a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome and from a recombinant plasmid, and/or a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and/or an expression plasmid containing the wild type AAV coding sequences without the terminal repeats, for example pIM45 (McCarty et al., 1991; incorporated herein by reference). The cells are also infected and transfected with adenovirus and plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions and cell lines containing the AAV coding regions and some and all of the adenovirus helper genes could be used (Yang et al., 1994; Clark et al., 1995). Cell lines carrying the rAAV DNA as an integrated provirus can also be used (Flotte et al., 1995).

Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and/or directs synthesis of viral proteins. The integration results in the retention of the viral gene sequences in the recipient cell and/or its descendants. The retroviral genome contains three genes, gag, pol, and/or env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and/or stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

Specific retroviral vectors useful in the present invention include lentivirus and Vesicular Stomatitis Virus-Indiana.

Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and/or herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes and expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and/or can be grown to high titers. Thus, delivery is less of a problem, both in terms of volumes needed to attain sufficient MOI and in a lessened need for repeat dosings Modified Viruses In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Other Methods of DNA Delivery

In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA and/or plasmids. Transfer of the construct may be performed by any of the methods mentioned which physically and/or chemically permeabilize the cell membrane. Some of these techniques may be successfully adapted for in vivo and/or ex vivo use, as discussed below.

Liposome-Mediated Transfection

In a further embodiment of the invention, the expression construct may be entrapped in a liposome. Liposomes are vesicular structures characterized by a phospholipid bilayer membrane and/or an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and/or entrap water and/or dissolved solutes between the lipid bilayers (Ghosh and Bachhawat, 1991). Also contemplated is an expression construct complexed with Lipofectamine (Gibco BRL). Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and/or expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and/or promote cell entry of liposome-encapsulated DNA (Kaneda et al., 1989). In other embodiments, the liposome may be complexed and/or employed in conjunction with nuclear non-histone chromosomal proteins (HMG-1) (Kato et al., 1991). In yet further embodiments, the liposome may be complexed and/or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

As described in U.S. Pat. No. 5,641,484, liposomes are particularly well suited for the treatment of HER2/neu-mediated cancer Preparation of Liposomes Catatonic liposomes that are efficient transfection reagents for targeting fusion for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3'(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 μmol of DC-Chol and 8.0 μmol of DOPE in chloroform. This mixture is then dried, vacuum desiccated, and resuspended in 1 ml sterol 20 mM Hepes buffer (pH 7.8) in a tube. After 24 hours of hydration at 4° C., the dispersion is sonicated for 5-10 minutes in a sonicator form liposomes with an average diameter of 150-200 nm.

To prepare a liposome/DNA complex, the inventors use the following steps. The DNA to be transfected is placed in DMEM/F12 medium in a ratio of 15 μg DNA to 50 μl DMEM/F12. DMEM/F12 is then used to dilute the DC-Chol/DOPE liposome mixture to a ratio of 50 μl DMEZM/F12 to 100 μl liposome. The DNA dilution and the liposome dilution are then gently mixed, and incubated at 37° C. for 10 minutes. Following incubation, the DNA/liposome complex is ready for injection.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3 .beta.[N-(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. In a specific embodiment, the liposomes comprise DC-Chol. More particularly, the inventors the liposomes comprise DC-Chol and DOPE which have been prepared following the teaching of Gao et al. (1991) in the manner described in the Preferred Embodiments Section. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a nucleic acid encoding an anti-angiogenic targeting fusion. The nucleic acid encoding the targeting fusion employed in the liposomal complex can be, for example, one which encodes targeting fusions described herein.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

In a specific embodiment, one employs the smallest region needed to enhance retention of targeting fusion in the nucleus of a cell so that one is not introducing unnecessary DNA into cells which receive a targeting fusion gene construct. Techniques well known to those of skill in the art, such as the use of restriction enzymes, will allow for the generation of small regions of targeting fusion. The ability of these regions to inhibit neu can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

In vivo Treatment of Cancer Via Liposomes with Targeting Fusions

Based on the teachings provided herein, a skilled artisan recognizes that any cell may be treated with at least one targeting fusion, and in particular embodiments, any cancer cell may be treated with such. For example, in some embodiments the nature of the treated cell is irrespective of being HER2/neu-positive or HER2/neu-negative.

U.S. Pat. No. 5,641,484, incorporated in its entirety by reference herein, teaches that liposome-mediated direct gene transfer techniques can be employed to obtain suppression of HER2/neu-overexpressing human cancer cells in living host. The exemplary protocol for described therein was as follows. Female nude mice (5-6 weeks old) were given intraperitoneal injections of SK-OV-3 cells ($2\times10^6$/100 μl). SK-OV-3 cells are human ovarian cancer cells that have been shown to grow within the peritoneal cavity of nude mice. After five days, the mice were given intraperitoneal injections of various compounds. Some mice were injected with the therapeutic DNA alone, some were injected with liposome/therapeutic DNA complex prepared in the manner described above, and some were injected with liposome/mutant therapeutic DNA complex. 200 μl of a given compound was injected into a given mouse. After the initial injections, injections were repeated every seven days throughout the life of the mouse.

The results described therein indicate that liposome-mediated gene transfer can inhibit HER2/neu-overexpressing human ovarian cancer cell growth. Therefore, it is predictable that liposome-mediated targeting fusion gene therapy may serve as a powerful therapeutic agent for HER-2 neu-overexpressing human ovarian cancers by direct targeting of targeting fusion at the HER-2 neu-oncogene.

Liposomal Transfection with Targeting Fusion to Treat Humans

Based on the results of the in vivo animal studies described in U.S. Pat. No. 5,641,484, those of skill in the art will understand and predict the enormous potential for human treatment of HER2/neu-mediated cancers with an anti-angiogenic targeting fusion complexed to liposomes. Clinical studies to demonstrate these effects are contemplated. Those of skill in the art will recognize that the best treatment regimens for using targeting fusions to suppress cancers can be straightforwardly determined. This is not a question of experimentation, but rather one of optimization, which is routinely conducted in the medical arts. In vivo studies in nude mice provide a starting point from which to begin to optimize the dosage and delivery regimes. The frequency of injection is initially once a week, as was done in the mice studies described in U.S. Pat. No. 5,641,484. However, this frequency might be optimally adjusted from one day to every two weeks to monthly, depending upon the results obtained from the initial clinical trials and the needs of a particular patient. Human dosage amounts can initially be determined by extrapolating from the amount of targeting fusion used in mice, approximately 15 μg of plasmid DNA per 50 g body weight. Based on this, a 50 kg woman would require treatment with 15 mg of DNA per dose. Of course, this dosage amount may be adjusted upward or downward, as is routinely done in such treatment protocols, depending on the results of the initial clinical trials and the needs of a particular patient. These clinical trials are anticipated to show utility of targeting fusions for the treatment of HER2/neu-overexpressing cancers in humans. Dosage and frequency regimes will initially be based on the data obtained from in vivo animal studies, as is done frequently in the art Electroporation In certain embodiments of the present invention, the expression construct is introduced into the cell via electroporation. Electroporation involves the exposure of a suspension of cells and/or DNA to a high-voltage electric discharge.

Transfection of eukaryotic cells using electroporation has been quite successful. Mouse pre-B lymphocytes have been transfected with humankappa-immunoglobulin genes (Potter et al., 1984), and/or rat hepatocytes have been transfected with the chloramphenicol acetyltransferase gene (Tur-Kaspa et al., 1986) in this manner.

Calcium Phosphate and/or DEAE-Dextran

I other embodiments of the present invention, the expression construct is introduced to the cells using calcium phosphate precipitation. HumanKB cells have been transfected with adenovirus 5 DNA (Graham and Van Der Eb, 1973) using this technique. Also in this manner, mouse L(A9), mouse C127, CHO, CV-1, BHK, NIH3T3 and/or HeLa cells were transfected with a neomycin marker gene (Chen and Okayama, 1987), and/or rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and/or erythroleukemia cells (Gopal, 1985).

Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and/or enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten and/or gold beads.

Direct Microinjection and/or Sonication Loading

Further embodiments of the present invention include the introduction of the expression construct by direct microinjection and/or sonication loading. Direct microinjection has been used to introduce nucleic acid constructs into Xenopus oocytes (Harland and Weintraub, 1985), and/or LTK-fibroblasts have been transfected with the thymidine kinase gene by sonication loading (Fechheimer et al., 1987).

Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

Pharmaceutical Preparations

Pharmaceutical compositions of the present invention comprise an effective amount of one or more forms of an angiogenesis inhibitor coupled to a therapeutic or diagnostic agent, such as an anti-angiogenesis targeting fusion and/or additional agent dissolved or dispersed in a pharmaceutically acceptable carrier or excipient. The phrases “pharmaceutical or pharmacologically acceptable” refers to molecular entities and compositions that do not produce an adverse, allergic or other untoward reaction when administered to an animal, such as, for example, a human, as appropriate. The preparation of an pharmaceutical composition that contains at least one targeting fusion form or additional active ingredient will be known to those of skill in the art in light of the present disclosure, as exemplified by Remington’s Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, “pharmaceutically acceptable carrier” includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington’s Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The targeting fusion form may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington’s Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The targeting fusion form may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the targeting fusion form is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

In a particular embodiment of the present invention, a composition is utilized wherein the composition is an anti-angiogenic targeting fusion, the expression of which is regulated at least in part by a promoter comprising one such as is described in U.S. Provisional Patent Application Ser. No. 60/377,672, filed May 5, 2002, and entitled "BIPARTITE T-CELL FACTOR (TCF)-RESPONSIVE PROMOTER" and in U.S. Nonprovisional Patent Application Ser. No 10/429,802, filed May 5, 2003 under Express Mail number EU 110397859US, both of which are incorporated by reference herein in their entirety, and wherein said fusion is comprised with a liposome, such as DC-Chol, DOTMA, and the like.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Immunoblotting: The endostatin, endostatin-cytosine deaminase (endo-CD), and endostatin-interleukin-12 (endo-IL12) containing plasmid was used to transfect 293T cells using the cationic liposome method. After transfection, the medium was replaced by serum free medium. Then, after a 24 hr incubation, the supernatant was collected and western blotted with anti-endostatin antibody.

ELISA: COS-7 cells were transfected with plasmids encoding either, Endostatin-IL2 or Endostatin-GM-CSF using cationic liposome. After transfection, the medium was replaced wtih serum free medium and the supoernatant was harvested and subjected to ELISA to detect the endostatin protein.

Example 2

Expression of Antiangiogenic-Therapeutic/Diagnostic Fusion Genes

FIG. 1 shows that following production of fusion protein, antiangiogenic-therapeutic/diagnostic fusion protein could be detected. In FIG. 1A, there is an anti-endostatin antibody Western blot of supernatants collected from 293 cells. Eighteen KD endostatin(□), 58 KD endostatin-CD (◀), and 93 KD endo-IL12(←) could be detected. FIG. 1B illustrates that by using ELISA kit (specific for endostatin), endostatin-IL2 and endostatin-GM-CSF fusion proteins could also be detected and quantified.

Example 3

Exemplary Materials and Methods for Characterizing Antiangiogenic and Therapeutic/Diagnostic Functions of the Fusion Proteins Endothelial tube assay: Matrigel (Collaborative Biomolecules, Bedford, Mass.) was added (50 μl) to each well of a 96-well plate and allowed to polymerize. A suspension of 5,000 human umbilical endothelial cells (HUVEC) in EGM-2 medium without antibiotic was passed into each well coated with matrigel. The cells were treated with supernatants collected from different plasmid (endostatin, endostatin-CD, and CD) transfected 293T cells. All assays were performed in triplicate. Cell were incubated for 12-24 hr at 37° C. and viewed using a microscope. The cells were then photographed. Five fields were viewed, and tubes were counted and averaged.

Migration assay: The inhibitory effect of endostatin on VEGF-induced chemotaxis was tested on HUVECs using the Boyden chamber assay. After trypsinizing, washing, and diluting cells in M199 medium containing 0.5% FBS, 10,000 cells were seeded on the upper chamber wells, together with supernatant collected from 293T transfected with different plasmid (endostatin, endostatin-CD, and CD). M199 medium containing 2% FBS plus 10 ng/ml VEGF was placed in the lower chamber as a chemotactant. The cell-containing compartments were separated from the chemotactant with polycarbonate filter of 8 um pore size. The chamber was incubated at 37° C. for 6-8 hr. After discarding the non-migrated cells and washing the upper wells with PBS, the filters were scraped with a plastic blade, fixed in 4% formaldehyde in PBS, stained with DAPI fluorescent stain and placed on a glass slide. By using a fluorescent high power field, several independent homogenous images were recorded. Five fields were viewed, and tubes were counted and averaged. All assays were performed in triplicate.

MTT assay: The cytotoxic effect of 5FU converted from 5FC reacted with cytosine deaminase(CD) was 293T cells using MTT assay. The inventors use different plasmid(endostatin, endostatin-CD, and CD) to transfect 293T cells and incubated 12-14 hrs. After trypsinizing, washing, and diluting cells in DMEM medium containing 2% FBS plus different concentration of 5FU or 5FC, 5,000 cells were seeded on each well of 96-well plate. Then the plate was incubated at 37° C. for 3-4 days. The inventors add 20 μl of MTT solution and incubate for 2 hr, then 100 μl of lysing solution was added to each well and incubated overnight night. The light absorbance was measured at 570 nm on the following day.

Green fluorescence expression: The endostatin-GFP containing plasmid was used to transfect 293T cells with the same method. After 36 hr incubation, the GFP fluorescence was observed under fluorescent microscope.

NSF60 (GM-CSF dependent) Cell proliferation assay: To quantify the biological activity of the Endostatin-GM-CSF, the factor dependent cell line NSF60 was used. NSF60 cells were incubated with condition medium from COS-7 cells transfecte with either control plasmid, plasmid encoding Endostatin-GM-CSF, or two different concentrations of recombinant GM-CSF. After 48 hr of incubation, NSF60 proliferation was determined by measuring the activity of dehydrogenase-enzyme as marker for the biological activity, using 2 mg/ml Cell Titer 96TM MTS Reagent Powder (3-(4, 5-dimethylthiazol-2-yl)-5-(3-carboxymethoxyphenyl)-2-(4-sulfophenyl)-2H-tetrazolium inner salt) (Promega, USA) and 0.92 mg/ml Phenazine methosulfate (Sigma, USA). The $OD_{405}$ values reflected the cell numbers.

Example 4

Figure 2:
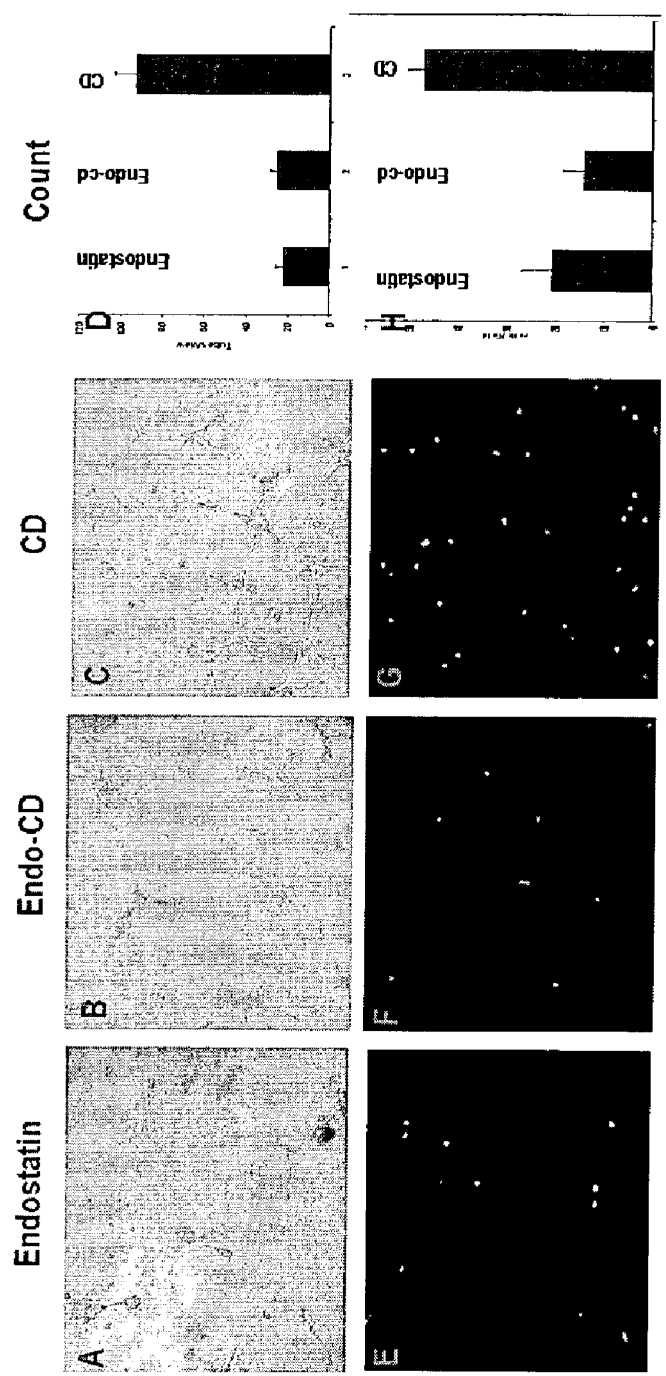
FIGS. 2A through 2H show that, in comparison to endostatin, endo-CD fusion protein exhibited similar antiangiogenic effects in endothelial tube (2A-2D) and migration (2E-2H) assays.

Fusion Proteins Possess both Antiangiogenic and Therapeutic/Diagnostic Functions FIG. 2 shows that, in comparison to endostatin, endo-CD fusion protein exhibit similar antiangiogenic effects in endothelial tube (FIGS. 2A-2D) and migration (FIGS. 2E-2H) assays. As supernatant collected from endostatin gene transfection, the supernatant from endostatin-CD fusion gene demonstrated inhibitory effect on HUVEC cell tube formation (FIGS. 2A, 2B, and 2C) and cell migration (FIGS. 2E, 2F, and 2G). In FIGS. 2D and 2H, five fields were viewed, and the tubes or migrated cells were counted and averaged.

Figure 3:
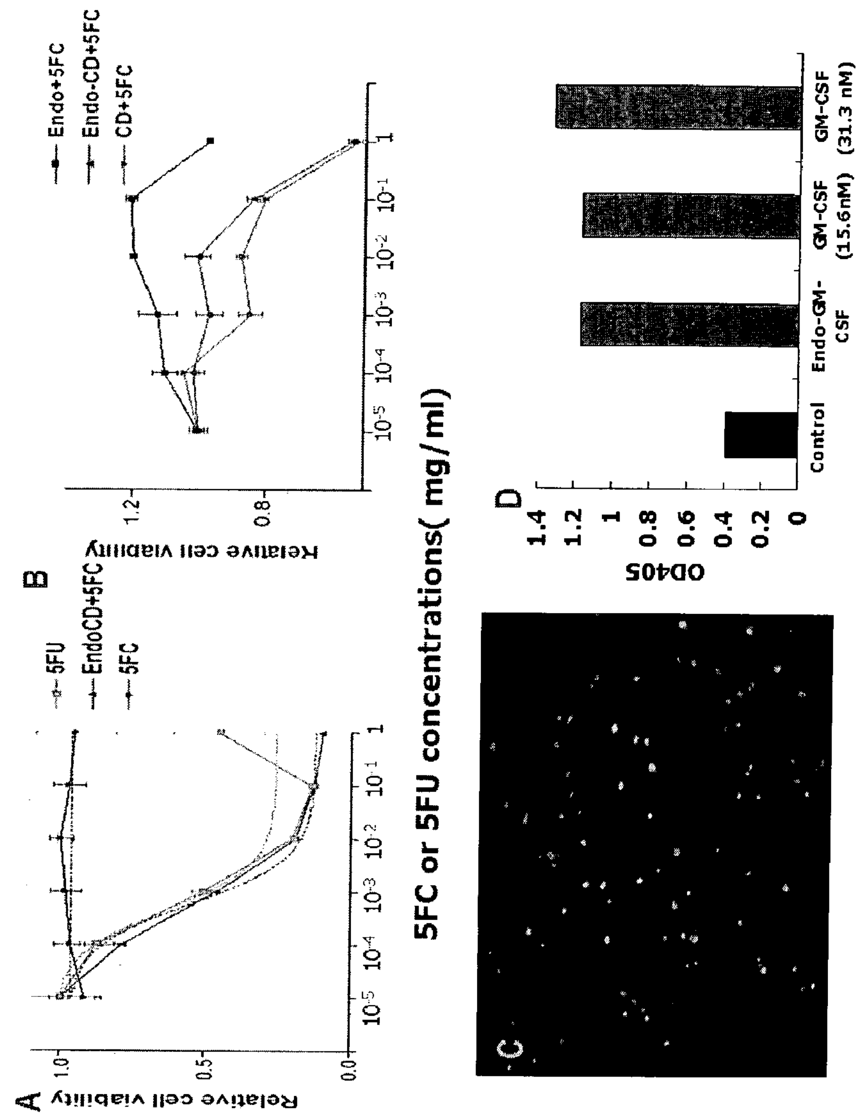
FIGS. 3A through 3D demonstrate that therapeutic or diagnostic functions of fusion genes could be detected.

FIG. 3 illustrates that therapeutic or diagnostic functions of fusion genes could be detected. In FIGS. 3A and 3B, a MTT assay is provided. As different concentrations of 5FU or 5FC with CD gene transfection were provided, endo-CD gene transfection demonstrated the killing effect on 293T cells. In FIG. 3C, green fluorescent protein expression in 293T cells transfected with Endo-GFP fusion gene could be detected by fluorescent microscope. In FIG. 3D, the cell proliferation of NSF60 could be stimulated by conditional medium from COS-7 transfected by Endostatin-GM-CSF plasmid. $OD_{405}$ values of NSF60 incubated with conditional medium from COS-7 transfected by Endostatin-GM-CSF plasmid was slightly better than those cells incubated with 15.6 nM recombinant GM-CSF protein. Therefore, the protein encoded by Endostatin-GM-CSF plasmid exhibited GM-CSF function, as evidenced by proliferation of GM-CSF dependent NSF60.

Example 5

Exemplary Materials and Methods for Tumor-Specific Targeting Effect of Antiangiogenic-Therapeutic/Diagnostic Fusion Proteins In vitro Endothelial Cell Targeting To demonstrate the specific targeting effect of antiangiogenic/therapeutic or antiangiogenic/diagnostic fusion gene, the inventors seeded the previously established 293T endostatin-GFP stable clone to a 10 cm plate. At the same time, different cell lines (MDA-231 breast cancer cell, mouse endothelial cell-SVEC, and human endothelial cell-HUVEC) were seeded to a 4-chamber plate. After the cells attached, the inventors put the 4-well plate into the 10 cm plate and added enough medium to cover all the wells. After 48 hr incubation, the 4-well plate was washed with PBS and the green fluorescence was observed under the fluorescent microscope.

In vivo Tumor Targeting

The inventors subcutaneously injected $2\times10^5$ B16 cells from parental cell line or endostatin-GFP stable clone to 7-9-week-old B57 mice. Each mice bears two injection sites. In experimental group, the inventors injected B16 parental cells to one site and B16 endostatin-GFP cells to the other. In control group, both sites received the tumor cells from B16 parental cells. After 14 days, the tumors were harvested and fixed. The inventors use anti-GFP antibody for immunohistochemical staining.

Example 6

Figure 4:
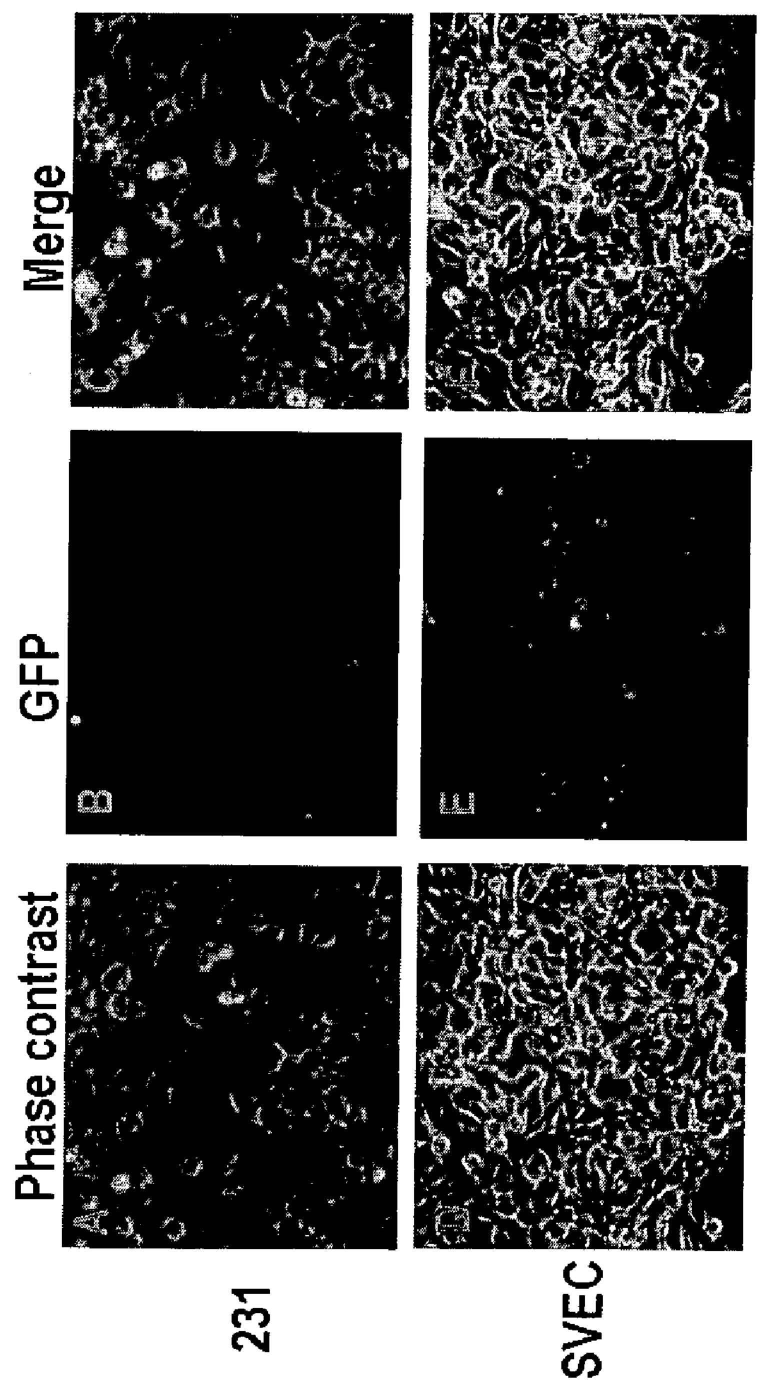
FIGS. 4A through 4F demonstrate that endostatin-GFP specifically targets to endothelial cells.

Tumor Specific Targeting Effect of Antiangiogenic-Therapeutic/Diagnostic Fusion Proteins FIG. 4 shows that endostatin-GFP specifically targets to endothelial cells. After being incubated with 293T endostatin-GFP stable clone for 48 hr, a lot of green fluorescent signals could be detected in SVEC mouse endothelial cell (E) but not in MDA-231 breast cancer cells (B).

Figure 5:
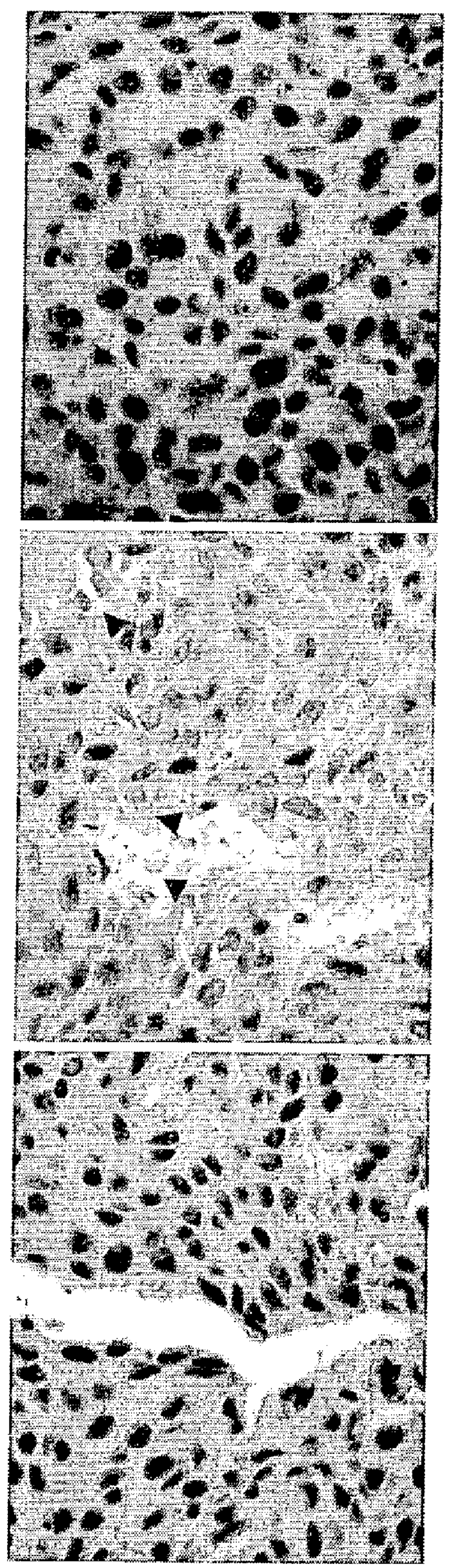
FIGS. 5A through 5C show that GFP signal was detected in the vascular wall of B-16 parental tumors.

FIG. 5 GFP signal was detected in the vascular wall of B-16 parental tumors. FIG. 5A demonstrates an experimental group. Diffuse GFP signal was found in tumor of B-16 endostatin-GFP stable cell lines. FIG. 5B shows in contralateral tumor to A (from B-16 parental cell lines), GFP signal was found in blood vessel wall (◀). In FIG. 5C, there is no GFP signals could be detected in tumors from bilateral B-16 parental cell lines in control group.

Example 7

Exemplary Materials and Methods for Animal Models of

Endostatin-GFP Inhibit both Regional and Distant Tumor Growth

Endostatin-GFP plasmid was used to transfect B16 melanoma cell. After the stable clones were established, the inventors subcutaneously injected $2\times10^5$ B16 cells from parental cell line or endostatin-GFP stable clone to 7-9-week-old B57 mice. The animals were divided into two groups. Each group contained 10 mice, and every mice had two injection sites. In the experimental group, the inventors injected B16 parental cells to one site and B16 endostatin-GFP cells to the other. In the control group, both sites received the tumor cells from B16 parental cells. The tumors were measured and calculated on the 14th day. Volume±S.D. is plotted.

Superior Anticancer Effect of Fusion Proteins Against Regional Tumor

B16F10 melanoma tumor model—Either $1\times10^6$ cells or $2.5\times10^5$ cells of B16-F10 were injected subcutaneously into the right flank of 6-7 week-old C57/BL6 immunocompetent female mice. Four days after inoculation, tumors (about 5 mm in diameter) were directly injected with different plasmid DNA encoding Luciferase, Endostatin, IL12, or Endostatin-IL12 and cationic liposome complexes (in 100 μl saline). The treatment was repeated three times a day for every four days. Seventeen days after the tumor was inoculated, the tumor sizes of each experimental group were measured.

CT-26 colon cancer model—CT-26 colon cancer cells ($2\times10^5$) were injected subcutaneously into 7-9-week-old B57CL6 mice on right flank. Simultaneously, another set of CT-26 melanoma cells ($2\times10^5$) were injected subcutaneously into the left flank of the mice. Four days after the tumor was challenged, different plasmids containing either Luciferase (Luc), endostatin (Endo), interleukin-12 (IL-12), or Endo-IL12 fusion gene were intratumorally injected into the left flank CT-26 tumor. This procedure was repeated twice a week, and the tumor size was measured every two days. The size of distant tumor on the right flank was calculated and plotted over the treatment period.

Example 8

Animal Models of Antiangiogenic-Therapeutic/Diagnostic Fusion Proteins

Figure 6:
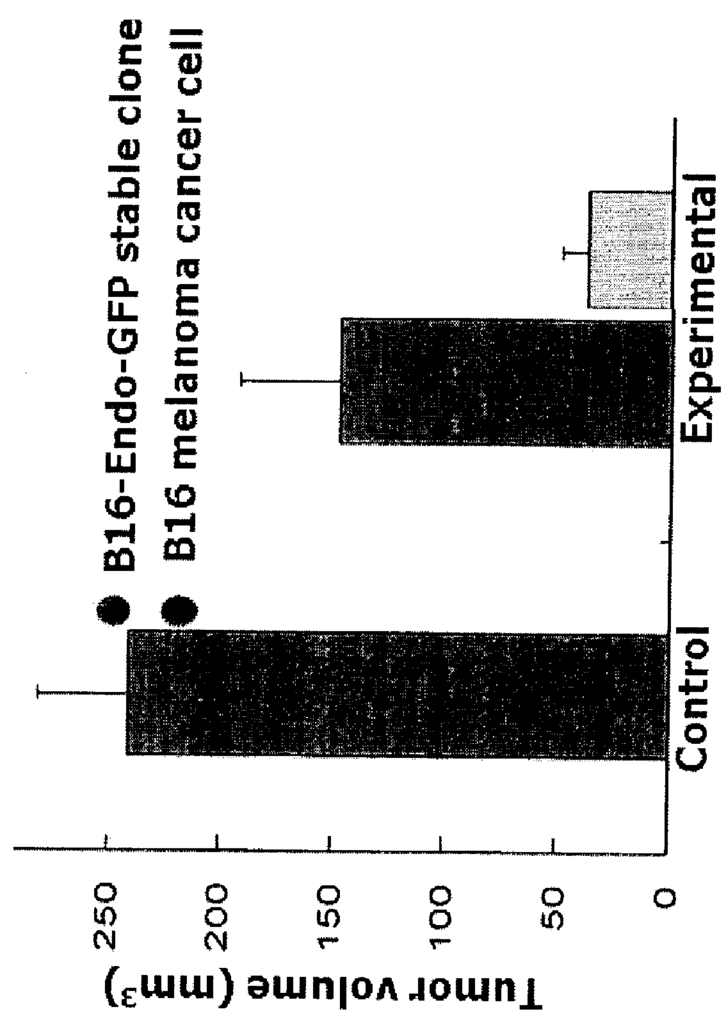
FIG. 6 shows that stable clone-expressed endostatin-GFP inhibits contra-lateral and local tumor growth. In a control group, all of the tumors were measured and averaged together. The tumors in the experimental group were measured and averaged according to their cell lines (B16 parental melanoma cell line or endostatin-GFP stable clones).

FIG. 6 shows stable clone-expressed endostatin-GFP inhibits contra-lateral and local tumor growth. In a control group, all the tumors were measured and averaged together. The tumors in an experimental group were measured and averaged according to their cell lines (B16 parental melanoma cell line or endostatin-GFP stable clones).

Figure 7:
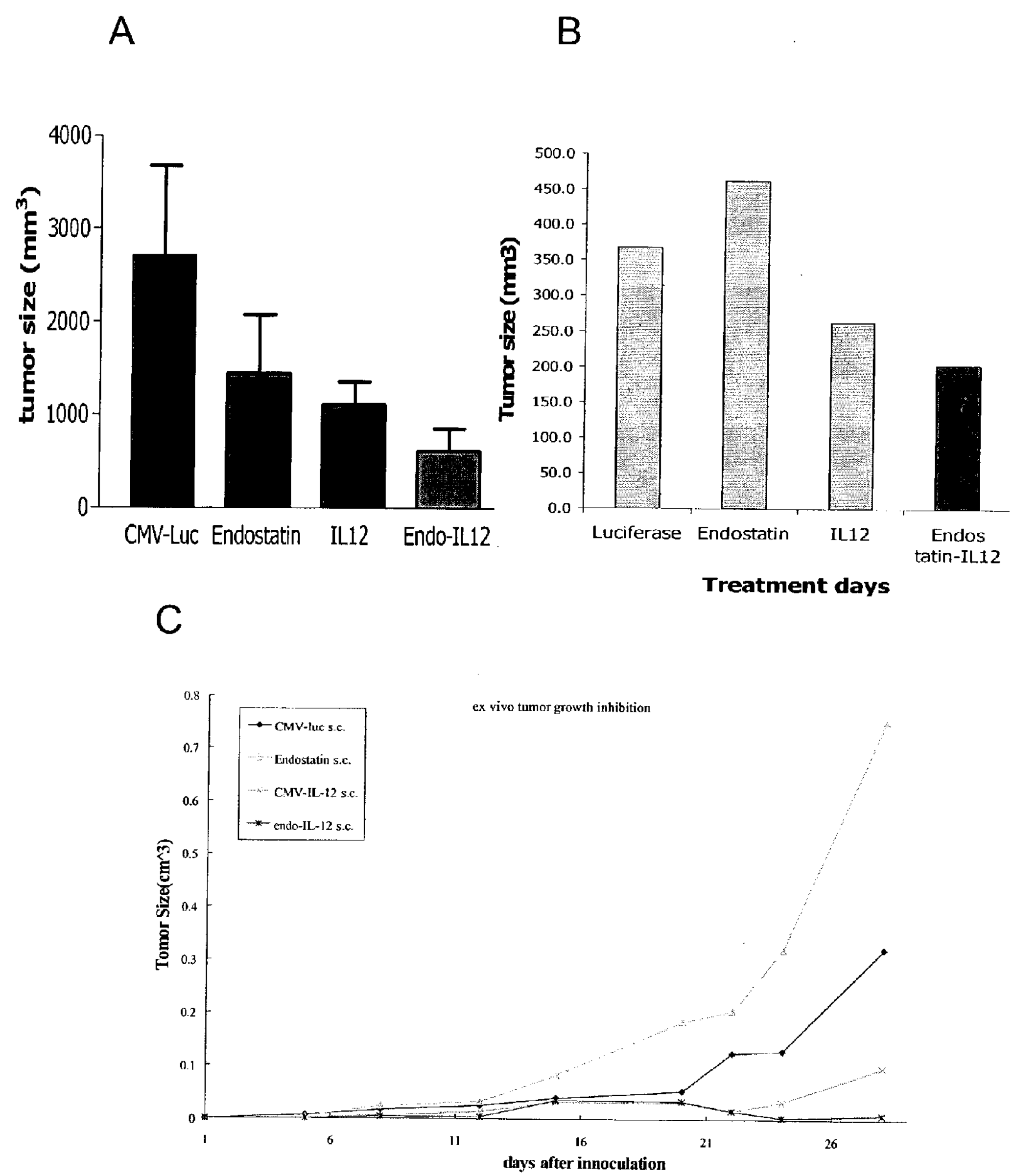
FIGS. 7A through 7C demonstrate that endo-IL12 has a superior anticancer effect compared with IL12 or endostatin alone in different independent animal studies.

FIG. 7 shows that endo-IL12 has a superior anticancer effect compared to IL12 or endostatin alone in different independent animal studies. In FIG. 7A, there is intratumoral gene therapy against B16F10 tumor. Endostatin-IL12 demonstrates the most significant anti-cancer effect on subcutaneous xenograft B16-F10 melanoma cancer compared to both endostatin and IL12 genes. In FIG. 7B, there is similar intratumoral gene therapy as in FIG. 7A against B16F10 tumor, except the original distant tumor was challenged at $2\times10^5$ cell. The endo-IL12 still showed better therapeutic effect than IL12 and endostatin alone, as provided in FIG. 7C.

Example 9

Materials and Methods for Anticancer Effect of Fusion Proteins Against Distant Tumor Ex vivo transfection: B16-F10 melanoma cells ($2\times10^5$) were injected subcutaneously into 7-9-week-old B57CL6 mice on right flank on day 0. All groups contained 10 mice. The inventors used the different plasmids containing either Luciferase (Luc), endostatin (Endo), cytosine deaminase (CD) and endostatin-CD (endo-CD), antiangiogenic deletion mutant of tumstatin (tum5), interleukin-12 (IL-12), or Tum5-IL12 fusion gene to transfect the B16F10 melanoma cells. After transfection, these melanoma cells were harvested and injected into the left flank of the mice in a different group on day 1. This procedure was repeated 3 more times on day 4, 7, 10. Distant tumors on the right flank were measured, and the volume was calculated and plotted over the treatment period.

Stable clones: B16-F10 melanoma cells ($2\times10^5$) were injected subcutaneously into 7-9-week-old B57CL6 mice on the right flank. Two days after, $2\times10^5$ of endostatin, IL12 or endo-IL12 expressing stable clones of B16F10 cancer cells were injected subcutaneously on the left flank. The stable clone cancer cells were repeat injected twice a week. The size of distant tumor on the right flank was measured every two days.

Example 10

Superior Anticancer Effect of Fusion Proteins Against Distant Tumor

Figure 8:
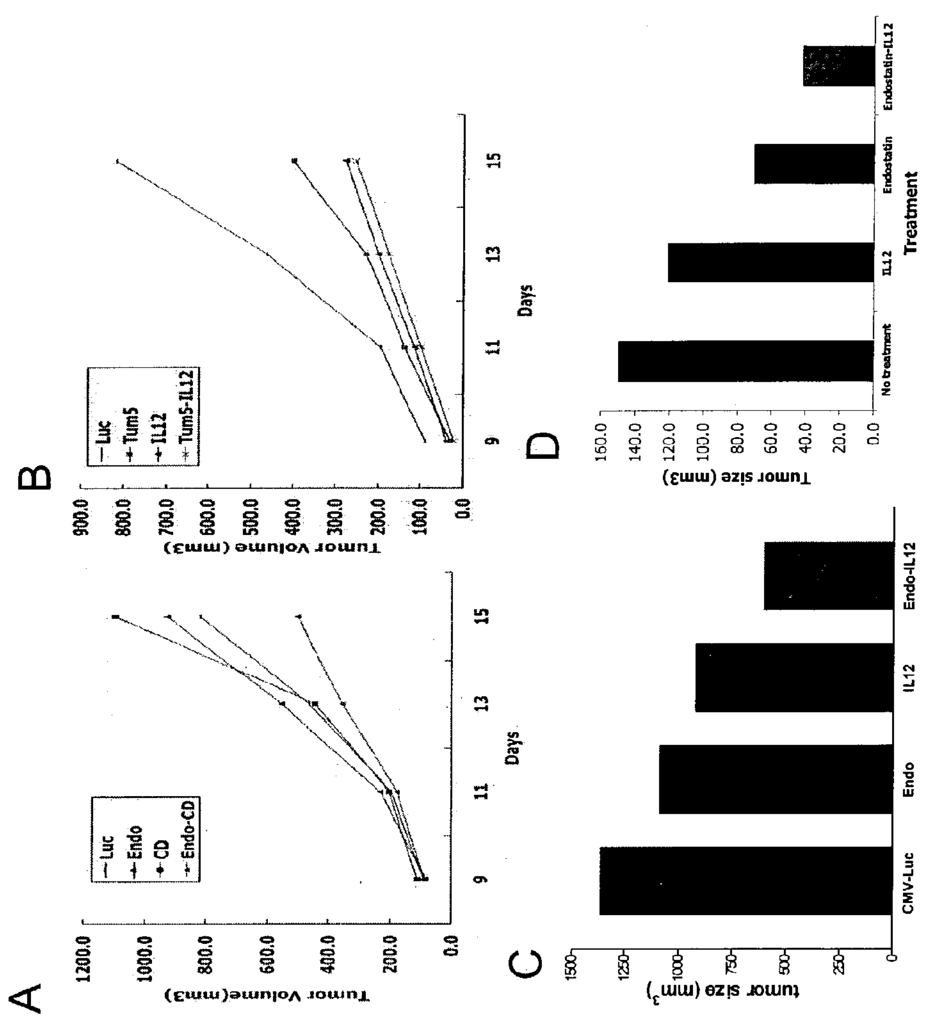
FIGS. 8A through 8D show superior anticancer effect on distant tumor of fusion proteins expressed by either stable clones or ex vivo transfection.

FIG. 8 demonstrates a superior anticancer effect on distant tumor of fusion proteins expressed by either stable clones or ex vivo transfection. In FIG. 8A, ex vivo treatment of endostatin-CD fusion gene of antiangio-chemotherapy showed better inhibitory effect on contra-lateral tumor growth. (Endo: endostatin; CD: cytosine deaminase; Endo-CD: fusion gene). FIG. 8B shows that ex vivo treatment of Tum5-IL12 fusion gene of antiangio-immunotherapy showed better tumor inhibitory effect on distant tumor (Tum5: tumstatin antiangiogenic deletion mutant, IL12: interleukin-12, Tum5-IL12: fusion gene). FIG. 8C provides that distant CT26 colon cancer growths were most significantly inhibited by Endo-IL12 gene therapy. Various genes were injected into CT26 tumor sites distant from the measured tumors, which were not treated with direct injection of genes. FIG. 8D shows stable line treatment of endostatin-IL12 against distant tumor. Endo-IL12 showed better anti-cancer effect than other therapeutic proteins.

Example 11

Significance of the Results

The results demonstrated above show that antiangiogenic fusion genes are useful as gene therapy and diagnostic reagents, as evidenced by results from studies provided herein. In FIG. 1, the fusion gene could lead to expression of fusion proteins, which were detected by immunoblotting and ELISA. As shown in FIG. 2 and FIG. 3, the fusion proteins are functional and possess both antiangiogenic properties as well as the functions attributable at least in part to the attached proteins. In these functional assays, fusion protein Endostatin-CD, for example, could inhibit angiogenesis to a similar extent of wild type Endostatin, as shown by endothelial tube formation and migration assays. In addition, the therapeutic/diagnostic proteins attached to the exemplary endostatin still functions as in their wild type form. Endostatin-GFP exhibits green fluorescence. Endostatin-GM-CSF could induce proliferation of NSF60 cells, whose growth is GM-CSF dependent. Endostatin-CD could convert non-toxic 5-FC to toxic 5-FU, thereby killing both 293T and HUVEC (human umbilical vascular endothelial cell) cells.

In both in vitro (FIG. 4) and pathological studies (FIG. 5), Endostatin-GFP is shown to be endothelial cell-specific. In FIG. 4, only endothelial cells (SVEC) exhibit GFP signal when incubated with conditional medium containing Endostatin-GFP. In FIG. 5, Endostatin-GFP is able to travel from Endostatin-GFP stable clone tumor (FIG. 5A) to distant parental B16-F10 melanoma cells. Endostatin-GFP is detected by anti-GFP antibody (FIG. 5B). In contrast, when B16-F10 tumor-bearing mice were not inoculated with Endostatin-GFP stable clone tumor, the parental cells did not show GFP signal (FIG. 5C). In other words, the endostatin component of the fusion protein Endostatin-GFP could lead GFP protein to the distant tumor blood vessel sites. Thus, the use of antiangiogenic proteins (endostatin, in this exemplary case) to deliver otherwise non-tumor blood vessel-specific proteins (such as, for example, GFP) to the tumor site is demonstrated. In addition, Endostatin-GFP serves as a diagnostic tool in other embodiments, since fluorescent signal emitted by GFP could be detected, and endostatin could target new blood vessels of tumor.

Lastly, the fusion genes as well as encoded fusion proteins are useful as therapeutic reagents. The inventors have used fusion genes, for example Endostatin-IL12, showing superior anticancer effects than either endostatin or IL12 alone, to treat both melanoma- (FIG. 7A and FIG. 7B) and colon cancer-bearing (FIG. 7C) mice. The fusion proteins encoded by these genes are also effective as protein therapeutic reagents as shown in another animal study (FIG. 8), where tumor cells ex vivo treated with (FIG. 8A and FIG. 8B), or established tumor injected with fusion genes (FIG. 8C), or stable clones (FIG. 8D) served as a "protein factory" and the secreted proteins were able to inhibit distant tumor growth.

Example 12

Ex vivo Testing of an Angiogenesis Inhibitor Coupled to a Therapeutic or Diagnostic Agent One useful biological property for an anti-cancer therapeutic is its ability to reduce tumorigenicity in vivo. To test the possibly, in some embodiments, anti-tumor activity of an angiogenesis inhibitor coupled to a therapeutic or diagnostic agent not utilized in studies provided herein may be demonstrated. For example, an ex vivo tumorigenicity assay may be performed in a nude mice cancer model. As exemplary cancer cell lines, human breast cancer cell lines MCF-7 and prostate cancer cell line PC-3 may be transfected with a fusion gene delivered by SN liposome in culture plates. Twenty-four hours later, the treated cells may be carefully harvested and inoculated into the mammary fat pads (mfp) (for MCF-7) or subcutaneous connective tissue (for PC-3) of nude mice. For example, four million cells may be inoculated for MCF-7 and one million cells for PC-3. Empty vector pcDNA3-transfected cells can be used as a control. The inoculated tumor size may be measured weekly.

This "ex vivo test" bypasses the gene delivery problems in vivo and shows that under the optimal gene delivery condition, tumor cells with fusion genes with antiangiogenic properties may have less tumor growth ability than controls.

Example 13

In vivo Testing of Angiogenesis Inhibitor Coupled to a Therapeutic or Diagnostic Agent In some embodiments, an angiogenesis inhibitor coupled to a therapeutic or diagnostic agent, such as an antiangiogenic fusion gene product, described herein or prepared by those of skill in the art based on the teachings provided herein, is used in the following in vivo study. Mice with established tumors are treated with the angiogenesis inhibitor coupled to a therapeutic or diagnostic agent, such as by injection, and shown to provide inhibition of tumor growth in mice compared with proper controls.

A systemic gene therapy approach for breast cancer may be utilized, consisting of, for example, a nonviral gene delivery system (SN) and a fusion gene. The SN-fusion gene may be systemically administered and shown to inhibit the growth and metastasis of, for example, human breast cancer cells implanted in nude mice and, in some embodiments, prolongs the life span of the treated animals.

Obviously, methods disclosed herein have proven useful for specific fusion genes in the context of the invention. Following the teachings provided herein, one of skill in the art can prepare and test any number of fusion genes for anti-angiogenesis activity, anti-cell proliferative activity, antitumor activity, pro-apoptotic activity, or a combination thereof.

Example 14

Testing of Exemplary Angiogenesis Inhibitor Coupled to a Therapeutic or Diagnostic Agent An angiogenesis inhibitor coupled to a therapeutic or diagnostic agent as it relates to anti-tumor activity is tested in an animal study, such as cell lines, cell culture, and/or models in addition to or other than those described in the preceding Examples. In general embodiments of the present invention, fusion genes, for example, are delivered by a vector, such as a liposome, adenoviral vector, or combination thereof, into nude mice models for their anti-tumor activity. Once the anti-tumor activity is demonstrated, potential toxicity is further examined using immunocompetent mice, followed by clinical trials.

In a specific embodiment, the preferential growth inhibitory activity of antiangiogenic fusion genes is tested in at least one animal. Briefly, and for example, cancer cell lines are administered into mammary fat-pad of nude mice to generate a breast xenografted model. Any cancer cell is within the scope of the present invention irrespective of its genotype or expression levels (such as, for example, whether it is HER-2/neu-positive or HER-2/neu-negative). In a specific embodiment, HER-2/neu overexpressing breast cancer cell lines (such as, for example, SKBR3 and/or MDA-MB361) are utilized, such as for testing. After the tumors reach a particular size, the fusion gene and, in some embodiments, the control, is administered into the mouse, such as, for example, intravenously injected in an admixture with an acceptable carrier, such as liposomes. The tumor sizes and survival curve from these treatments are compared and statistically analyzed.

In some embodiments of the present invention, a mouse animal model is utilized to study targeting anti-angiogenic fusion gene products. In one specific embodiment, a bilateral melanoma or colon tumor model is utilized. In another embodiment, a one-sided intratumoral gene therapy protocol is utilized. In another embodiment, wherein a suicide therapeutic gene is utilized in the targeting fusion polypeptide, the model is administered intraperitoneally a prodrug (such as, for example, 5FC) following delivery of the suicide therapeutic gene. In some embodiments, contralateral tumor size is evaluated for a tumor targeting effect. In addition to suicide gene therapy using, for example, endostatin-cytosine deaminase with 5-FC administered as a prodrug, similar approaches are also used for endostatin-IL12. Ipsilateral tumor size may also be evaluated for chemotherapy effect, in some embodiments.

Example 15

Preparation of Additional Angiogenesis Inhibitors Coupled to a Therapeutic or Diagnostic Agent Based on the data in previous Examples and the teachings elsewhere in the specification, in addition to the knowledge in the art, a skilled artisan would be motivated and capable of generating an additional fusion angiogenesis inhibitor coupled to a therapeutic or diagnostic agent and, furthermore, would be able to determine the usefulness in the context of the invention using methodology disclosed herein.

Example 16

Testing of Additional Angiogenesis Inhibitors Coupled to a Therapeutic or Diagnostic Agent Once an angiogenesis inhibitor coupled to a therapeutic or diagnostic agent other than the exemplary embodiments disclosed herein is created, testing using a cell culture in a relevant cell line(s) may be performed, such as described herein. Furthermore, testing of, for example, the antiangiogenic fusion gene products may be performed, such as by using FACS analysis. Also, testing of the additional antiangiogenic fusion gene products using ex vivo systems or in vivo systems as described herein may be employed, in specific embodiments.

Example 17

Clinical Trials

This example is concerned with the development of human treatment protocols using the angiogenesis inhibitor coupled to a therapeutic or diagnostic agents. In specific embodiments, the angiogenesis inhibitor coupled to a therapeutic or diagnostic agent is an antiangiogenic fusion gene product including protein, peptide, or polypeptide or a nucleic acid encoding the antiangiogenic fusion protein, peptide, or polypeptides, alone or in combination with other drugs. In a specific embodiment, the other drugs are also useful for treatment of angiogenesis, such as for tumor inhibition. In a specific embodiment, the drug is useful for treating cancer. The antiangiogenic fusion protein, peptide, or polypeptide or a nucleic acid encoding the antiangiogenic fusion protein, peptide, or polypeptides, and anti-cancer drug treatment will be of use in the clinical treatment of various cancers. Such treatment will be particularly useful tools in anti-tumor therapy, for example, in treating patients with ovarian, breast, prostate, pancreatic, brain, colon, and lung cancers that are resistant to conventional chemotherapeutic regimens.

The various elements of conducting a clinical trial, including patient treatment and monitoring, will be known to those of skill in the art in light of the present disclosure. The following information is being presented as a general guideline for use in establishing the antiangiogenic fusion protein, peptide, or polypeptide or a nucleic acid encoding the antiangiogenic fusion protein, peptide, or polypeptides, in clinical trials.

Patients with advanced, metastatic breast, epithelial ovarian carcinoma, pancreatic, colon, or other cancers chosen for clinical study will typically be at high risk for developing the cancer, will have been treated previously for the cancer which is presently in remission, or will have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.In regard to the antiangiogenic fusion protein, peptide, or polypeptide or a nucleic acid encoding the antiangiogenic fusion protein, peptide, or polypeptides, and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, PSA, p38 (phosphorylated and un-phosphorylated forms), Akt (phosphorylated and un-phosphorylated forms) and in the cells (antiangiogenic fusion proteins, peptides or polypeptides or nucleic acids encoding the same) may be assessed and recorded.

In the same procedure, the antiangiogenic fusion protein, peptide, or polypeptide or a nucleic acid encoding the antiangiogenic fusion protein, peptide, or polypeptides, may be administered alone or in combination with the other anticancer drug. The administration may be in the pleural/peritoneal cavity, directly into the tumor, or in a systemic manner. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of the antiangiogenic fusion protein, peptide, or polypeptide or a nucleic acid encoding the antiangiogenic fusion protein, peptide, or polypeptides, and the lot of anti-cancer drug exceed 5 EU/kg for any given patient.

The antiangiogenic fusion protein, peptide, or polypeptide or a nucleic acid encoding the antiangiogenic fusion protein, peptide, or polypeptides, and/or the other anti-cancer drug combination, may be administered over a short infusion time or at a steady rate of infusion over a 7 to 21 day period. The antiangiogenic fusion protein, peptide, or polypeptide or a nucleic acid encoding the antiangiogenic fusion protein, peptide, or polypeptides, infusion may be administered alone or in combination with the anti-cancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of the antiangiogenic fusion protein, peptide, or polypeptide or a nucleic acid encoding the mutant protein, peptide, or polypeptides, in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p38 (phosphorylated and non-phopshorylated forms) and Akt (phosphorylated and non-phosphorylated forms), p185, etc.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, ki67 and Tunel assay to measure apoptosis, Akt) and in the cells (Akt) may be assessed. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS

U.S. Pat. No. 4,683,202
U.S. Pat. No. 4,797,368
U.S. Pat. No. 4,879,236
U.S. Pat. No. 5,139,941
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,641,484
U.S. Pat. No. 5,670,488
U.S. Pat. No. 5,789,166
U.S. Pat. No. 5,798,208
U.S. Pat. No. 5,830,650
U.S. Pat. No. 5,871,986
U.S. Pat. No. 5,925,565
U.S. Pat. No. 5,928,906
U.S. Pat. No. 5,935,819
PCT International Application WO 99/16889

PUBLICATIONS

Folkman, Semin. Oncol., 28(6):536-542, 2001.
Brem, Cancer Control, 6(5):436-458, 1999.
Ferrara and Alitalo, Nat. Med., 5(12):1359-1364, 1999.
Keshet and Ben-Sasson, J. Clin. Invest., 104(11):1497-1501, 1999.
Carmeliet and Jain, Nature, 407(6801):249-257, 2000.
Folkman, N. Engl. J. Med., 285(21):1182-1186, 1971.
Kerbel, J. Clin. Oncol., 19(18):45S-51S, 2001.
Risau, Circ. Res., 82(8):926-928, 1998.
Klohs and Hamby, Curr. Opin. Biotechnol., 10(6):544-549, 1999.
Rosen, Oncologist, 5(1):20-27, 2000.
Burke and DeNardo, Crit. Rev. Oncol. Hematol., 39(1-2):155-171, 2001.
Taraboletti and Margosio, Curr. Opin. Pharmacol., 1(4):378-384, 2001.
Glaspy, Semin. Oncol., 29(7):41-46, 2002.
Boehm, Nature, 390(6658):404-407, 1997.
Thomas et al., J. Clin. Oncol., 21(2):223-231, 2003.
Herbst et al., J. Clin. Oncol., 20(18):3792-3803, 2002.
Eder et al., J. Clin. Oncol., 20(18):3772-3784, 2002.
Beecken Kramer, and Jonas, J. Cell Mol. Med., 4(4):262-269, 2000.
Bouma-ter Steege et al., Crit. Rev. Eukaryot. Gene Expr., 11 (4):319-334, 2001.
Cao, Prog. Mol. Subcell. Biol., 20:161-176, 1998.
Cao, Int. J. Biochem. Cell Biol., 33(4):357-369, 2001.
Folkman, Semin. Oncol., 29(6:16):15-18, 2002.
Kirsch et al., Neurooncol., 50(1-2): 173-180, 2000.
Ryan and Wilding, Drugs Aging, 17(4):249-255, 2000.
Reed, Nat. Rev. Drug Discov., 1(2):111-121, 2002.
Baliga and Kumar, Hematol. Oncol., 20(2):63-74, 2002.
Chao and Korsmeyer, Annu. Rev. Immunol., 16:395-419, 1998.
Trinchieri, Nat. Rev. Immunol., 3(2):133-146, 2003.
Leonard et al., Blood, 90(7):2541-2548, 1997.
Yang et al., Cancer Biother. Radiopharm., 17(2):233-245, 2002.
Halin et al., Nat. Biotechnol., 20(3):264-269, 2002.
Carnemolla et al., Blood, 99(5):1659-1665, 2002.
Scappaticci et al., Angiogenesis, 4(4):263-268, 2001.
Veenendaal et al., 99(12):7866-7871, 2002.
Arora et al., Cancer Res., 59(1):183-188, 1999.
Hotz et al., J. Gastrointest. Surg., 6(2):159-166, 2002.
Huang et al., Science, 275(5299):547-550, 1997.
Kreitman, Curr. Opin. Immunol., 11(5):570-578, 1999.
Penichet and Morrison, J. Immunol. Methods, 248(1-2):91-101, 2001.
Lode et al., Proc. Natl. Acad. Sci. USA, 96(4):1591-1596, 1999.
Ruehlmann et al., Cancer Res., 61(23):8498-8503, 2001.
Dreier et al., Bioconjug. Chem., 9(4):482-489, 1998.
Niethammer et al., Cancer Res., 61(16):6178-6184, 2001.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method comprising contacting intratumorally a cancer cell in a tumor of a subject with an expression vector comprising a nucleic acid encoding a polypeptide comprising an endostatin polypeptide linked to a cytosine deaminase polypeptide, said method further comprising providing 5-fluorocytosine to the subject, wherein expression of the polypeptide results in inhibition of tumor growth.

2. The method of claim 1, wherein the subject is a human.

3. The method of claim 1, wherein the cancer cell is from head and neck cancer, ovarian cancer, thyroid cancer, oral cancer, prostate cancer, melanoma, colon cancer, breast cancer, angioma, sarcoma, lung cancer, brain cancer, pancreatic cancer, liver cancer, bladder cancer, or gastrointestinal cancer.

4. The method of claim 1, wherein the nucleic acid is comprised in a plasmid, a retroviral vector, an adenoviral vector, an adeno-associated viral vector, or a liposome.

5. The method of claim 1, wherein the nucleic acid is dispersed in a pharmacologically acceptable excipient.

6. A method of inhibiting a tumor comprising intratumorally administering to a subject having a tumor autologous tumor cells transfected with an expression vector comprising a nucleic acid encoding a polypeptide comprising an endostatin polypeptide linked to cytosine deaminase, said method further comprising providing 5-fluorocytosine to the subject, wherein expression of the polypeptide results in inhibition of tumor growth.

7. A method comprising administering to a subject having a tumor autologous tumor cells transfected with an expression vector comprising nucleic acid encoding a polypeptide comprising an endostatin polypeptide linked to a cytosine deaminase polypeptide, said method further comprising providing 5-fluorocytosine to the subject, wherein expression of the polypeptide results in inhibition of tumor growth.

8. A method comprising contacting a cancer cell in a tumor of a subject with an expression vector comprising a nucleic acid encoding a polypeptide comprising an endostatin polypeptide linked to cytosine deaminase, said method further comprising providing 5-fluorocytosine to the subject, wherein expression of the polypeptide results in inhibition of tumor growth, wherein the vector is administered to the subject intravenously or subcutaneously in a nucleic acid/liposomal complex.

* * * * *

SEQUENCE LISTING

<160> NUMBER OF SEQ ID NOS: 42

<210> SEQ ID NO 1
<211> LENGTH: 1606
<212> TYPE: DNA
<213> ORGANISM: Herpes Simplex Virus

<400> SEQUENCE: 1

```
aggagcttca gggagtggcg cagctgcttc atccccgtgg cccgttgctc gcgtttgctg      60

gcggtgtccc cggaagaaat atatttgcat gtctttagtt ctatgatgac acaaaccccg     120

cccagcgtct tgtcattggc gaattcgaac acgcagatgc agtcggggcg gcgcggtccc     180

aggtccactt cgcatattaa ggtgacgcgt gtggcctcga acaccgagcg accctgcagc     240

gacccgctta acagcgtcaa cagcgtgccg cagatcttgg tggcgtgaaa ctcccgcacc     300

tctttggcaa gcgccttgta gaagcgcgta tggcttcgta cccctgccat caacacgcgt     360

ctgcgttcga ccaggctgcg cgttctcgcg gccatagcaa ccgacgtacg gcgttgcgcc     420

ctcgccggca gcaagaagcc acggaagtcc gcctggagta gaaaatgccc acgctactgc     480

gggtttatat agacggtcct cacgggatgg ggaaaaccac caccacgcaa ctgctggtgg     540

ccctgggttc gcgcgacgat atcgtctacg tacccgagcc gatgacttac tggcaggtgc     600

tgggggcttc cgagacaatc gcgaacatct acaccacaca acaccgcctc gaccagggtg     660

agatatcggc cggggacgcg gcggtggtaa tgacaagcgc ccagataaca atgggcatgc     720

cttatgccgt gaccgacgcc gttctggctc ctcatatcgg gggggaggct gggagctcac     780

atgccccgcc cccggccctc accctcatct tcgaccgcca tcccatcgcc gccctcctgt     840

gctacccggc cacgcgatac cttatgggca gcatgacccc ccaggccgtg ctggcgttcg     900

tggccctcat cccgccgacc ttgcccggca caaacatcgt gttgggggcc cttccggagg     960

acagacacat cgaccgcctg gccaaacgcc agcgccccgg cgagcggctt gacctggcta    1020

tgttggccgc gattcgccgc gtttacgggc tgcttgccaa tacggtgcgg tatctgcagg    1080

gcggcgggtc gtggcgggag gattggggac agctttcggg gacggccgtg ccgccccagg    1140

gtgccgagcc ccagagcaac gcgggcccac gaccccatat cggggacacg ttatttaccc    1200

tgtttcgggc ccccgagttg ctggccccca acggcgacct gtataacgtg tttgcctggg    1260

ccttggacgt cttggccaaa cgcctccgtc ccatgcacgt ctttatcctg gattacgacc    1320

aatcgcccgc cggctgccgg gacgccctgc tgcaacttac ctccgggatg gtccagaccc    1380

acgtcaccac cccaggctcc ataccgacga tctgcgacct ggcgcgcatg tttgcccggg    1440

agatggggga ggctaactga aacacggaag gagacaatac cggaaggaac ccgcgctatg    1500

acggaaataa aaagacagaa taaaacgcac gggtgttggg tcgtttgttc ataaacgcgg    1560

ggttcggtcc cagggctggc actctgtcga taccccaccg agaccc                   1606
```

<210> SEQ ID NO 2
<211> LENGTH: 1659
<212> TYPE: DNA
<213> ORGANISM: Herpes Simplex Virus

<400> SEQUENCE: 2

```
ctgcagcagc ttcagggagt ggcgcagctg cttcatgccc gtggtccgct gttcgcgttt      60

gctggccgtg tccccggaag aaatcgattt gcatgtcttt agctccagga tgacgcacac     120

acctcccaac gttttgtcat tggcgaattc gaacacgcag atgcagtctg ggcggcgcgg     180
```

```
cccgaggtcc acttcgcata ttaaggtgac gcgcgtggcc tcgaacagcg agcgaccctg    240

cagcgacccg ctcatcagcg tcagagcgtt ccacaaatcc tggtggcgtt gaactcccgc    300

acctctcggg cgaacgcctt gtagaagcgg gtatggcttc tcacgccggc caacagcacg    360

cgcctgcgtt cggtcaggct gctcgtgcga gcgggcctac cgacggccgc gcggcgtccc    420

gtcctagcca tcgccagggg gcctccgaag cccgcgggga tccggagctg cccacgctgc    480

tgcgggttta tatagacgga ccccacgggg tggggaagac caccacctcc gcgcagctga    540

tggaggccct ggggccgcgc gacaatatcg tctacgtccc cgagccgatg acttactggc    600

aggtgctggg ggcctccgag accctgacga acatctacaa cacgcagcac cgtctggacc    660

gcggcgagat atcggccggg gaggcggcgg tggtaatgac cagcgcccag ataacaatga    720

gcacgcctta tgcggcgacg gacgccgttt tggctcctca tatcgggggg gaggctgtgg    780

gcccgcaagc cccgcccccg gccctcaccc ttgttttcga ccggcaccct atcgcctccc    840

tgctgtgcta cccggccgcg cggtacctca tgggaagcat gaccccccag gccgtgttgg    900

cgttcgtggc cctcatgccc ccgaccgcgc ccggcacgaa cctggtcctg ggtgtccttc    960

cggaggccga acacgccgac cgcctggcca gacgccaaca cccgggcgag cggcttgacc   1020

tggccatgct gtccgccatt cgccgtgtct acgatctact cgccaacacg gtgcggtacc   1080

tgcagcgcgg cgggaggtgg cgggaggact ggggccggct gacgggggtc gccgcggcga   1140

ccccgcgccc cgaccccgag gacggcgcgg ggtctctgcc ccgcatcgag gacacgctgt   1200

ttgccctgtt ccgcgttccc gagctgctgg cccccaacgg ggacttgtac cacatttttg   1260

cctgggtctt ggacgtcttg gccgaccgcc tccttccgat gcatctattt gtcctggatt   1320

acgatcagtc gcccgtcggg tgtcgagacg ccctgttgcg cctcaccgcc gggatgatcc   1380

caacccgcgt cacaaccgcc gggtccatcg ccgagatacg cgacctggcg cgcacgtttg   1440

cccgcgaggt ggggggagtt tagttcaaac acggaagccc gaacggaagg cctcccggcg   1500

atgacggcaa taaaagaaca gaataaaagg cattgttgtc gtgtggtgtg tccataagcg   1560

cgggggttcg gggccagggc tggcaccgta tcagcacccc accgaaaaac ggagcgggcc   1620

gatccgacct tgttttcggc tctgtactcc ttgtgcttt                          1659
```

<210> SEQ ID NO 3
<211> LENGTH: 1524
<212> TYPE: DNA
<213> ORGANISM: Varicella zoster
<220> FEATURE:
<221> NAME/KEY: modified_base
<222> LOCATION: (1199)
<223> OTHER INFORMATION: n = a, c, g, t/u

<400> SEQUENCE: 3

```
ctggcgcata ccctcgcaaa actggtgata cttagtaggg gtatgtatat tagcgctaaa     60

acggcaagat tttaattcca ctataaaaca aacggtcttt ccggcaccac tggattccgt    120

ttgtataata caaacacaat cggggcgtcg gcgtcccaaa tttacttcaa acgacattga    180

tatgcgtaca gccctttgaa catccacgtg ggataacggc gacaggagtt ttgccagcct    240

cgggttgaac gcgtccgcga aacctcgacg tacgttatca atatcctttt tgagtacatc    300

gtaaaaacga gtgtggcaac gttgtcccaa acgaaaacac ttggcccgaa ttcgactagc    360

ggacatattt gaagttccgt cccagaagat aacctaagac gcgtttgtct acaataaaca    420

tgtcaacgga taaaaccgat gtaaaaatgg gcgttttgcg tatttatttg gacggggcgt    480
```

-continued

```
atggaattgg aaaaacaacc gccgccgaag aatttttaca ccactttgca ataacaccaa    540

accggatctt actcattggg gagcccctgt cgtattggcg taaccttgca ggggaggacg    600

ctatttgcgg aatttacgga acacaaactc gccgtcttaa tggagacgtt tcgcctgaag    660

acgcacaacg cctcacggct cattttcaga gcctgttctg ttctccgcat gcaattatgc    720

atgcgaaaat ctcggcattg atggacacaa gtacatcgga tctcgtacaa gtaaataagg    780

agccgtataa aattatgtta tccgaccgac acccaatcgc ctcaactata tgttttccct    840

tgtccagata cttagtggga gatatgtccc cagcggcgct tcctgggtta ttgtttacgc    900

ttcccgctga accccccggg accaacttgg tagtttgtac cgtttcactc cccagtcatt    960

tatccagagt aagcaaacgg gccagaccgg gagaaacggt taatctgccg tttgttatgg   1020

ttctgagaaa tgtatatata atgcttatta atacaattat atttcttaaa actaacaact   1080

ggcacgcggg ctggaacaca ctgtcatttt gtaatgatgt atttaaacag aaattacaaa   1140

aatccgagtg tataaaacta cgcgaagtac ctgggattga agacacgtta ttcgccgtnc   1200

ttaaacttcc ggagctttgc ggagagtttg gaaatattct gccgttatgg gcatggggaa   1260

tggagaccct ttcaaactgc ttacgaagca tgtctccgtt cgtattatcg ttagaacaga   1320

caccccagca tgcggcacaa gaactaaaaa ctctgctacc ccagatgacc ccggcaaaca   1380

tgtcctccgg tgcatggaat atattgaaag agcttgttaa tgccgttcag gacaacactt   1440

cctaaatata cctagtattt acgtatgtac cagtaaaaag atgatacaca ttgtcatact   1500

cgcgtgtacg tgtttttctt tttt                                          1524
```

<210> SEQ ID NO 4
<211> LENGTH: 1634
<212> TYPE: DNA
<213> ORGANISM: Escherichia coli

<400> SEQUENCE: 4

```
ctgcaggcca ctggttaccg ggaattgttc cggtcaacgc ggtattaggt ggcgcgctga     60

gctatctgat ccttaacccg attttgaatc gtaaaacgac agcagcaatg acgcatgtgg    120

aggctaacag tgtcgaataa cgctttacaa acaattatta acgcccggtt accaggcgaa    180

gaggggctgt ggcagattca tctgcaggac ggaaaaatca gcgccattga tgcgcaatcc    240

ggcgtgatgc ccataactga aaacagcctg gatgccgaac aaggtttagt tataccgccg    300

tttgtggagc cacatattca cctggacacc acgcaaaccg ccggacaacc gaactggaat    360

cagtccggca cgctgtttga aggcattgaa cgctgggccg agcgcaaagc gttattaacc    420

catgacgatg tgaaacaacg cgcatggcaa acgctgaaat ggcagattgc caacggcatt    480

cagcatgtgc gtacccatgt cgatgtttcg gatgcaacgc taactgcgct gaaagcaatg    540

ctggaagtga agcaggaagt cgcgccgtgg attgatctgc aaatcgtcgc cttccctcag    600

gaagggattt tgtcgtatcc caacggtgaa gcgttgctgg aagaggcgtt acgcttaggg    660

gcagatgtag tgggggcgat tccgcatttt gaatttaccc gtgaatacgg cgtggagtcg    720

ctgcataaaa ccttcgccct ggcgcaaaaa tacgaccgtc tcatcgacgt tcactgtgat    780

gagatcgatg acgagcagtc gcgctttgtc gaaaccgttg ctgccctggc gcaccatgaa    840

ggcatgggcg cgcgagtcac cgccagccac accacggcaa tgcactccta taacggggcg    900

tatacctcac gcctgttccg cttgctgaaa atgtccggta ttaactttgt cgccaacccg    960

ctggtcaata ttcatctgca aggacgtttc gatacgtatc caaaacgtcg cggcatcacg   1020

cgcgttaaag agatgctgga gtccggcatt aacgtctgct ttggtcacga tgatgtcttc   1080
```

```
gatccgtggt atccgctggg aacggcgaat atgctgcaag tgctgcatat ggggctgcat   1140

gtttgccagt tgatgggcta cgggcagatt aacgatggcc tgaatttaat cacccaccac   1200

agcgcaagga cgttgaattt gcaggattac ggcattgccg ccggaaacag cgccaacctg   1260

attatcctgc cggctgaaaa tgggtttgat gcgctgcgcc gtcaggttcc ggtacgttat   1320

tcggtacgtg gcggcaaggt gattgccagc acacaaccgg cacaaaccac cgtatatctg   1380

gagcagccag aagccatcga ttacaaacgt tgaacgactg ggttacagcg agcttagttt   1440

atgccggatg cggcgtgaac gccttatccg gcctacgtag agcactgaac tcgtaggcct   1500

gataagcgta gcgcatcagg caattccagc cgctgatctg tgtcagcggc taccgtgatt   1560

cattcccgcc aacaaccgcg cattcctcca acgccatgtg caaaaatgcc ttcgcagcgg   1620

ctgtctgcca gctg                                                       1634
```

<210> SEQ ID NO 5
<211> LENGTH: 2457
<212> TYPE: DNA
<213> ORGANISM: Mus musculus

<400> SEQUENCE: 5

```
cgcgcggtgt gtgatctggt cggtaccgag gagcgcaggt tgtgtcacca acatgggggga     60

ctctcacgaa gacaccagtg ccacagtgcc tgaggcagtg gctgaagaag tgtctctatt    120

cagcacaacg gacattgttc tgttttctct catcgtgggg gtcctgacct actggttcat    180

ctttaaaaag aagaaagaag agataccgga gttcagcaag atccagacaa cggccccacc    240

tgtcaaagag agcagcttcg tggaaaagat gaagaaaacg ggaaggaaca ttattgtatt    300

ctatggctcc cagacgggaa ccgcggagga gtttgccaac cggctgtcca aggatgccca    360

ccgctatggg atgcggggca tgtctgcaga ccctgaagag tatgacttgg ccgacctgag    420

cagcctgcct gagatcgaca agtccctggt agtcttctgc atggccacat acggagaagg    480

cgaccccacc gacaacgcgc aggacttcta tgattggctg caggagactg acgtggacct    540

cacgggtgtc aagtttgctg tgtttggtct cgggaacaag acctatgagc acttcaacgc    600

catgggcaag tatgtggacc agcggctgga gcagcttggc gcccagcgaa tctttgagtt    660

gggccttggt gatgacgacg ggaacttgga agaggatttc atcacatgga gggagcagtt    720

ctggccagct gtgtgcgagt tcttcggggt ggaagccact ggggaggagt cgagcatccg    780

ccagtacgag ctcgtggtcc acgaagacat ggacacagcc aaggtgtaca cgggtgagat    840

gggccgtctg aagagctacg agaaccagaa acccccccttc gatgccaaga atccattcct    900

ggctgctgtc accacgaacc ggaagctgaa ccaaggcact gagaggcatc taatgcacct    960

ggaattggac atctcagact ccaagatcag gtatgaatct ggagatcacg tggctgtgta   1020

cccagccaac gactccaccc tggtcaacca gattggggag atcctggggg ctgacctgga   1080

tgtcatcatg tctctaaaca atctcgatga ggagtcgaat aagaagcatc cgttcccctg   1140

ccccaccacc taccgcacgg ccctcaccta ctacctggac atcactaacc cgccacgaac   1200

caacgtgctc tacgagctgg cccagtacgc ctcagagccc tcggagcagg aacacctgca   1260

caagatggcg tcctcctccg gcgagggcaa ggagctgtac ctgagctggg tggtggaggc   1320

ccggaggcac atcctagcca ttctccaaga ctacccgtcc ctgcggccac ccatcgacca   1380

cctgtgcgag ctcctcccga ggctgcaggc ccgctactat tccattgcct cgtcgtctaa   1440

ggtccacccc aactccgtgc acatctgcgc cgtggctgtg gagtatgaag cgaagtctgg   1500
```

-continued

```
acgagtgaac aagggggtgg ccaccagctg gcttcggacc aaggaaccag caggagagaa   1560
tggccgccgg gccctggtcc ccatgttcgt ccgcaagtcc cagttccgct tgcctttcaa   1620
gcccaccaca cctgttatca tggtgggccc cggcactggg gttgcccctt tcatgggctt   1680
catccaggag cgggcttggc ttcgagagca aggcaaggag gtcggagaga cgctgctcta   1740
ctacggctgc cggcgctcgg atgaggacta tctgtaccgc gaggagctgg cgcgcttcca   1800
caaggacggc gccctcacgc agcttaatgt ggccttttcc cgtgagcagg cccacaaggt   1860
ctatgttcag cacctgctca agagggacaa agagcacctg tggaagctga tccacgaagg   1920
tggtgcccac atctatgtct gcggggatgc tcgaaatatg gccaaagatg tgcagaacac   1980
attctatgac atcgtggccg agtttgggcc catggagcac acccaggctg tggactatgt   2040
taagaagctc atgaccaagg gccgctactc gctggatgta tggagctagg agctgccgcc   2100
ccccacccct cgctccctgt aatcacgtcc ttaacttcct tctgccgacc tccacctctg   2160
gtggttcctg ccctgcctgg acacagggag gcccagggac tgactcctgg cctgagtgat   2220
gccctcctgg gcccttaggc agagcctggt ccattgtacc aggcagccta gcccagccca   2280
gggcacatgg caagagggac tggacccacc tttgggtgat gggtgcctta ggtccccagc   2340
agctgtacag aaggggctct tctctccaca gagctggggt gcagccccaa catgtgattt   2400
tgaatgagtg taaataattt taaataacct ggcccttgga ataaagttgt tttctgt      2457
```

<210> SEQ ID NO 6
<211> LENGTH: 2048
<212> TYPE: DNA
<213> ORGANISM: Pseudomonas

<400> SEQUENCE: 6

```
atcatggatc cacgcactga aggcgcgcgg caagacgcgc ggcgtggcga cgctgtgcat     60
cggcgggggc gaaggcaccg cagtggcact cgaattgcta taagaaccat ggctggggac    120
gcccgacaac aggcgtccac cagctttttt cattccgaca acccgaacga acaatgcgta    180
gagcaggaga ttccatgcgc ccatccatcc accgcacagc catcgccgcc gtgctggcca    240
ccgccttcgt ggcgggcacc gccctggccc agaagcgcga caacgtgctg ttccaggcag    300
ctaccgacga gcagccggcc gtgatcaaga cgctggagaa gctggtcaac atcgagaccg    360
gcaccggtga cgccgagggc atcgccgctg cgggcaactt cctcgaggcc gagctcaaga    420
acctcggctt cacggtcacg cgaagcaagt cggccggcct ggtggtgggc gacaacatcg    480
tgggcaagat caagggccgc ggcggcaaga acctgctgct gatgtcgcac atggacaccg    540
tctacctcaa gggcattctc gcgaaggccc cgttccgcgt cgaaggcgac aaggcctacg    600
gcccgggcat cgccgacgac aagggcggca acgcggtcat cctgcacacg ctcaagctgc    660
tgaaggaata cggcgtgcgc gactacggca ccatcaccgt gctgttcaac accgacgagg    720
aaaagggttc cttcggctcg cgcgacctga tccaggaaga agccaagctg gccgactacg    780
tgctctcctt cgagcccacc agcgcaggcg acgaaaaact ctcgctgggc acctcgggca    840
tcgcctacgt gcaggtcaac atcaccggca aggcctcgca tgccggcgcc gcgcccgagc    900
tgggcgtgaa cgcgctggtc gaggcttccg acctcgtgct gcgcacgatg aacatcgacg    960
acaaggcgaa gaacctgcgc ttcaactgga ccatcgccaa ggccggcaac gtctcgaaca   1020
tcatccccgc cagcgccacg ctgaacgccg acgtgcgcta cgcgcgcaac gaggacttcg   1080
acgccgccat gaagacgctg gaagagcgcg cgcagcagaa gaagctgccc gaggccgacg   1140
tgaaggtgat cgtcacgcgc ggccgcccgg ccttcaatgc cggcgaaggc ggcaagaagc   1200
```

-continued

```
tggtcgacaa ggcggtggcc tactacaagg aagccggcgg cacgctgggc gtggaagagc   1260
gcaccggcgg cggcaccgac gcggcctacg ccgcgctctc aggcaagcca gtgatcgaga   1320
gcctgggcct gccgggcttc ggctaccaca gcgacaaggc cgagtacgtg gacatcagcg   1380
cgattccgcg ccgcctgtac atggctgcgc gcctgatcat ggatctgggc gccggcaagt   1440
gaatgctgcc ccccggcttt tcactcgcgt tgctcgtgta actccacccc ccgaggggga   1500
ggcgcggtcc gccttggggc ggcccggcgg cgaccgcctc gtcacataga aggaactgcc   1560
atgttgttga cagcagacca ggaagccatc cgcgacgcgg tgcgcgactt ctcgcaagcc   1620
gaactctggc ccaacgccgc gaatggggac cgcgagcaca gctttcccaa gagcccacca   1680
ggccgtcggc tggcgtacgc agtctgcgtg cccgaggagc atggcggcgc cggcctcgac   1740
tacctcacct cgcgctggtg ctggaggaga tcgcggccgg cgacggcggc accagcaccg   1800
ccatcagcgt gaccaactgc cccgtcaacg ccatcctcat gcgctacggc aacgcgcagc   1860
agaagaagca gtggctcgag ccgctggcgc agggccggat gctcggcgcc ttctgcctga   1920
ccgagccgca ggccggcagc gatgcatcga gcctgcgcac cacggcgcgc aaggacggcg   1980
acggctacgt gatcgacggc gtgaagcagt tcatcaccag cggcaagaac ggccaggtgg   2040
cgggatcc                                                            2048
```

<210> SEQ ID NO 7
<211> LENGTH: 2191
<212> TYPE: DNA
<213> ORGANISM: Homo sapiens

<400> SEQUENCE: 7

```
ggtggccgag cgggggaccg ggaagcatgg cccgggggtc ggcggttgcc tgggcggcgc     60
tcgggccgtt gttgtggggc tgcgcgctgg ggctgcaggg cgggatgctg taccccccagg   120
agagcccgtc gcgggagtgc aaggagctgg acggcctctg gagcttccgc gccgacttct    180
ctgacaaccg acgccggggc ttcgaggagc agtggtaccg gcggccgctg tgggagtcag    240
gccccaccgt ggacatgcca gttccctcca gcttcaatga catcagccag gactggcgtc    300
tgcggcattt tgtcggctgg gtgtggtacg aacgggaggt gatcctgccg gagcgatgga    360
cccaggacct gcgcacaaga gtggtgctga ggattggcag tgcccattcc tatgccatcg    420
tgtgggtgaa tggggtcgac acgctagagc atgagggggg ctacctcccc ttcgaggccg    480
acatcagcaa cctggtccag gtggggcccc tgccctcccg gctccgaatc actatcgcca    540
tcaacaacac actcaccccc accaccctgc caccagggac catccaatac ctgactgaca    600
cctccaagta tcccaagggt tactttgtcc agaacacata ttttgacttt ttcaactacg    660
ctggactgca gcggtctgta cttctgtaca cgacacccac cacctacatc gatgacatca    720
ccgtcaccac cagcgtggag caagacagtg ggctggtgaa ttaccagatc tctgtcaagg    780
gcagtaacct gttcaagttg gaagtgcgtc ttttggatgc agaaaacaaa gtcgtggcga    840
atgggactgg gacccagggc caacttaagg tgccaggtgt cagcctctgg tggccgtacc    900
tgatgcacga acgccctgcc tatctgtatt cattggaggt gcagctgact gcacagacgt    960
cactggggcc tgtgtctgac ttctacacac tccctgtggg gatccgcact gtggctgtca   1020
ccaagagcca gttcctcatc aatgggaaac ctttctattt ccacggtgtc aacaagcatg   1080
aggatgcgga catccgaggg aagggcttcg actggccgct gctggtgaag gacttcaacc   1140
tgcttcgctg gcttggtgcc aacgctttcc gtaccagcca ctacccctat gcagaggaag   1200
```

-continued

```
tgatgcagat gtgtgaccgc tatgggattg tggtcatcga tgagtgtccc ggcgtgggcc   1260

tggcgctgcc gcagttcttc aacaacgttt ctctgcatca ccacatgcag gtgatggaag   1320

aagtggtgcg tagggacaag aaccaccccg cggtcgtgat gtggtctgtg gccaacgagc   1380

ctgcgtccca cctagaatct gctggctact acttgaagat ggtgatcgct cacaccaaat   1440

ccttggaccc ctcccggcct gtgacctttg tgagcaactc taactatgca gcagacaagg   1500

gggctccgta tgtggatgtg atctgtttga acagctacta ctcttggtat cacgactacg   1560

ggcacctgga gttgattcag ctgcagctgg ccacccagtt tgagaactgg tataagaagt   1620

atcagaagcc cattattcag agcgagtatg gagcagaaac gattgcaggg tttcaccagg   1680

atccacctct gatgttcact gaagagtacc agaaaagtct gctagagcag taccatctgg   1740

gtctggatca aaaacgcaga aaatatgtgg ttggagagct catttggaat tttgccgatt   1800

tcatgactga acagtcaccg acgagagtgc tggggaataa aaaggggatc ttcactcggc   1860

agagacaacc aaaaagtgca gcgttccttt tgcgagagag atactggaag attgccaatg   1920

aaaccaggta tccccactca gtagccaagt cacaatgttt ggaaaacagc ccgtttactt   1980

gagcaagact gataccacct gcgtgtccct tcctccccga gtcagggcga cttccacagc   2040

agcagaacaa gtgcctcctg gactgttcac ggcagaccag aacgtttctg gcctgggttt   2100

tgtggtcatc tattctagca gggaacacta aaggtggaaa taaaagattt tctattatgg   2160

aaataaagag ttggcatgaa agtcgctact g                                 2191


<210> SEQ ID NO 8
<211> LENGTH: 1616
<212> TYPE: DNA
<213> ORGANISM: Bacillus sphaericus

<400> SEQUENCE: 8

tttaaaaata ctacttcata gtatagaaat aatagtaacg ccaaaaaatg acggtgtatg     60

tggcgcgatg tggcgttatt gcatgggatt ggaaatttca gtcttaaaaa aaggtgtatg    120

accgccaaaa aacggcgtaa atttatcctt gaatttccat taatggaagt gatagtatgg    180

ttttggaagc ggaataaatc tatttttagt taattatggt actcgtgata agtgaagtaa    240

attctttatt atgaagatac gttagttgat ttaaaaataa ttccgttaca ttttttttaaa    300

atactttttc aagggagtgt tttttatgtt aggttgcagt agcttatcaa ttcgtacaac    360

agatgataaa agtttattcg ctcgcacaat ggattttaca atggaaccag atagtaaagt    420

gattattgtc ccacgtaatt acggcattcg attgttagaa aaagaaaatg tagtcattaa    480

caattcatat gcttttgttg gaatgggaag cactgacatt acatcaccag ttctctatga    540

tggggtaaac gaaaagggat taatgggcgc aatgctttac tatgctacat ttgcgactta    600

tgctgacgaa cctaaaaaag gcacaacagg catcaatccc gtgtatgtaa tttctcaagt    660

tttaggaaat tgtgtaactg tcgatgatgt tattgaaaaa ttaacttctt atacattatt    720

gaatgaggcc aatataatac ttggctttgc acccccactt cactatacat ttacagatgc    780

ttctggtgaa tcgattgtta ttgaaccgga taaaacaggc attaccattc atcgaaaaac    840

gattggcgtc atgacgaata gccctggcta tgaatggcat cagacaaatt taagagctta    900

cattggtgtc acaccaaatc cgccacaaga tataatgatg ggagacttgg atttgacacc    960

gtttgggcaa ggggcagggg gcttaggatt accaggtgat tttacgccgt cagcacgttt   1020

tcttcgggta gcatactgga aaaaatatac tgaaaaagcc aaaaatgaaa cagaaggcgt   1080

aacaaacttg ttccatattc tatcttctgt aaatatccca aaaggtgttg ttttgacaaa   1140
```

-continued

```
tgaggggaaa acggattata ccatctatac ctcagctatg tgtgcacaaa gtaaaaacta   1200
ttactttaaa ctgtatgaca atagtcgaat ttcagccgtt tccttaatgg ctgaaaattt   1260
aaatagtcaa gatttaatta catttgagtg ggatcgtaaa caagatatta agcaattaaa   1320
tcaagtaaat gtaatgagct aaaaattgcc tattatatag tacaaggtat taaaaaatgc   1380
ccccgattgt tagatatatg aacaatcggg ggctcttttt cgatagtaaa atacacaaag   1440
tcattagaat taaaaagatt tgtggaatgt taatatattg ttagaaatta tttcactgta   1500
aagataggaa agtatccgaa aaagctcatt gtggttgtga ggattgccaa cttttcgcta   1560
agcaaattct atatgcaagt ccacaagttt tggatttctt tagcagaggt ctgcag       1616
```

<210> SEQ ID NO 9
<211> LENGTH: 2409
<212> TYPE: DNA
<213> ORGANISM: Bacillus megaterium

<400> SEQUENCE: 9

```
atgaagatga agtggctaat atcagtcata atcctatttg ttttcatttt tcctcaaaat     60
ctagtttttg ctggggagga taagaatgaa ggggtcaaag tagtacgtga taattttgga    120
gtaccccatt tatacgctaa aaataaaaaa gatttatatg aagcgtatgg atatgttatg    180
gcaaaggatc gactatttca gttggagatg ttccgtcgcg gaaatgaggg gaccgtttca    240
gaaatttttg gagaggatta tctttcaaaa gatgagcaat ccagaagaga tggatatagt    300
aataaagaaa ttaaaaaaat gattgacggt ctggatcgtc agccaaaaga attaatagca    360
aaatttgctg aaggtatttc acgttatgta aatgaagctt taaaagatcc agatgataaa    420
ctttcgaagg agtttcatga atatcagttt ttaccgcaaa aatggacttc aacagatgtt    480
gtccgtgttt atatggtatc catgacgtat tttatggata atcaccagga gttaaaaaac    540
gcagagatac ttgcaaagct agaacatgaa tatgggacag aagtttcccg gaaaatgttt    600
gatgatttag tgtggaaaaa tgatcctagc gctcctacaa gcattgtaag cgaggggaaa    660
ccaaaaaggg aatcgtcatc tcaatccctt caaaaactgt cttcagctgt aatcaaagct    720
tctgaaaaag ttggaaagga aagggagaat tttgtccaat cgtctgaaga acttggatta    780
ccgttaaaga taggcagtaa tgccgccata gtcggttccg agaaatccgc aacaggaaat    840
gctttattat tcagtggacc acaagtaggt tttgttgctc ctggattttt gtacgaggta    900
ggtttgcatg cgccaggttt cgatatggaa ggttcaggtt tcataggcta tcctttcatc    960
atgttcggag ccaacaatca ctttgctcta agtgcgacag ctgggtacgg aaatgtaacc   1020
gatatctttg aggaaaaatt gaatacgaaa aactcttccc agtatttata caaagggaag   1080
tggagagaca tggaaaagag gaaggaatct ttcacggtca aaggagacaa tggtgaaaag   1140
aaaacagtag aaaagattta ttatcgaaca gtacatggtc ctgtaattag tagagatgaa   1200
acaaataaag tggcttacag taagtcgtgg tctttccgtg gaactgaggc ccaaagcatg   1260
tcggcttaca tgaaagcgaa ttgggcaaaa aacttaaaag aatttgagaa tgcagctagt   1320
gaatatacga tgtctttgaa ttggtattat gcggataaga aaggtgatat agcgtattat   1380
catgtaggaa gatatccagt tagaaacaac aaaattgatg aaagaatccc tacaccagga   1440
acaggagaat atgagtggaa aggttttatt cctttttaaag agaaccctca tgtaatcaat   1500
ccgaagaatg gctatgtagt taattggaac aataagcctt ctaaagagtg ggtaaatggt   1560
gaatatagtt attattgggg tgaggataat cgagtccaac aatatatcaa tgggatggaa   1620
```

```
gcgagaggga aagttacatt agaagatatt aatgaaatta attatacggc aagctttgca   1680

cagcttcgag caaacctctt taaaccgtta ttaattgatg tgttggacaa gaataaatca   1740

accaacggga actacgccta tttaattgaa aaactggaag aatggaataa tctaaaagaa   1800

gacgaaaata aagatggata ttatgatgca gggattgcgg cattctttga tgaatggtgg   1860

aataatctcc atgataaact ctttatggat gaattgggag acttctatgg aataacgaaa   1920

gaaattaccg atcatcgtta tggggcttca ttagcatata aaatattaag caaggaatct   1980

acaaactata aatgggtgaa cgtagaccag gaaaaaataa taatggaaag cacaaatgaa   2040

gtacttgcta aattgcaatc agaaaaaggg ttaaaagcag aaaaatggcg tatgcctata   2100

aaaacgatga cttttggtga aaaatcattg attggtattc cccacgggta tggctcaatg   2160

actccaatta ttgaaatgaa tcgtggaagt gaaaatcatt atattgaaat gactccgaaa   2220

gggccgagtg gctttaacat cacaccacct ggtcaaattg gatttgtaaa aaaagatgga   2280

acgataagtg accactatga tgaccaacta gttatgttcg ccgaatggaa attcaagcca   2340

tacttattta acaagaaaga tatttataaa tcagctaaaa atgtaagcgc attaaatatg   2400

agtaagtag                                                            2409


<210> SEQ ID NO 10
<211> LENGTH: 876
<212> TYPE: DNA
<213> ORGANISM: Escherichia coli

<400> SEQUENCE: 10

atggtgacaa agagagtgca acggatgatg ttcgcggcgg cggcgtgcat tccgctgctg     60

ctgggcagcg cgccgcttta tgcgcagacg agtgcggtgc agcaaaagct ggcggcgctg    120

gagaaaagca gcggagggcg gctgggcgtc gcgctcatcg ataccgcaga taatacgcag    180

gtgctttatc gcggtgatga acgctttcca atgtgcagta ccagtaaagt tatggcggcc    240

gcggcggtgc ttaagcagag tgaaacgcaa aagcagctgc ttaatcagcc tgtcgagatc    300

aagcctgccg atctggttaa ctacaatccg attgccgaaa aacacgtcaa cggcacaatg    360

acgctggcag agctgagcgc ggccgcgttg cagtacagcg acaataccgc catgaacaaa    420

ttgattgccc agctcggtgg cccgggaggc gtgacggctt ttgcccgcgc gatcggcgat    480

gagacgtttc gtctggatcg cactgaacct acgctgaata ccgccattcc cggcgacccg    540

agagacacca ccacgccgcg ggcgatggca cagacgttgc gtcagcttac gctgggtcat    600

gcgctgggcg aaacccagcg ggcgcagttg gtgacgtggc tcaaaggcaa tacgaccggc    660

gcagccagca ttcgggccgg cttaccgacg tcgtggactg caggtgataa gaccggcagc    720

ggcggctacg gcaccaccaa tgatattgcg gtgatctggc cgcagggtcg tgcgccgctg    780

gttctggtga cctattttac ccagccgcaa cagaacgcag agagccgccg cgatgtgctg    840

gcttcagcgg cgagaatcat cgccgaaggg ctgtaa                              876


<210> SEQ ID NO 11
<211> LENGTH: 1167
<212> TYPE: DNA
<213> ORGANISM: Escherichia coli

<400> SEQUENCE: 11

tcgcgatctg atcaacgatt cgtggaatct ggtggttgat ggtctggcta aacgcgatca     60

aaaaagagtg cgtccaggct aaagcggaaa tctatagcgc atttttctcg cttaccattt    120

ctcgttgaac cttgtaatct gctggcacgc aaaattactt tcacatggag tctttatgga    180
```

-continued

```
tatcatttct gtcgccttaa agcgtcattc cactaaggca tttgatgcca gcaaaaaact    240

taccccggaa caggccgagc agatcaaaac gctactgcaa tacagcccat ccagcaccaa    300

ctcccagccg tggcatttta ttgttgccag cacggaagaa ggtaaagcgc gtgttgccaa    360

atccgctgcc ggtaattacg tgttcaacga gcgtaaaatg cttgatgcct cgcacgtcgt    420

ggtgttctgt gcaaaaaccg cgatggacga tgtctggctg aagctggttg ttgaccagga    480

agatgccgat ggccgctttg ccacgccgga agcgaaagcc gcgaacgata aaggtcgcaa    540

gttcttcgct gatatgcacc gtaaagatct gcatgatgat gcagagtgga tggcaaaaca    600

ggtttatctc aacgtcggta acttcctgct cggcgtggcg gctctgggtc tggacgcggt    660

acccatcgaa ggttttgacg ccgccatcct cgatgcagaa tttggtctga aagagaaagg    720

ctacaccagt ctggtggttg ttccggtagg tcatcacagc gttgaagatt ttaacgctac    780

gctgccgaaa tctcgtctgc cgcaaaacat caccttaacc gaagtgtaat tctctcttgc    840

cgggcatctg cccggctatt tcctctcaga ttctcctgat ttgcataacc ctgtttcagc    900

cgtcatcata ggctgctgtt gtataaagga gacgttatgc aggatttaat atcccaggtt    960

gaagatttag cgggtattga gatcgatcac accacctcga tggtgatgat tttcggtatt   1020

atttttctga ccgccgtcgt ggtgcatatt attttgcatt gggtggtact gcggaccttc   1080

gaaaaacgtg ccatcgccag ttcacggctt tggttgcaaa tcattaccca gaataaactc   1140

ttccaccgtt tagcttttac cctgcag                                        1167
```

<210> SEQ ID NO 12
<211> LENGTH: 1622
<212> TYPE: DNA
<213> ORGANISM: Homo sapiens

<400> SEQUENCE: 12

```
atgaggctca tcctgcctgt gggtttgatt gctaccactc ttgcaattgc tcctgtccgc     60

tttgacaggg agaaggtgtt ccgcgtgaag ccccaggatg aaaaacaagc agacatcata    120

aaggacttgg ccaaaaccaa tgagcttgac ttctggtatc caggtgccac ccaccacgta    180

gctgctaata tgatggtgga tttccgagtt agtgagaagg aatcccaagc catccagtct    240

gccttggatc aaaataaaat gcactatgaa atcttgattc atgatctaca agaagagatt    300

gagaaacagt ttgatgttaa agaagatatc ccaggcaggc acagctacgc aaaatacaat    360

aattgggaaa agattgtggc ttggactgaa aagatgatgg ataagtatcc tgaaatggtc    420

tctcgtatta aaattggatc tactgttgaa gataatccac tatatgttct gaagattggg    480

gaaaagaatg aaagaagaaa ggctattttt atggattgtg gcattcacgc acgagaatgg    540

gtctccccag cattctgcca gtggtttgtc tatcaggcaa ccaaaactta tgggagaaac    600

aaaattatga ccaaactctt ggaccgaatg aatttttaca ttcttcctgt gttcaatgtt    660

gatggatata tttggtcatg gacaaagaac cgcatgtgga gaaaaaatcg ttccaagaac    720

caaaactcca aatgcatcgg cactgacctc aacaggaatt ttaatgcttc atggaactcc    780

attcctaaca ccaatgaccc atgtgcagat aactatcggg gctctgcacc agagtccgag    840

aaagagacga aagctgtcac taatttcatt agaagccacc tgaatgaaat caaggtttac    900

atcaccttcc attcctactc ccagatgcta ttgtttccct atggatatac atcaaaactg    960

ccacctaacc atgaggactt ggccaaagtt gcaaagattg gcactgatgt tctatcaact   1020

cgatatgaaa cccgctacat ctatggccca atagaatcaa caatttaccc gatatcaggt   1080
```

-continued

```
tcttctttag actgggctta tgacctgggc atcaaacaca catttgcctt tgagctccga   1140

gataaaggca aatttggttt tctccttcca gaatcccgga taaagccaac gtgcagagag   1200

accatgctag ctgtcaaatt tattgccaag tatatcctca agcatacttc ctaaagaact   1260

gccctctgtt tggaataagc caattaatcc ttttttgtgc ctttcatcag aaagtcaatc   1320

ttcagttatc cccaaatgca gcttctattt cacctgaatc cttctcttgc tcatttaagt   1380

cccatgttac tgctgtttgc ttttacttac tttcagtagc accataacga agtagcttta   1440

agtgaaacct tttaactacc tttctttgct ccaagtgaag tttggaccca gcagaaagca   1500

ttattttgaa aggtgatata cagtggggca cagaaaacaa atgaaaaccc tcagtttctc   1560

acagattttc accatgtggc ttcatcaatt tatgtgctaa tacaataaaa taaaatgcac   1620

tt                                                                  1622


<210> SEQ ID NO 13
<211> LENGTH: 1705
<212> TYPE: DNA
<213> ORGANISM: Manihot esculenta

<400> SEQUENCE: 13

acaactttct tcagctatca gggatgctcg tcttgttcat aagcttgttg gctctcacta     60

ggccagcaat gggaactgat gatgatgatg ataatattcc tgacgatttt agccgtaaat    120

attttccaga tgacttcatt tttggaacgg ctacttctgc ttatcagatc gaaggtgaag    180

caaccgcaaa gggtagagca cctagtgttt gggacatatt ttccaaggag actccagata    240

gaatattaga tggcagcaat ggagacgttg cagttgattt ctataaccgc tacatacaag    300

atataaaaaa cgtcaaaaag atgggtttta atgcatttag aatgtccatt tcatggtcta    360

gagttatacc atccggaagg agacgtgaag gagtgaacga ggaaggaatt caattctaca    420

atgatgttat caatgaaatt ataagcaatg gactagagcc ttttgttact atttttcatt    480

gggatactcc tcaagcactg caggacaaat atggtggctt cttaagccgt gatattgtgt    540

acgattatct ccaatatgca gatcttctct ttgaaagatt cggtgatcga gtgaaaccgt    600

ggatgacttt taatgaacca tcagcatatg ttggatttgc ccatgatgat ggagtttttg    660

cccctggtcg atgctcatct tgggtgaatc gccaatgcct agctggagac tcagccacag    720

aaccttatat agttgcccat aatttgcttc tttctcatgc tgcagctgtt caccaatata    780

gaaaatatta tcagggaact caaaagggca agattgggat taccctcttt accttctggt    840

atgaacctct ctccgacagt aaagttgatg tgcaagcagc caaaacagcc ttagatttca    900

tgtttggatt gtggatggat cccatgactt atggacgata tccaagaact atggtagatt    960

tagccggaga taaattgatt ggatttacag atgaagaatc tcaattactt aggggatcat   1020

atgattttgt tggattacaa tactacactg catattatgc agaaccaatt cctccagttg   1080

atccaaaatt tcgtagatac aaaactgata gtggtgttaa tgcgactcct tacgatctta   1140

atggtaatct tattggtcca caggcttact cgtcatggtt ttacattttt ccaaaaggta   1200

ttcgacactt tttgaactat accaaagata catataatga tccagtcatt tacgttactg   1260

agaatggggt tgacaactac aataatgaat ctcaaccaat tgaagaggca cttcaagatg   1320

atttcaggat ttcgtactat aaaaagcata tgtggaatgc actaggatct ctcaagaact   1380

acggtgttaa actcaaaggt tattttgcat ggtcatattt agacaacttc gaatggaata   1440

ttggttatac atcaagattt gggttgtact atgtagacta caaaaataac ctaacaaggt   1500

atcccaagaa atcggctcat tggttcacaa aattcctgaa tatatcggtt aatgcaaata   1560
```

-continued

```
atatctatga gcttacatca aaggattcaa ggaaggttgg caaattctat gtgatgtaga   1620

ttatgtctgg atgttttgtg tgtatctcat aattaaataa tatcgttggg caattatgaa   1680

gctccaatga tctagcatat gttgt                                          1705


<210> SEQ ID NO 14
<211> LENGTH: 1057
<212> TYPE: DNA
<213> ORGANISM: Escherichia coli

<400> SEQUENCE: 14

agcttggaca caagacaggc ttgcgagata tgtttgagaa taccacttta tcccgcgtca     60

gggagaggca gtgcgtaaaa agacgcggac tcatgtgaaa tactggtttt tagtgcgcca    120

gatctctata atctcgcgca acctattttc ccctcgaaca ctttttaagc cgtagataaa    180

caggctggga cacttcacat gagcgaaaaa tacatcgtca cctgggacat gttgcagatc    240

catgcacgta aactcgcaag ccgactgatg ccttctgaac aatggaaagg cattattgcc    300

gtaagccgtg gcggtctggt accgggtgcg ttactggcgc gtgaactggg tattcgtcat    360

gtcgataccg tttgtatttc cagctacgat cacgacaacc agcgcgagct taaagtgctg    420

aaacgcgcag aaggcgatgg cgaaggcttc atcgttattg atgacctggt ggataccggt    480

ggtactgcgg ttgcgattcg tgaaatgtat ccaaaagcgc actttgtcac catcttcgca    540

aaaccggctg gtcgtccgct ggttgatgac tatgttgttg atatcccgca agatacctgg    600

attgaacagc cgtgggatat gggcgtcgta ttcgtcccgc caatctccgg tcgctaatct    660

tttcaacgcc tggcactgcc gggcgttgtt ctttttaact tcaggcgggt tacaatagtt    720

tccagtaagt attctggagg ctgcatccat gacacaggca aacctgagcg aaaccctgtt    780

caaaccccgc tttaaacatc ctgaaacctc gacgctagtc cgccgcttta atcacggcgc    840

acaaccgcct gtgcagtcgg cccttgatgg taaaaccatc cctcactggt atcgcatgat    900

taaccgtctg atgtggatct ggcgcggcat tgacccacgc gaaatcctcg acgtccaggc    960

acgtattgtg atgagcgatg ccgaacgtac cgacgatgat ttatacgata cggtgattgg   1020

ctaccgtggc ggcaactgga tttatgagtg ggccccg                            1057


<210> SEQ ID NO 15
<211> LENGTH: 1718
<212> TYPE: DNA
<213> ORGANISM: Escherichia coli

<400> SEQUENCE: 15

gaatcagacg ggccgatatt ggcgtgcata aaggcgtctg gcagggttct gtcgaggtaa     60

cgccagaaac gttttattcg aacatcgatc tcgtcttgtg ttagaattct aacatacggt    120

tgcaacaacg catccagttg ccccaggtag accggcatcg atgtgaccga cggtacgtgg    180

tggtaaagaa tggtcagcag agagagtgcg tcatcaagat ctttcgcgcc ttccagctcc    240

agccattcgg aaccgttcgc cagaaaacgg gcgtaatcgg gtaagacata gcgcggtttg    300

tacggcgcat gaccttcaaa catatcgcag attacacctt catccaagcg cgcggcgggc    360

ttcggcagga agctgtgggt aaggcagatt gttttctgct tccagtgcca gaaaatggcg    420

cttctgctcc gggctaagca ctgggctggt gacaatttgc tggcaacgtt gttgcagtgc    480

attttcatga gaagtgggca tcttcttttc cttttatgcc gaaggtgatg cgccattgta    540

agaagtttcg tgatgttcac tttgatcctg atgcgtttgc caccactgac gcattcattt    600
```

-continued

```
gaaagtgaat tatttgaacc agatcgcatt acagtgatgc aaacttgtaa gtagatttcc    660

ttaattgtga tgtgtatcga agtgtgttgc ggagtagatg ttagaatact aacaaactcg    720

caaggtgaat tttattggcg acaagccagg agaatgaaat gactgatctg aaagcaagca    780

gcctgcgtgc actgaaattg atggacctga acaccctgaa tgacgacgac accgacgaga    840

aagtgatcgc cctgtgtcat caggccaaaa ctccggtcgg caataccgcc gctatctgta    900

tctatcctcg ctttatcccg attgctcgca aaactctgaa agagcagggc accccggaaa    960

tccgtatcgc tacggtaacc aacttcccac acggtaacga cgacatcgac atcgcgctgg   1020

cagaaacccg tgcggcaatc gcctacggtg ctgatgaagt tgacgttgtg ttcccgtacc   1080

gcgcgctgat ggcgggtaac gagcaggttg gttttgacct ggtgaaagcc tgtaaagagg   1140

cttgcgcggc agcgaatgta ctgctgaaag tgatcatcga aaccggcgaa ctgaaagacg   1200

aagcgctgat ccgtaaagcg tctgaaatct ccatcaaagc gggtgcggac ttcatcaaaa   1260

cctctaccgg taaagtggct gtgaacgcga cgccggaaag cgcgcgcatc atgatggaag   1320

tgatccgtga tatgggcgta gaaaaaaccg ttggtttcaa accggcgggc ggcgtgcgta   1380

ctgcggaaga tgcgcagaaa tatctcgcca ttgcagatga actgttcggt gctgactggg   1440

cagatgcgcg tcactaccgc tttggcgctt ccagcctgct ggcaagcctg ctgaaagcgc   1500

tgggtcacgg cgacggtaag agcgccagca gctactaagt aagatgcttt acgcctgatg   1560

cgctgcgctt atcaggccta cgagacgtat ctacccgtag gccggataag gcgtagacgc   1620

atccggcaaa agccgcctca tactcttttc ctcgggaggt taccttgttt ctcgcacaag   1680

aaattattcg taaaaaacgt gatggtcatg cgctgagc                           1718
```

```
<210> SEQ ID NO 16
<211> LENGTH: 2521
<212> TYPE: DNA
<213> ORGANISM: Homo sapiens

<400> SEQUENCE: 16

ggcacgagcc accgtccagg gagcaggtag ctgctgggct ccggggacac tttgcgttcg     60

ggctgggagc gtgctttcca cgacggtgac acgcttccct ggattggcag ccagactgcc    120

ttccgggtca ctgccatgga ggagccgcag tcagatccta gcgtcgagcc ccctctgagt    180

caggaaacat tttcagacct atggaaacta cttcctgaaa acaacgttct gtcccccttg    240

ccgtcccaag caatggatga tttgatgctg tccccggacg atattgaaca atggttcact    300

gaagacccag gtccagatga agctcccaga atgccagagg ctgctccccg cgtggcccct    360

gcaccagcag ctcctacacc ggcggcccct gcaccagccc cctcctggcc cctgtcatct    420

tctgtccctt cccagaaaac ctaccagggc agctacggtt tccgtctggg cttcttgcat    480

tctgggacag ccaagtctgt gacttgcacg tactcccctg ccctcaacaa gatgttttgc    540

caactggcca agacctgccc tgtgcagctg tgggttgatt ccacaccccc gcccggcacc    600

cgcgtccgcg ccatggccat ctacaagcag tcacagcaca tgacggaggt tgtgaggcgc    660

tgcccccacc atgagcgctg ctcagatagc gatggtctgg cccctcctca gcatcttatc    720

cgagtggaag gaaatttgcg tgtggagtat ttggatgaca gaaacacttt tcgacatagt    780

gtggtggtgc cctatgagcc gcctgaggtt ggctctgact gtaccaccat ccactacaac    840

tacatgtgta acagttcctg catgggcggc atgaaccgga ggcccatcct caccatcatc    900

acactggaag actccagtgg taatctactg ggacggaaca gctttgaggt gcgtgtttgt    960

gcctgtcctg ggagagaccg gcgcacagag gaagagaatc tccgcaagaa aggggagcct   1020
```

caccacgagc tgcccccagg gagcactaag cgagcactgc ccaacaacac cagctcctct 1080
ccccagccaa agaagaaacc actggatgga gaatatttca cccttcagat ccgtgggcgt 1140
gagcgcttcg agatgttccg agagctgaat gaggccttgg aactcaagga tgcccaggct 1200
gggaaggagc cagggggag cagggctcac tccagccacc tgaagtccaa aaagggtcag 1260
tctacctccc gccataaaaa actcatgttc aagacagaag ggcctgactc agactgacat 1320
tctccacttc ttgttcccca ctgacagcct cccaccccca tctctccctc ccctgccatt 1380
ttgggttttg ggtctttgaa cccttgcttg caataggtgt gcgtcagaag cacccaggac 1440
ttccatttgc tttgtcccgg ggctccactg aacaagttgg cctgcactgg tgttttgttg 1500
tggggaggag gatggggagt aggacatacc agcttagatt ttaaggtttt tactgtgagg 1560
gatgtttggg agatgtaaga aatgttcttg cagttaaggg ttagtttaca atcagccaca 1620
ttctaggtag ggcccactt caccgtacta accagggaag ctgtccctca ctgttgaatt 1680
ttctctaact tcaaggccca tatctgtgaa atgctggcat ttgcacctac ctcacagagt 1740
gcattgtgag ggttaatgaa ataatgtaca tctggccttg aaaccacctt ttattacatg 1800
gggtctagaa cttgaccccc ttgagggtgc ttgttccctc tccctgttgg tcggtgggtt 1860
ggtagtttct acagttgggc agctggttag gtagagggag ttgtcaagtc tctgctggcc 1920
cagccaaacc ctgtctgacc acctcttggt gaaccttagt acctaaaagg aaatctcacc 1980
ccatcccaca ccctggagga tttcatctct tgtatatgat gatctggatc caccaagact 2040
tgttttatgc tcagggtcaa tttctttttt cttttttttt tttttttct ttttctttga 2100 gactgggtct cgctttgttg cccaggctgg agtggagtgg cgtgatcttg gcttactgca 2160
gcctttgcct ccccggctcg agcagtcctg cctcagcctc cggagtagct gggaccacag 2220
gttcatgcca ccatggccag ccaacttttg catgttttgt agagatgggg tctcacagtg 2280
ttgcccaggc tggtctcaaa ctcctgggct caggcgatcc acctgtctca gcctcccaga 2340
gtgctgggat tacaattgtg agccaccacg tccagctgga agggtcaaca tcttttacat 2400
tctgcaagca catctgcatt ttcaccccac ccttcccctc cttctccctt tttatatccc 2460
atttttatat cgatctctta ttttacaata aaactttgct gccaaaaaaa aaaaaaaaaa 2520
a 2521

<210> SEQ ID NO 17
<211> LENGTH: 4741
<212> TYPE: DNA
<213> ORGANISM: Homo sapiens

<400> SEQUENCE: 17
tccggttttt ctcaggggac gttgaaatta tttttgtaac gggagtcggg agaggacggg 60
gcgtgccccg acgtgcgcgc gcgtcgtcct ccccggcgct cctccacagc tcgctggctc 120
ccgccgcgga aaggcgtcat gccgcccaaa accccccgaa aaacggccgc caccgccgcc 180
gctgccgccg cggaaccccc ggcaccgccg ccgccgcccc ctcctgagga ggacccagag 240
caggacagcg gcccggagga cctgcctctc gtcaggcttg agtttgaaga aacagaagaa 300
cctgatttta ctgcattatg tcagaaatta aagataccag atcatgtcag agagagagct 360
tggttaactt gggagaaagt ttcatctgtg gatggagtat tgggaggtta tattcaaaag 420
aaaaaggaac tgtggggaat ctgtatcttt attgcagcag ttgacctaga tgagatgtcg 480
ttcactttta ctgagctaca gaaaaacata gaaatcagtg tccataaatt ctttaactta 540

-continued

```
ctaaaagaaa ttgataccag taccaaagtt gataatgcta tgtcaagact gttgaagaag    600

tatgatgtat tgtttgcact cttcagcaaa ttggaaagga catgtgaact tatatatttg    660

acacaaccca gcagttcgat atctactgaa ataaattctg cattggtgct aaaagtttct    720

tggatcacat ttttattagc taaaggggaa gtattacaaa tggaagatga tctggtgatt    780

tcatttcagt taatgctatg tgtccttgac tattttatta aactctcacc tcccatgttg    840

ctcaaagaac catataaaac agctgttata cccattaatg gttcacctcg aacacccagg    900

cgaggtcaga acaggagtgc acggatagca aaacaactag aaaatgatac aagaattatt    960

gaagttctct gtaaagaaca tgaatgtaat atagatgagg tgaaaaatgt ttatttcaaa   1020

aattttatac cttttatgaa ttctcttgga cttgtaacat ctaatggact tccagaggtt   1080

gaaaatcttt ctaaacgata cgaagaaatt tatcttaaaa ataaagatct agatgcaaga   1140

ttatttttgg atcatgataa aactcttcag actgattcta tagacagttt tgaaacacag   1200

agaacaccac gaaaaagtaa ccttgatgaa gaggtgaatg taattcctcc acacactcca   1260

gttaggactg ttatgaacac tatccaacaa ttaatgatga ttttaaattc agcaagtgat   1320

caaccttcag aaaatctgat ttcctatttt aacaactgca cagtgaatcc aaaagaaagt   1380

atactgaaaa gagtgaagga tataggatac atctttaaag agaaatttgc taaagctgtg   1440

ggacagggtt gtgtcgaaat tggatcacag cgatacaaac ttggagttcg cttgtattac   1500

cgagtaatgg aatccatgct taaatcagaa gaagaacgat tatccattca aaattttagc   1560

aaacttctga atgacaacat tttcatatg tctttattgg cgtgcgctct tgaggttgta    1620

atggccacat atagcagtaa gtacatctca gaatcttgat tctggaacag atttgtcttt   1680

cccatggatt ctgaatgtgc ttaatttaaa agcctttgat tttacaaag tgatcgaaag    1740

ttttatcaaa gcagaaggca acttgacaag agaaatgata aaacatttag aacgatgtga   1800

acatcgaatc atggaatccc ttgcatggct ctcagattca cctttatttg atcttattaa   1860

acaatcaaag gaccgagaag gaccaactga tcaccttgaa tctgcttgtc ctcttaatct   1920

tcctctccag aataatcaca ctgcagcaga tatgtatctt tctcctgtaa gatctccaaa   1980

gaaaaaaggt tcaactacgc gtgtaaattc tactgcaaat gcagagacac aagcaacctc   2040

agccttccag acccagaagc cattgaaatc tacctctctt tcactgtttt ataaaaaagt   2100

gtatcggcta gcctatctcc ggctaaatac actttgtgaa cgccttctgt ctgagcaccc   2160

agaattagaa catatcatct ggaccctttt ccagcacacc ctgcagaatg agtatgaact   2220

catgagagac aggcatttgg accaaattat gatgtgttcc atgtatggca tatgcaaagt   2280

gaagaatata gaccttaaat tcaaaatcat tgtaacagca tacaaggatc ttcctcatgc   2340

tgttcaggag acattcaaac gtgttttgat caaagaagag gagtatgatt ctattatagt   2400

attctataac tcggtcttca tgcagagact gaaaacaaat attttgcagt atgcttccac   2460

caggcccccct accttgtcac caatacctca cattcctcga agcccttaca agtttcctag  2520

ttcaccctta cggattcctg gagggaacat ctatatttca cccctgaaga gtccatataa   2580

aatttcagaa ggtctgccaa caccaacaaa aatgactcca agatcaagaa tcttagtatc   2640

aattggtgaa tcattcggga cttctgagaa gttccagaaa ataaatcaga tggtatgtaa   2700

cagcgaccgt gtgctcaaaa gaagtgctga aggaagcaac cctcctaaac cactgaaaaa   2760

actacgcttt gatattgaag gatcagatga agcagatgga agtaaacatc tcccaggaga   2820

gtccaaattt cagcagaaac tggcagaaat gacttctact cgaacacgaa tgcaaaagca   2880

gaaaatgaat gatagcatgg atacctcaaa caaggaagag aaatgaggat ctcaggacct   2940
```

-continued

```
tggtggacac tgtgtacacc tctggattca ttgtctctca cagatgtgac tgtataactt   3000

tcccaggttc tgtttatggc cacatttaat atcttcagct ctttttgtgg atataaaatg   3060

tgcagatgca attgtttggg tgattcctaa gccacttgaa atgttagtca ttgttattta   3120

tacaagattg aaaatcttgt gtaaatcctg ccatttaaaa agttgtagca gattgtttcc   3180

tcttccaaag taaaattgct gtgctttatg gatagtaaga atggccctag agtgggagtc   3240

ctgataaccc aggcctgtct gactactttg ccttcttttg tagcatatag gtgatgtttg   3300

ctcttgtttt tattaattta tatgtatatt tttttaattt aacatgaaca cccttagaaa   3360

atgtgtccta tctatcttcc aaatgcaatt tgattgactg cccattcacc aaaattatcc   3420

tgaactcttc tgcaaaaatg gatattatta gaaattagaa aaaaattact aattttacac   3480

attagatttt attttactat tggaatctga tatactgtgt gcttgtttta taaaattttg   3540

cttttaatta aataaaagct ggaagcaaag tataaccata tgatactatc atactactga   3600

aacagatttc atacctcaga atgtaaaaga acttactgat tattttcttc atccaactta   3660

tgtttttaaa tgaggattat tgatagtact cttggttttt ataccattca gatcactgaa   3720

tttataaagt acccatctag tacttgaaaa agtaaagtgt tctgccagat cttaggtata   3780

gaggacccta acacagtata tcccaagtgc actttctaat gtttctgggt cctgaagaat   3840

taagatacaa attaatttta ctccataaac agactgttaa ttataggagc cttaattttt   3900

ttttcataga gatttgtcta attgcatctc aaaattattc tgccctcctt aatttgggaa   3960

ggtttgtgtt ttctctggaa tggtacatgt cttccatgta tcttttgaac tggcaattgt   4020

ctatttatct tttatttttt taagtcagta tggtctaaca ctggcatgtt caaagccaca   4080

ttatttctag tccaaaatta caagtaatca agggtcatta tgggttaggc attaatgttt   4140

ctatctgatt ttgtgcaaaa gcttcaaatt aaaacagctg cattagaaaa agaggcgctt   4200

ctcccctccc ctacacctaa aggtgtattt aaactatctt gtgtgattaa cttatttaga   4260

gatgctgtaa cttaaaatag gggatattta aggtagcttc agctagcttt taggaaaatc   4320

actttgtcta actcagaatt atttttaaaa agaaatctgg tcttgttaga aaacaaaatt   4380

ttattttgtg ctcatttaag tttcaaactt actattttga cagttatttt gataacaatg   4440

acactagaaa acttgactcc atttcatcat tgtttctgca tgaatatcat acaaatcagt   4500

tagtttttag gtcaagggct tactatttct gggtcttttg ctactaagtt cacattagaa   4560

ttagtgccag aattttagga acttcagaga tcgtgtattg agatttctta aataatgctt   4620

cagatattat tgctttattg ctttttttgta ttggttaaaa ctgtacattt aaaattgcta   4680

tgttactatt ttctacaatt aatagtttgt ctattttaaa ataaattagt tgttaagagt   4740

c                                                                   4741
```

```
<210> SEQ ID NO 18
<211> LENGTH: 809
<212> TYPE: DNA
<213> ORGANISM: Homo sapiens

<400> SEQUENCE: 18

agcggcgagg gctggatcct gggccaaata tatgccaaca acgacaagct ctccaagagg     60

ctgaagaaag tgtggaagcc acagctgttt gagcgagagt tctacagtga gatcctggac    120

aagaagttca cagtgactgt gaccatgcgg accctggacc tcatcgatga ggcttacggg    180

ctcgactttt acatcctcaa gaccccgaag gaggacctgt gctccaagtt tgggatggag    240
```

-continued ctgaagcgag ggatgctgct gcggcttgcc cggcaggacc cccagctgca ccccgaggac 300
cccgagcggc gggcagccat ctacgacaag tacaaggaat ttgccatccc agaggaggag 360
gcagagtggg tgggcctcac gctggaggag gccattgaga agcagagact tttggaggag 420
aaggaccctg tacccctgtt caagatctat gtggcggagc tgatccagca gctgcagcag 480
caggcactgt cagagccggc ggtggtgcag aagacagcca gtggccagtg accacacagc 540
tcctccatgc ctgaccaaca ggcccagctt tccctgccag gccctttgca ctgaggacac 600
agatcccggg gagctgtgag ggccaccggt gggcagtggg tggatcctgg tttcgtgtgc 660
tgcccatgca ccttccagcc cggggccagc ttggcaggga tccccaggag gcctgggccg 720
cccagaggct cctctcaggc tgggccccga cgtttgcggc agtgttcctt gtcccgtggg 780
gccgggagcg agtaaagtct gggccaggc 809

<210> SEQ ID NO 19
<211> LENGTH: 340
<212> TYPE: DNA
<213> ORGANISM: Homo sapiens

<400> SEQUENCE: 19
gaagaaagag gaggggctgg ctggtcacca gagggtgggg cggaccgcgt gcgctcggcg 60
gctgcggaga gggggagagc aggcagcggg cggcggggag cagcatggag ccggcggcgg 120
ggagcagcat ggagccttcg gctgactggc tggccacggc cgcggcccgg ggtcgggtag 180
aggaggtgcg ggcgctgctg gaggcggggg cgctgcccaa cgcaccgaat agttacggtc 240
ggaggccgat ccaggtgggt agagggtctg cagcgggagc aggggatggc gggcgactct 300
ggaggacgaa gtttgcaggg gaattggaat caggtagcgc 340

<210> SEQ ID NO 20
<211> LENGTH: 585
<212> TYPE: DNA
<213> ORGANISM: Homo sapiens

<400> SEQUENCE: 20
ggaaattgga aactggaagc aaatgtaggg gtaattagac acctggggct tgtgtggggg 60
tctgcttggc ggtgaggggg ctctacacaa gcttcctttc cgtcatgccg gcccccaccc 120
tggctctgac cattctgttc tctctggcag gtcatgatga tgggcagcgc ccgagtggcg 180
gagctgctgc tgctccacgg cgcggagccc aactgcgccg accccgccac tctcacccga 240
cccgtgcacg acgctgcccg ggagggcttc ctggacacgc tggtggtgct gcaccgggcc 300
ggggcgcggc tggacgtgcg cgatgcctgg ggccgtctgc ccgtggacct ggctgaggag 360
ctgggccatc gcgatgtcgc acggtacctg cgcgcggctg cgggggggcac cagaggcagt 420 aaccatgccc gcatagatgc cgcggaaggt ccctcaggtg aggactgatg atctgagaat 480
ttgtaccctg agagcttcca aagctcagag cattcatttt ccagcacaga aagttcagcc 540
cgggagacca gtctccggtc ttgcctcagc tcacgcgcca atcgg 585

<210> SEQ ID NO 21
<211> LENGTH: 422
<212> TYPE: DNA
<213> ORGANISM: Homo sapiens

<400> SEQUENCE: 21
ccccggtcgc gctttctctg ccctccgccc gggtggacct ggagcgcttg agcggtcggc 60
gcgcctggag cagccaggcg ggcagtggac tagctgctgg accagggagg tgtgggagag 120

-continued

```
cggtggcggc gggtacatgc acgtgaagcc attgcgagaa ctttatccat aagtatttca    180

atgccggtag ggacggcaag agaggagggc gggatgtgcc acacatcttt gacctcaggt    240

ttctaacgcc tgttttcttt ctgccctctg cagacatccc cgattgaaag aaccagagag    300

gctctgagaa acctcgggaa acttagatca tcagtcaccg aaggtcctac agggccacaa    360

ctgcccccgc cacaacccac cccgctttcg tagttttcat ttagaaaata gagcttttaa    420

aa                                                                   422
```

<210> SEQ ID NO 22
<211> LENGTH: 10907
<212> TYPE: DNA
<213> ORGANISM: Homo sapiens

<400> SEQUENCE: 22

```
tgagcagcct gagatgtcag taattgtagc tgctccaagc ctgggttctg tttttttagtg     60

ggatttctgt tcagatgaac aatccatcct ctgcaatttt ttaaaagcaa aactgcaaat    120

gtttcaggca cagaaaggag gcaaaggtga agtccagggg aggtcagggg tgtgaggtag    180

atgggagcgg atagacacat cactcatttc tgtgtctgtc agaagaacca gtagacactt    240

ccagaattgt cctttattta tgtcatctcc ataaaccatc tgcaaatgag ggttatttgg    300

catttttgtc attttggagc cacagaaata aaggatgaca agcagagagc cccgggcagg    360

aggcaaaagt cctgtgttcc aactatagtc atttctttgc tgcatgatct gagttaggtc    420

accagacttc tctgagcccc agtttcccca gcagtgtata cggggctatgt ggggagtatt    480

caggagacag acaactcact cgtcaaatcc tccccttcct ggccaacaaa gctgctgcaa    540

ccacagggat ttcttctgtt caggtgagtg tagggtgtag ggagattggt tcaatgtcca    600

attcttctgt ttccctggag atcaggttgc cctttttttgg tagtctctcc aattccctcc    660

ttcccggaag catgtgacaa tcaacaactt tgtatactta agttcagtgg acctcaattt    720

cctcatctgt gaaataaacg ggactgaaaa atcattctgg cctcaagatg ctttgttggg    780

gtgtctaggt gctccaggtg cttctgggag aggtgaccta gtgagggatc agtgggaata    840

gaggtgatat tgtggggctt ttctggaaat tgcagagagg tgcatcgttt ttataattta    900

tgaattttta tgtattaatg tcatcctcct gatcttttca gctgcattgg gtaaatcctt    960

gcctgccaga gtgggtcagc ggtgagccag aaagggggct cattctaaca gtgctgtgtc   1020

ctcctggaga gtgccaactc attctccaag taaaaaaagc cagatttgtg gctcacttcg   1080

tggggaaatg tgtccagcgc accaacgcag gcgagggact gggggaggag ggaagtgccc   1140

tcctgcagca cgcgaggttc cggaccggc tggcctgctg gaactcggcc aggctcagct   1200

ggctcggcgc tgggcagcca ggagcctggg ccccggggag ggcggtcccg ggcggcgcgg   1260

tgggccgagc gcgggtcccg cctccttgag gcgggcccgg gcggggcggt tgtatatcag   1320

ggccgcgctg agctgcgcca gctgaggtgt gagcagctgc cgaagtcagt tccttgtgga   1380

gccggagctg ggcgcggatt cgccgaggca ccgaggcact cagaggaggt gagagagcgg   1440

cggcagacaa caggggaccc cgggccggcg gcccagagcc gagccaagcg tgcccgcgtg   1500

tgtccctgcg tgtccgcgag gatgcgtgtt cgcgggtgtg tgctgcgttc acaggtgttt   1560

ctgcggcagg tgaatgacgg gcgtgggtcg gtgcgcgctc ggcttgcgca cacggtgtct   1620

ctataagtgc gcgggtgacg agagtcggga tgtgccggag accccggggc ggagagcggg   1680

attacaagta caggaatccc tggtcacgct ccccgcccct ggaaacccag ctggggcgag   1740
```

-continued

```
ggagggcgtg gacgggaccg ttctgggagc tcgcctttgg ctgcggttgg ctccaggccc   1800
caggcgcagt ttgctcgcgg cgtggggatg aagtccgtgt ccctggaggg gcccaggaag   1860
ggcgaggaaa gcggagtgga gtaagttcgt ctaggatcgg tcccgggtgg ctctgggatc   1920
caatctgcgc cgccctggcc caggtcccag gttcaggtcc tttacgccac tgtgtccacc   1980
acctggctga gcgctgaggt cagcgcgggc tgtttcctgg cccttgggaa tgtgccagga   2040
cccgtcccct aaggactagc gaggaggtga ctcactgtga caaggagacc ccagggaacg   2100
gactgtatga ggtcagaacc ccgcccggga tggggtacag cgggactcca gaagccctct   2160
cccctgcccc ttcgcggtct ccgtcctccc atcggcacag tgacctattt ggctggaaca   2220
gtttgttccc aaggaagccg ggcactggag gtccgggaca ccgcgtcggg tccccgctcc   2280
gcggcgcgct gtaggggtcg gggagtcacg gccctgcgct gggcgggctc taaccagcct   2340
gtcagtcggg gaagggcaag ggtctcctct acctctttcc caccgcggcc gggagaatcg   2400
cggcccagcc tgtcctcggg tcggggcgct ggactccggg gcgggagcgg agcccacgcc   2460
tggatgggag gcggggaggg ttcatgtctt tgaggggtgg ggggtctggg gggcacgacg   2520
ctgctcaggg cctctatcag ctgcctcggg ggctcagggc ttcccgacct agcccagatt   2580
ccctctccga aagctacagg gctgagcgga gcagggggc gagtcgcccc ctggggcgcc    2640
gccgcctggc gcggaccaca gcgcgtcctc tccgtcccaa acccctgggg gacacttgcg   2700
ccctcttcgt gaggaaaagc atcttggagc tgggttagga acttggggcg cccaggcagc   2760
ttcccctctc cttgcctccc tccacgtcgc gtttctggga ggacttgcga gcggttttgt   2820
tttcgttgct cccgtctatt tttattttcc agggatctga ctcatcccgt gctttgggcg   2880
tggagataag gtggaggggc cggctcccgg cgcgcgcgcg cgtgcgtgtc tgcgcgggcg   2940
tgtgtgtgtg tgtgtgtgtg tgtgtgtgtg tgtgtgtctg tgtcagagac ggcacaagag   3000
cgcgcggttt cccaacagcg gcgggagttt cggaagcctg gccggctcag cgtgacgtgt   3060
tcgcggcccc ccggtcccct cccattctcc ccctccccac cccagggtga cgcgcagccg   3120
gagtggaagc agagttttgg cgggcgagca gcgccttgca ggaaactgac tcatcactac   3180
tccctccagc ggtccgaggc tctgcccacg cacctcccac tccgcgcgtg atttcctgga   3240
ggccggcgcc ccctcccggc cctggcggga atagcacaca ggctttcccg cggagtgggg   3300
ctggccggcg cgaaccgccg cggctactcc tgggctcatc cgagatcaac ccctatgcca   3360
ttaccacccc ttcaaaggag cactccttag gttcaacagt attcactgag ctcttactgg   3420
aaattaaaat atggctgaag tctaaggcag gaaggccaat aaaggaggct atttttaatt   3480
gtttctaaaa caagggtttg cgtttctgag ttttctttgg gctgaaagtt attatgagca   3540
tgagagcaga ttttgatggg ggaggagagg cctatgagag ccataagaga aggaggggtg   3600
gtagaagagg agagggtgcc tgcctagatc ctagtcctgt cttgaactcc cgagagccag   3660
ggaatatcca gctccttgat gaagccctag gcgggcgcct cctccttgtg cctatgatgt   3720
attgagaccc agaatgtcca tttcaaacat accagtgtgt ctccgcttgg ctggcacccc   3780
aagagtgccc atctgaggaa ttgtgccaaa cacttgcttg aatcttcaat ttggattaag   3840
ttggtctcgg gaggcagggc ctcagcaatc tatattttga aaaaactccc taggtgcttt   3900
tctttctttc tttctttctt tctttctttc tttctttctt tctttctttc tttctttctt   3960
tctttctttt tctttctttc tttcttttttc tttcttttct ttctttcttt ctttctttct  4020
ttctttcttt ctttctttct tcctttctct ttctctcttt ctttctcttt ctctctttct   4080
ttcttttctt tcgacagagt tgcactctgt cacccaggct ggagtgcaat ggcaccatcc   4140
```

```
tggactcaag tagtcctcct gtttcagcct cccaagtaac cgggaccaca ggcgtgatcc   4200
ccccgccccc atgcccagat tttttttttt tttttttttt ttttgagatg cggtctcgct   4260
ctgtcaccca ggctggagtg cagtggcgtg atctcggctc actgcaagct ccgcctcccg   4320
ggttcacgcc attctcctgc ctcagcctcc cgagtagctg ggactacagg tgctgccatc   4380
atgcccggct aatttttttt tgtattttta gtagagacgg ggtttcacc gtgttagcca   4440
ggatggtctc aatctcctga cctcgtgctc cgccctcctc ggcctcccaa agtgctggga   4500
ttacaggtgt gagacactgc acccaaccac ccagctaatt tttatttatt tttattttta   4560
gtagagacag ggtctcagct agttgcccag gctagtcttg gacccttggg ctcaaatgat   4620
tctcccacct ctgcctccca gagtattagg attacaggca taagccactg cccctggcct   4680
ccccaagtga ttgtgatggg cctctctggt taagaaacct caaaattaga gagggagtgg   4740
ggttcaatac tacagcacag gactcagggc aaacaggcct gggttcagat cctggctgtg   4800
ccacttatga actgtgtgat gttaggcaag ttacttaact tatctgagcc ttggttgcct   4860
cttctgtaaa aagggagcta atagatatcc actttttagg aggattgata tttttaaact   4920
gcttagaaca gcccccaaac ataaaaatat ataaataaat cccaactcat gcctagcaga   4980
gggtggatag aggttatttg agggctctgt ccactgtact gggtgacccc tttatggggc   5040
agtggccttt ggcctttttta gctgtatgac tcaggggcaa gtctcatatc tcttccatct   5100
cctgcccttt aaacttggtg tgaagttacc aagagcctcc tctcccaacc agctgggacg   5160
tgaaactgtg ggctccactg atcacaagca gtggggtgag gtggggtgga gcagatgtgg   5220
catgtgtccc gggcttcctg cctcatgagg actcagcaga gctttcaccc ccagaaactg   5280
caagttggga cttgtcccta ggaaaatcca gttgctgcca aggtcgtgca gtcactcagc   5340
cctggagtca agccagagca ggcaggtagg tgccagggct ccctcatggg caaactcact   5400
ctccgttttc cctctcctga agggggagga gaggagccag gtagaccagc cacctttaat   5460
tttctttttg cctgcaaaac ggtttccttg gacacaggca acacgaggca ggggctgcca   5520
ggtgtctaga cttcagatca cctgatgtgc ctggcaggat gtggctcagc ctgggagaaa   5580
tcatcccttg cgctgccccg cccggcccct ccttacccct aggccacccg cctgacgaca   5640
tccttgggaa aggccctcag cctacagcac ctgtcagctg ctgtctgaag gaggtagttg   5700
gcagggggaa gtgatagggg ggaggctcag taaaactgaa ggcagagagg aataatcata   5760
cttctgtttt caatgcactt ctctatacga agtgctgctg gcacgttacc tacattaact   5820
cagttaattc tcatgtctat cctctgagac agtcactatt actatcccca ttttatagat   5880
gaggaaacta gagctcagac aagttaagtt gcttgcccag ggtcacctag taaaacctgg   5940
actccagccc aggtgatctg gctccagagc cctcctgctt aaccaccagg atacagcctt   6000
tcattcagct ctgttctgtc tgccttgctg catggactct gtgatcaatt tcttgagtat   6060
gtgtctgtag ccatgctctt taaacttgta catggcccca tttatggatg aggaaactga   6120
gacctagaga cattaagtgg ctttttaaag cttacgtagt aactggcaga gctaggacca   6180
caacccgggt gctttttgcc ccaaagtccc gggtactttt acttggcaga gcagggttac   6240
cctacttggg gatctgggtc gggggactta ggaggctgga ggaactgtca gactgtttct   6300
tcttttggga attgaccttc tggccagggc tgcgattagg aaactgctgg actctggcaa   6360
ttcacacata tttggggggc attcacaccc atgagggaca cctctggggg gaaaacaaat   6420
tgattttagc tgataatacc tggtggcaaa caggaccctg gtccttgctc ttgcaataga   6480
```

-continued

```
cttgcctttg ttgacattag cttgcccttc agttgcctgc tctcccagtg accttggtgt   6540
gccaggctgg ctgagctctg ctggtggggg tcaggcctcc tgtgggaagg aagcaggaag   6600
accagctgga aggagtgaga gagaccctct ggtaggaaga cgtcacctga ggtgacacag   6660
caaagcccgg ccaggtaaca tagtgtctaa tctccgccgt gaccagggcc ttccttgtat   6720
ctctgctgca ggcgccatgt cagaaccggc tggggatgtc cgtcagaacc catgcggcag   6780
caaggcctgc cgccgcctct tcggcccagt ggacagcgag cagctgagcc gcgactgtga   6840
tgcgctaatg gcgggctgca tccaggaggc ccgtgagcga tggaacttcg actttgtcac   6900
cgagacacca ctggagggtg acttcgcctg ggagcgtgtg cggggccttg gcctgcccaa   6960
gctctacctt cccacggggc cccggcgagg ccgggatgag ttgggaggag gcaggcggcc   7020
tggcacctca cctgctctgc tgcaggggac agcagaggaa gaccatgtgg acctgtcact   7080
gtcttgtacc cttgtgcctc gctcagggga gcaggctgaa gggtccccag gtggacctgg   7140
agactctcag ggtcgaaaac ggcggcagac cagcatgaca ggtgcggaca tgtgcacgga   7200
aggactttgt aagggaccag gattctcaga atccatggtc caagggctga cctgtctggt   7260
cctggtccag catgctccag gtagaaggaa acaggcccag agaggggaag caacctccct   7320
gaggtcacac agcaagtagg cagcaaagac caactagcta acatttattg ggaatgttca   7380
ttatgccagg ccctttgcca agcttctaag gtagatttat ttagtcctta tagcaatgtt   7440
ataacataag acattcttgt caccctgccc gcctttcttt ttgagacagg tgtcttaact   7500
ctgttggcca gactggagtg cagtgatacg atcatggctc actgcagctt caaactcctg   7560
ggctcaagcg atcttcctac ctcagcctcc tgggtagctg ggaagctggg actatagttg   7620
tacaccacta cgcccggtta attttttgag tttttgtaga gacaaggtct caccatgttg   7680
cccgggctgg tcttgaactc ctgagctcaa gcagtcctcc tgcctcagcc tcccaaagtg   7740
ttgtgattac aggcgtgagc caccatgccc agccccttgc catcctttta gggcaaggaa   7800
accaggctca gagaggtaga gtgatttatc taaggtctca aagtgaattt gccgttgggt   7860
caagactaat tataataaca acaactactg acgtttatat gggcccggca ttgtgctgaa   7920
cactttcatg gattttgtaa cagaatccct agatcagcac tgtccagtaa ctctgcaggg   7980
atgggagtgt ccggtacagg ggccacgagc cacatacggc tgttgtgcat ttgacacaca   8040
gctcatgtga ctgaggaact gaattgttca ttttatttga ttgtagtctg tttaaacaag   8100
cacacagagc tagtagtggt tcctctgctg ggcagcttga cttagagcag acccatgggt   8160
gcgggtgcgg tgatggataa aatcacatct gtgaagcatg gtgggacact ccataatacc   8220
cctcaagaga cagagtggac gttccccgag ttcttcctgt tctcagcagt cggccccatt   8280
ggccccaggg aagggtgtcc tggcccccca ctgtcttcct cagttgggca gctccgccgc   8340
gtcctcttct tcttggcctg gctgacttct gctgtctctc ctcagatttc taccactcca   8400
aacgccggct gatcttctcc aagaggaagc cctaatccgc ccacaggaag cctgcagtcc   8460
tggaagcgcg agggcctcaa aggcccgctc tacatcttct gccttagtct cagtttgtgt   8520
gtcttaatta ttatttgtgt tttaatttaa acacctcctc atgtacatac cctggccgcc   8580
ccctgccccc cagcctctgg cattagaatt atttaaacaa aaactaggcg gttgaatgag   8640
aggttcctaa gagtgctggg catttttatt ttatgaaata ctatttaaag cctcctcatc   8700
ccgtgttctc cttttcctct ctcccggagg ttgggtgggc cggcttcatg ccagctactt   8760
cctcctcccc acttgtccgc tgggtggtac cctctggagg ggtgtggctc cttcccatcg   8820
ctgtcacagg cggttatgaa attcaccccc tttcctggac actcagacct gaattctttt   8880
```

```
tcatttgaga agtaaacaga tggcactttg aaggggcctc accgagtggg ggcatcatca   8940
aaaactttgg agtcccctca cctcctctaa ggttgggcag ggtgaccctg aagtgagcac   9000
agcctagggc tgagctgggg acctggtacc ctcctggctc ttgatacccc cctctgtctt   9060
gtgaaggcag ggggaaggtg gggtcctgga gcagaccacc ccgcctgccc tcatggcccc   9120
tctgacctgc actggggagc ccgtctcagt gttgagcctt ttccctcttt ggctcccctg   9180
taccttttga ggagccccag ctacccttct tctccagctg ggctctgcaa ttcccctctg   9240
ctgctgtccc tccccccttgt cctttccctt cagtaccctc tcagctccag gtggctctga   9300
ggtgcctgtc ccaccccccac ccccagctca atggactgga aggggaaggg acacacaaga   9360
agaagggcac cctagttcta cctcaggcag ctcaagcagc gaccgccccc tcctctagct   9420
gtgggggtga gggtcccatg tggtggcaca ggcccccttg agtggggtta tctctgtgtt   9480
aggggtatat gatgggggag tagatctttc taggagggag acactggccc ctcaaatcgt   9540
ccagcgacct tcctcatcca ccccatccct ccccagttca ttgcactttg attagcagcg   9600
gaacaaggag tcagacattt taagatggtg gcagtagagg ctatggacag ggcatgccac   9660
gtgggctcat atggggctgg gagtagttgt ctttcctggc actaacgttg agcccctgga   9720
ggcactgaag tgcttagtgt acttggagta ttggggtctg accccaaaca ccttccagct   9780
cctgtaacat actggcctgg actgttttct ctcggctccc catgtgtcct ggttcccgtt   9840
tctccaccta gactgtaaac ctctcgaggg cagggaccac accctgtact gttctgtgtc   9900
tttcacagct cctcccacaa tgctgaatat acagcaggtg ctcaataaat gattcttagt   9960
gactttactt gtaatattac tattgtggtt attatacctt ataagaacaa ataaatgggc  10020
ttttgggaag gatttcataa ttaaataatt ttaaaaatta agcatttaaa tttagagaat  10080
gcagaaaact tagcaaacag aaagactgct gcaaaaaaca acagcaaaac aaaaactact  10140
gtcacacctc tgcaaagatc accaatgtca atattttggt ttgttgtgta atctttttgt  10200
aaagaatata ttatagctta acatcattat tcatcagata aatgcaaatt aagataccac  10260
aataagatac caccatacac ttaccagaat gattaaaaaa gactgacagt gccaagcatt  10320
ggcaaggtta tggagcaact ggatctctta tttaaaaaaa ctgtttgggc cgggcgcagt  10380
ggctcacacc tagaatccca gtgcttcggg aggctgaggc aggagatcac ttgaggccaa  10440
gggttcaaga ccagcctggc caacatggtg aaatctctac taaaaataca aaaattagct  10500
gggcatggtg gtgcacgctt gtaatcccag ctacttggaa ggctgaggtg ggaggatcac  10560
ttgaacccag gaggcagagg ttgcagtcag ctgagatcat accactgtac tccagcctct  10620
tccagggtga cagtgagatt catctcaaat aaatacataa ataaaaaaact gtttggtaat  10680
atcttctaaa gatgcctacc ttcatggcta cctcatgacc cagtaattct attcctggac  10740
atgttctcga gagaaatgag ttcatatttc cactgaaaaa ggcataagaa tgttctacac  10800
agtggctcac acctataatc ccagcacttt gggaggctaa ggcaggagga cggcttgagc  10860
ccaagagtgt gagaccagtt tgggcaacat agcgagactc ttatctc                10907
```

<210> SEQ ID NO 23
<211> LENGTH: 756
<212> TYPE: DNA
<213> ORGANISM: Homo sapiens

<400> SEQUENCE: 23

```
gctggaggat gtggctgcag agcctgctgc tcttgggcac tgtggcctgc agcatctctg     60
```

-continued

```
cacccgcccg ctcgcccagc cccagcacgc agccctggga gcatgtgaat gccatccagg    120

aggcccggcg tctcctgaac ctgagtagag acactgctgc tgagatgaat gaaacagtag    180

aagtcatctc agaaatgttt gacctccagg agccgacctg cctacagacc cgcctggagc    240

tgtacaagca gggcctgcgg ggcagcctca ccaagctcaa gggccccttg accatgatgg    300

ccagccacta caagcagcac tgccctccaa ccccggaaac ttcctgtgca acccagacta    360

tcacctttga aagtttcaaa gagaacctga aggactttct gcttgtcatc ccctttgact    420

gctgggagcc agtccaggag tgagaccggc cagatgaggc tggccaagcc ggggagctgc    480

tctctcatga aacaagagct agaaactcag gatggtcatc ttggagggac caaggggtgg    540

gccacagcca tggtgggagt ggcctggacc tgccctgggc cacactgacc ctgatacagg    600

catggcagaa gaatgggaat attttatact gacagaaatc agtaatattt atatatttat    660

atttttaaaa tatttattta tttatttatt taagttcata ttccatattt attcaagatg    720

ttttaccgta ataattatta ttaaaaatat gcttct                              756
```

<210> SEQ ID NO 24
<211> LENGTH: 4830
<212> TYPE: DNA
<213> ORGANISM: Homo sapiens

<400> SEQUENCE: 24

```
ccaggcttgt ccctgctacc cccacccagc ctttcctgag gcctcaggcc tgccaccaag     60

cccccagctc cttctccccg cagggaccca aacacaggcc tcaggactca acacagcttt    120

tccctccaac cccgtttttct ctccctcaag gactcagctt tctgaagccc ctcccagttc    180

tagttctatc tttttcctgc atcctgtctg gaagttagaa ggaaacagac cacagacctg    240

gtccccaaaa gaaatggagg caataggttt tgaggggcat ggggacgggg ttcagcctcc    300

agggtcctac acacaaatca gtcagtggcc cagaagaccc ccctcggaat cggagcaggg    360

aggatgggga gtgtgagggg tatccttgat gcttgtgtgt ccccaacttt ccaaatcccc    420

gcccccgcga tggagaagaa accgagacag aaggtgcagg gcccactacc gcttcctcca    480

gatgagctca tgggtttctc caccaaggaa gttttccgct ggttgaatga ttctttcccc    540

gccctcctct cgccccaggg acatataaag gcagttgttg gcacacccag ccagcagacg    600

ctccctcagc aaggacagca gaggaccagc taagagggag agaagcaact acagaccccc    660

cctgaaaaca accctcagac gccacatccc ctgacaagct gccaggcagg ttctcttcct    720

ctcacatact gacccacggc tccaccctct ctcccctgga aaggacacca tgagcactga    780

aagcatgatc cgggacgtgg agctggccga ggaggcgctc cccaagaaga caggggggcc    840

ccagggctcc aggcggtgct tgttcctcag cctcttctcc ttcctgatcg tggcaggcgc    900

caccacgctc ttctgcctgc tgcactttgg agtgatcggc ccccagaggg aagaggtgag    960

tgcctggcca gccttcatcc actctcccac ccaaggggaa atggagacgc aagagaggga   1020

gagagatggg atgggtgaaa gatgtgcgct gatagggagg gatggagaga aaaaaacgtg   1080

gagaaagacg gggatgcaga aagagatgtg gcaagagatg gggaagagag agagagaaag   1140

atggagagac aggatgtctg gcacatggaa ggtgctcact aagtgtgtat ggagtgaatg   1200

aatgaatgaa tgaatgaaca agcagatata taaataagat atggagacag atgtggggtg   1260

tgagaagaga gatgggggaa gaaacaagtg atatgaataa agatggtgag acagaaagag   1320

cgggaaatat gacagctaag gagagagatg gggagataa ggagagaaga agatagggtg    1380

tctggcacac agaagacact cagggaaaga gctgttgaat gcctggaagg tgaatacaca   1440
```

-continued

```
gatgaatgga gagagaaaac cagacacctc agggctaaga gcgcaggcca gacaggcagc   1500
cagctgttcc tcctttaagg gtgactccct cgatgttaac cattctcctt ctccccaaca   1560
gttccccagg gacctctctc taatcagccc tctggcccag gcagtcagta agtgtctcca   1620
aacctctttc ctaattctgg gtttgggttt gggggtaggg ttagtaccgg tatggaagca   1680
gtgggggaaa tttaaagttt tggtcttggg ggaggatgga tggaggtgaa agtagggggg   1740
tattttctag gaagtttaag ggtctcagct tttcttttc tctctcctct tcaggatcat    1800
cttctcgaac cccgagtgac aagcctgtag cccatgttgt aggtaagagc tctgaggatg   1860
tgtcttggaa cttggagggc taggatttgg ggattgaagc ccggctgatg gtaggcagaa   1920
cttggagaca atgtgagaag gactcgctga gctcaaggga agggtggagg aacagcacag   1980
gccttagtgg gatactcaga acgtcatggc caggtgggat gtgggatgac agacagagag   2040
gacaggaacc ggatgtgggg tgggcagagc tcgagggcca ggatgtggag agtgaaccga   2100
catggccaca ctgactctcc tctccctctc tccctccctc cagcaaaccc tcaagctgag   2160
gggcagctcc agtggctgaa ccgccgggcc aatgccctcc tggccaatgg cgtggagctg   2220
agagataacc agctggtggt gccatcagag ggcctgtacc tcatctactc ccaggtcctc   2280
ttcaagggcc aaggctgccc ctccacccat gtgctcctca cccacaccat cagccgcatc   2340
gccgtctcct accagaccaa ggtcaacctc ctctctgcca tcaagagccc ctgccagagg   2400
gagaccccag agggggctga ggccaagccc tggtatgagc ccatctatct gggaggggtc   2460
ttccagctgg agaagggtga ccgactcagc gctgagatca atcggcccga ctatctcgac   2520
tttgccgagt ctgggcaggt ctactttggg atcattgccc tgtgaggagg acgaacatcc   2580
aaccttccca aacgcctccc ctgccccaat ccctttatta cccccctcctt cagacaccct  2640
caacctcttc tggctcaaaa agagaattgg gggcttaggg tcggaaccca agcttagaac   2700
tttaagcaac aagaccacca cttcgaaacc tgggattcag gaatgtgtgg cctgcacagt   2760
gaagtgctgg caaccactaa gaattcaaac tggggcctcc agaactcact ggggcctaca   2820
gctttgatcc ctgacatctg gaatctggag accagggagc ctttggttct ggccagaatg   2880
ctgcaggact tgagaagacc tcacctagaa attgacacaa gtggacctta ggccttcctc   2940
tctccagatg tttccagact tccttgagac acggagccca gccctcccca tggagccagc   3000
tccctctatt tatgtttgca cttgtgatta tttattattt atttattatt tatttattta   3060
cagatgaatg tatttatttg ggagaccggg gtatcctggg ggacccaatg taggagctgc   3120
cttggctcag acatgtttc cgtgaaaacg gagctgaaca ataggctgtt cccatgtagc    3180
cccctggcct ctgtgccttc ttttgattat gtttttaaa atatttatct gattaagttg    3240
tctaaacaat gctgatttgg tgaccaactg tcactcattg ctgagcctct gctccccagg   3300
ggagttgtgt ctgtaatcgc cctactattc agtggcgaga aataaagttt gcttagaaaa   3360
gaaacatggt ctccttcttg gaattaattc tgcatctgcc tcttcttgtg ggtgggaaga   3420
agctccctaa gtcctctctc cacaggcttt aagatccctc ggacccagtc ccatccttag   3480
actcctaggg ccctggagac cctacataaa caaagcccaa cagaatattc cccatccccc   3540
aggaaacaag agcctgaacc taattacctc tccctcaggg catgggaatt tccaactctg   3600
ggaattccaa tccttgctgg gaaaatcctg cagctcaggt gagatttccg gctgttgcag   3660
ctggccagca gtccggagag agctggagag gagccgcatt ctcaggtacc tgaatcacac   3720
agccaaggga cttccagaga ttcgggtgtc taggcttcaa atcaccctgt cctaactctg   3780
```

```
caacctgaac cagccactta acctatctat ccaatgggga taggaatgtc caccacacat   3840

agggcatgtg agagaaggcc tgacctccat cagaggacct cactcagccc ttggcacagt   3900

gggcacttag tgaattctgg cttccttcaa ccagtttcca gctgttctat ccccttccat   3960

tctctcagtg ggtgaaatcg aagagactga ggacaataaa gaacaaggaa ccgaactgcc   4020

ggacgtggtg gcatgcacct gtaatcctac cactttgcaa ggccaaggtg agaggatcgc   4080

ttgaacccag gagttccaga gcaacctggg caacatagtg agatcctgtc tctatttttt   4140

aaaaaagaat gaaacatagg aataagatgt gggtgaagga ctcacatgcc ggcttggtcc   4200

cactggtctt tgtggtgaag gaggggagag gtgagaggtg ggtaatccgg aaagagaaaa   4260

gcaccccctc cctggatgaa ggctcttctg gagagagtca aagacaaata agggtggggc   4320

gcagtggctc atgcctgtta tcccaacact ttgggaggct gaggtgggag gaccacttga   4380

gcccactagt tcaagaccag cctgtgcaac atagcaagac cttgtttcta gaaaaaaaat   4440

taaagattag tcaggtgtag tggtgcatgc ctgtaatcct agctcctcag gaggctgagg   4500

caggaggatc actcaagccc aggagtttga ggttacagta agctatgatc atgccactgt   4560

acccccgtct gggtgacaga acgagaccct gtctcaaaaa aataataatt ccaaaaacaa   4620

atatggagac ggaaattgag ccccccctaga ctgggagccc ccactgagtt cggaaattag   4680

gctttacctc cagccctggg gtgccaggca ggagaaaacc atgtggtagg ctgagggggt   4740

agggtgaccc attggggtga cctagatagg gccttgggtc accctctgcc tcctccagcc   4800

tgtggctgaa agtcagccat gaagtaatgg                                    4830
```

```
<210> SEQ ID NO 25
<211> LENGTH: 737
<212> TYPE: DNA
<213> ORGANISM: Homo sapiens

<400> SEQUENCE: 25

tacccacctc aggtagccta gtgatatttg caaaatccca atggcccggt ccttttcttt     60

actgatggcc gtgctggtac tcagctacaa atccatctgc tctctgggct gtgatctgcc    120

tcagacccac agcctgcgta ataggagggc cttgatactc ctggcacaaa tgggaagaat    180

ctctcctttc tcctgcttga aggacagaca tgaattcaga ttcccggagg aggagtttga    240

tggccaccag ttccagaaga ctcaagccat ctctgtcctc catgagatga tccagcagac    300

cttcaatctc ttcagcacag aggactcatc tgctgcttgg gaacagagcc tcctagaaaa    360

attttccact gaactttacc agcaactgaa tgacctggaa gcatgtgtga tacaggaggt    420

tggggtggaa gagactcccc tgatgaatga ggacttcatc ctggctgtga ggaaatactt    480

ccaaagaatc actctttatc taacagagaa gaaatacagc ccttgtgcct gggaggttgt    540

cagagcagaa atcatgagat ccttctcttt ttcaacaaac ttgaaaaaag gattaaggag    600

gaaggattga aaactggttc atcatggaaa tgattctcat tgactaatgc atcatctcac    660

actttcatga gttcttccat ttcaaagact cacttctata accaccacaa gttgaatcaa    720

aatttccaaa tgttttc                                                   737

<210> SEQ ID NO 26
<211> LENGTH: 5961
<212> TYPE: DNA
<213> ORGANISM: Homo sapiens

<400> SEQUENCE: 26

agcaaatgat caatgtgctt tgtgaatgaa gagtcaacat tttaccaggg cgaagtgggg     60
```

-continued

```
aggtacaaaa aaatttccag tccttgaatg gtgtgaagta aaagtgcctc aaagaatccc    120
accagaatgg cacaggtggg cataatgggt ctgtctcatc gtcaaaggac ccaaggagtc    180
taaaggaaac tctaactaca acacccaaat gccacaaaac cttagttatt aatacaaact    240
atcatccctg cctatctgtc accatctcat cttaaaaaac ttgtgaaaat acgtaatcct    300
caggagactt caattaggta taaataccag cagccagagg aggtgcagca cattgttctg    360
atcatctgaa gatcagctat tagaagagaa agatcagtta agtcctttgg acctgatcag    420
cttgatacaa gaactactga tttcaacttc tttggcttaa ttctctcgga aacgatgaaa    480
tatacaagtt atatcttggc ttttcagctc tgcatcgttt tgggttctct tggctgttac    540
tgccaggacc catatgtaaa agaagcagaa aaccttaaga aatattttgt aagtatgact    600
ttttaatagt acttgtttgt ggttgaaaat gactgaatat cgacttgctg tagcatctct    660
gataggctgt catctcttgt aggcagtcat tttgagattt ggtgttattt tgttaattat    720
tgactagatg agttccttga ctaaataatc tagatattgt tttaaccttc tgctcagttt    780
gtatagagac ttaaaaggga tttatgaatt ttccaaaaga tgggcataat atgggtatga    840
agcataatga tgttaataat tttgtggtgg gaactcattc agttgtgata gtcaaggagt    900
atgcagattg aaaaaaatga ttggttatta gtttttgact tctcagactc taaggtcaag    960
attagcatta aaaaggtaat aggaaatgtt tacaaattaa agtcaaaaag gtccttaaag   1020
ctttggctta aaaaaataac tgataggtga ttttctccaa aaagtgattt caacattctg   1080
cttctctatc tatattactt gtgaagtatt ccggaacttc gttgctcact gggattttgg   1140
aagaattatg attctggcta aggaatgttt aaaaatttta agtgaatttt ttgagtttct   1200
tttaaaattt tattgatggt taatgaaaag tttttacatt ttaaatattt cattatttgt   1260
ttaaaactta gctgttataa ttatagctgt cataataata ttcagacatt cacaattgat   1320
tttattctta caacacaaaa tcaaatctca cacacacaca cacacacaca cactcgcaca   1380
tgtttggaac tatcttttaa agctcgtata ataataccct acaggaaggc acagtagatg   1440
taatagaaac ctgtaccatt ggggggcagt attttatagt ggggtggctt tgctgttttt   1500
tgtttttgta ttttttagcc tagcttgaaa atactttctt tagcttacta tagtttttgg   1560
gacctttgga gtatcagctt tgttgagctc atttgtgaca ttgcaattta atggttatat   1620
tgggaaataa aaaagctaaa agaacataat agtctttgtc tatatctcac ataagccttt   1680
tgggaatact tattgttaga actaagcaga agagttgaaa aggaaatcag tgaatattgt   1740
cacatctgag ttcaatgaaa cttgaaatat atttttaagg caatttatgg gctaattgta   1800
aaccaatttt ttcttttttt tttttagaat gcaggtcatt cagatgtagc ggataatgga   1860
actcttttct taggcatttt gaagaattgg aaagaggtaa gctgaatatt cccatttggc   1920
taattttcct gttgcttgct ttctgatgga taaattcaca tcatcctctg tttgtgctct   1980
ttccttccaa ggagagtgac agaaaaataa tgcagagcca aattgtctcc ttttacttca   2040
aactttttaa aaactttaaa gatgaccaga gcatccaaaa gagtgtggag accatcaagg   2100
aagacatgaa tgtcaagttt ttcaatagca acaaaaagaa acgagatgac ttcgaaaagc   2160
tgactaatta ttcggtgagg ctatttaaat tctttctttg gtttcattgc cgagggtctt   2220
gcaaagcatt tattctccag aaagtagaca ttagctattt aacagttgct aaagctatga   2280
actcaactca tggctgaaac tctaccttac tatttccatt cgtgtttggg tgactttgca   2340
aagccagtaa gagaatcgct gaagtatgta atgtagagaa atgctggcat tgtaactatt   2400
```

-continued

```
gcgtaaagac aggtgagttg acaaattcca gtgaagagga agtaggtgag gaagaagcag   2460
ggagtactga gaagcagttc tctcattgtc ccttgctcat atgatggaaa ttctcttact   2520
ttgaatgaga ggctgtctgt cttaatggaa agagcagtgg gaggagctga gaagatgtgt   2580
gttctcctcc caactcagcc accaaggaac tgtgatgaat cacatggctg gctgggctca   2640
gtttcctcat cttaaaagga aactgttagg ttcactgtat aagtttgatg accttctttg   2700
ctccaaaact ctacaatgca aagaatagaa aatgagaatg agatagaaga aagctacagt   2760
ctttgaatag gtaccaggga caccccactg caagtctcta gccaacctat cagattgtac   2820
tgcccaatta gaagcaagaa tggttgctgt ttgtttgttt ttagggaaaa atagatagaa   2880
tttatacctt atgaaaagat tgttctatca actctctatc aactttcaga atatctcagc   2940
tggagaactc cttagactcc taagtcttac ctcatgaact tgtatcttta agttatggct   3000
tctataaaca gaaagataac gttgaggcat aaagacaaat catgtttttc agaatgtttt   3060
ctagaagaca aaggcctcta gattcctttg ggttgactt tgatataaat gggctcaaat    3120
gagagggacc agggtcttca agctagcatt tgtgttctta ggatatgtgc tcagctttca   3180
ctattgctgg gcctgcctct cactcctctc atgtaagccc ccagaaacag aaaggagaga   3240
catggcaaca ggtctccttt ggttataaac tagacactca gcacttgttt ctaatccagt   3300
ggtgcccctg gcttactgtt cagtcctgga taagtctctt agtttcttgg tgatgatttg   3360
aacattggaa agtaaaatct gtcacttgca aacacacagc ttgtcgaaaa ttttttctac   3420
tctgcaggaa ctgggcctta aaaaaatgaa aaaaaatctg tggtttcttc cttctggaag   3480
ctacaaacct cctgtttctt gatgggcaat cttgagtgag ctctattaat tattattctc   3540
tttggctcag ttgctaagct attttatgca tgttatgccc tttgacaatt agtctttagc   3600
tgtaatcccc cagccatcct cagaaatgtg gtgaggtagc catagtgttc ccaagattag   3660
aaaaatgtaa tggcagagcc aagaggaagg taaatggtcc acatcttatg aagcatcatc   3720
taaatggccc tattggttag agtgaggaga tgcaagtagt tcaatttgct tgcctagaag   3780
gcagggtact ggaaaagttg ttgcaattct taattttaaa ctttatatat cagtaagcca   3840
tatataaata tgattggggg tgtttatttt aaaatctatt atggaaattg agagactgac   3900
ctaatctggg agaaattaaa aattacagtt ttcactcgtt ttggatttgg tgttttctag   3960
ggtacctaac ctagatcagt ggttctcaaa cttaggtgga tgtcagaatc acctggggag   4020
cttagtgaat gcacagggca cagtccttcc acttcatgca cctggatctc tgaggtcttt   4080
gacaggtttc cggattaatc tgctatgcac aacagtgaga atcattgacc tatagttact   4140
catttgatgc atacaggaaa gactgaagta taaagtgata taattggtag attgatgata   4200
gagaggtcat agaaacagtc tcatcctcct ttagatgaga aaatagaagt tcagagaggt   4260
taagtagctg gctcaaggtc agaattattg catgcatgag attcaaaccc accttttat    4320
gctgactcca caaccaggag tcttttcact atataatttc aagaattcta tagaagtaga   4380
tttaaagata tgtgatggac tccaccacat tatagcacaa ctagaaatgt aattgtaatt   4440
tttagcttca actgctgaag aagtaaatat tgtatattaa ggtaatacgg tccattttt    4500
aaaggaatac ttttattttc actgaccatc atgacattag cagaatatcc tgatggctta   4560
tatgcctgaa attaattttg ctcttttctt tcccgatagg taactgactt gaatgtccaa   4620
cgcaaagcaa tacatgaact catccaagtg atggctgaac tgtcgccagc agctaaaaca   4680
gggaagcgaa aaaggagtca gatgctgttt cgaggtcgaa gagcatccca gtaatggttg   4740
tcctgcctgc aatatttgaa ttttaaatct aaatctattt attaatattt aacattattt   4800
```

atatggggaa tatattttta gactcatcaa tcaaataagt atttataata gcaacttttg 4860
tgtaatgaaa atgaatatct attaatatat gtattattta taattcctat atcctgtgac 4920
tgtctcactt aatcctttgt tttctgacta attaggcaag gctatgtgat tacaaggctt 4980
tatctcaggg gccaactagg cagccaacct aagcaagatc ccatgggttg tgtgtttatt 5040
tcacttgatg atacaatgaa cacttataag tgaagtgata ctatccagtt actgccggtt 5100
tgaaaatatg cctgcaatct gagccagtgc tttaatggca tgtcagacag aacttgaatg 5160
tgtcaggtga ccctgatgaa aacatagcat ctcaggagat ttcatgcctg gtgcttccaa 5220
atattgttga caactgtgac tgtacccaaa tggaaagtaa ctcatttgtt aaaattatca 5280
atatctaata tatatgaata aagtgtaagt tcacaactac ttatgctgtg ttggactttt 5340
tctaagtgag acctggagtg aaagaactac ctattaatga attagtaggg aggggagtct 5400
tcttagctgt gaaaatttta gagttgcatt tggttccatt aaatgtggta tttctttcca 5460
ctagcatttt gttggctttc gcttttccag ttagcagctc tttgaattat ctttctaaga 5520
tacagattta attatgtcac tattcaattc agaggttctg ctatggaatg tagtttaaac 5580
tgcttagctt ggcacacaga gatttatttc tagccccttc tccaccttcc tatttcctcc 5640
ttcgtttcag aatcttcctc tccctcatcc aatgctggca aacaccagtg ggggtggagt 5700
agtgggtgta agctctaggg agaaggcttg gattggaatc caagttattc cattacaagt 5760
agtgtgacct ttaatacatt atgtatattg tctaagtttc agctttattg tctgaaaaag 5820
aaaaataatt gtgtgttcct cataatattg tggtacgaat tgattctttc actcaagaaa 5880
tatttactgg agtacctact acatgcctgg tgctgttgta gaccttgaga taccttactc 5940
aagcaaaaca gccaaggatc c 5961

<210> SEQ ID NO 27
<211> LENGTH: 2430
<212> TYPE: DNA
<213> ORGANISM: Homo sapiens

<400> SEQUENCE: 27
catttcattg gcgtttgagt cagcaaagaa gtcaagatgg ccaaagttcc agacatgttt 60
gaagacctga agaactgtta cagtgaaaat gaagaagaca gttcctccat tgatcatctg 120
tctctgaatc agaaatcctt ctatcatgta agctatggcc cactccatga aggctgcatg 180
gatcaatctg tgtctctgag tatctctgaa acctctaaaa catccaagct taccttcaag 240
gagagcatgg tggtagtagc aaccaacggg aaggttctga agaagagacg gttgagttta 300
agccaatcca tcactgatga tgacctggag gccatcgcca atgactcaga ggaagaaatc 360
atcaagccta ggtcagcacc ttttagcttc ctgagcaatg tgaaatacaa ctttatgagg 420
atcatcaaat acgaattcat cctgaatgac gccctcaatc aaagtataat tcgagccaat 480
gatcagtacc tcacggctgc tgcattacat aatctggatg aagcagtgaa atttgacatg 540
ggtgcttata agtcatcaaa ggatgatgct aaaattaccg tgattctaag aatctcaaaa 600
actcaattgt atgtgactgc ccaagatgaa gaccaaccag tgctgctgaa ggagatgcct 660
gagataccca aaaccatcac aggtagtgag accaacctcc tcttcttctg ggaaactcac 720
ggcactaaga actatttcac atcagttgcc catccaaact tgtttattgc cacaaagcaa 780
gactactggg tgtgcttggc agggggccca ccctctatca ctgactttca gatactggaa 840
aaccaggcgt aggtctggag tctcacttgt ctcacttgtg cagtgttgac agttcatatg 900

-continued

```
taccatgtac atgaagaagc taaatccttt actgttagtc atttgctgag catgtactga    960

cccttgtaat tctaaatgaa tgtttacact ctttgtaaga gtggaaccaa cactaacata   1020

taatgttgtt atttaaagaa caccctatat tttgcatagt accaatcatt ttaattatta   1080

ttcttcataa caattttagg aggaccagag ctactgacta tggctaccaa aaagactcta   1140

cccatattac agatgggcaa attaaggcat aagaaaacta agaaatatgc acaatagcag   1200

ttgaaacaag aagccacaga cctaggattt catgatttca tttcaactgt ttgccttcta   1260

cttttaagtt gctgatgaac tcttaatcaa atagcataag tttctgggac ctcagtttta   1320

tcattttcaa aatggaggga ataataccta agccttcctg ccgcaacagt tttttatgct   1380

aatcagggag gtcattttgg taaaatactt cttgaagccg agcctcaaga tgaaggcaaa   1440

gcacgaaatg ttatttttta attattattt atatatgtat ttataaatat atttaagata   1500

attataatat actatattta tgggaacccc ttcatcctct gagtgtgacc aggcatcctc   1560

cacaatagca gacagtgttt tctgggataa gtaagtttga tttcattaat acagggcatt   1620

ttggtccaag ttgtgcttat cccatagcca ggaaactctg cattctagta cttgggagac   1680

ctgtaatcat ataataaatg tacattaatt accttgagcc agtaattggt ccgatctttg   1740

actcttttgc cattaaactt acctgggcat tcttgtttca ttcaattcca cctgcaatca   1800

agtcctacaa gctaaaatta gatgaactca actttgacaa ccatgagacc actgttatca   1860

aagttgagtt catctaattt tagcttgtag agacgggatt tcaccatctt ggccgtgctg   1920

gtctcgaact tctgacctcg tgatccaccc gcctcggcct cccaaagtgc tgggattaca   1980

ggcgtgagcc atcgcgcccg gcctggagtt tctactgtgc accaggcact acctttacat   2040

gtattgtttt atttaatcct cagtcagccg tgtttggtag gtgcagttag tatatttcca   2100

ttttcatctg cgcaaacaga ttcaggaact ttgtaattta cataaggtca cattcatcct   2160

aattcacaaa atcaagattt cacacctatt cctttttctt tccagtgcct gtgctttttc   2220

tctcatacca aggagaagta ataagcctaa cgttttaaac ctcacaaaag tacatacaga   2280

aaagtaaata gcctaatttt gcaactaata caaatggcgc tgtacttctt tggtgatggt   2340

agatttataa tttttgaagt atggtagatt caaatgaacc actgaaaagg catttagttt   2400

cttgtcccaa ataaaaaaaa aaaaaaaaaa                                    2430
```

<210> SEQ ID NO 28
<211> LENGTH: 5561
<212> TYPE: DNA
<213> ORGANISM: Homo sapiens

<400> SEQUENCE: 28

```
cgaattcccc tatcacctaa gtgtgggcta atgtaacaaa gagggatttc acctacatcc     60

attcagtcag tctttggggg tttaaagaaa ttccaaagag tcatcagaag aggaaaaatg    120

aaggtaatgt tttttcagac tggtaaagtc tttgaaaata tgtgtaatat gtaaaacatt    180

ttgacacccc cataatattt ttccagaatt aacagtataa attgcatctc ttgttcaaga    240

gttccctatc actctttaat cactactcac agtaacctca actcctgcca caatgtacag    300

gatgcaactc ctgtcttgca ttgcactaag tcttgcactt gtcacaaaca gtgcacctac    360

ttcaagttct acaaagaaaa cacagctaca actggagcat ttactgctgg atttacagat    420

gattttgaat ggaattaatg taagtatatt tcctttctta ctaaaattat tacatttagt    480

aatctagctg gagatcattt cttaataaca atgcattata ctttcttaga attacaagaa    540

tcccaaactc accaggatgc tcacatttaa gttttacatg cccaagaagg taagtacaat    600
```

-continued

```
attttatgtt caatttctgt tttaataaaa ttcaaagtaa tatgaaaatt tgcacagatg    660
ggactaatag cagctcatct gaggtaaaga gtaactttaa tttgtttttt tgaaaaccca    720
agtttgataa tgaagcctct attaaaacag ttttacctat atttttaata tatatttgtg    780
tgttggtggg ggtgggagaa aacataaaaa taatattctc tcactttatc gataagacaa    840
ttctaaacaa aaatgttcat ttatggtttc atttaaaaat gtaaaactct aaaatatttg    900
attatgtcat tttagtatgt aaaataccaa aatctatttc caaggagccc acttttaaaa    960
atcttttctt gttttaggaa aggtttctaa gtgagaggca gcataacact aatagcacag   1020
agtctggggc cagatatctg aagtgaaatc tcagctctgc catgtcctag ctttcatgat   1080
ctttggcaaa ttacctactc tgtttgtgat tcagtttcat gtctacttaa atgaataact   1140
gtatatactt aatatggctt tgtgagaatt agtaagtaaa tgtaaagcac tcagaaccgt   1200
gtctggcata aggtaaatac catacaagca ttagctatta ttagtagtat taaagataaa   1260
attttcactg agaaatacaa agtaaaattt tggactttat ctttttacca atagaacttg   1320
agatttataa tgctatatga cttattttcc aagattaaaa gcttcattag gttgtttttg   1380
gattcagata gagcataagc ataatcatcc aagctcctag gctacattag gtgtgtaaag   1440
ctacctagta gctgtgccag ttaagagaga atgaacaaaa tctggtgcca gaaagagctt   1500
gtgccagggt gaatccaagc ccagaaaata ataggattta aggggacaca gatgcaatcc   1560
cattgactca aattctatta attcaagaga aatctgcttc taactaccct tctgaaagat   1620
gtaaaggaga cagcttacag atgttactct agtttaatca gagccacata atgcaactcc   1680
agcaacataa agatactaga tgctgttttc tgaagaaaat ttctccacat tgttcatgcc   1740
aaaaacttaa acccgaattt gtagaatttg tagtggtgaa ttgaaagcgc aatagatgga   1800
catatcaggg gattggtatt gtcttgacct acctttccca ctaaagagtg ttagaaagat   1860
gagattatgt gcataattta ggggtggtag aattcatgga aatctaagtt tgaaaccaaa   1920
agtaatgata aactctattc atttgttcat ttaaccctca ttgcacattt acaaaagatt   1980
ttagaaacta ataaaaatat ttgattccaa ggatgctatg ttaatgctat aatgagaaag   2040
aaatgaaatc taattctggc tctacctact tatgtggtca aattctgaga tttagtgtgc   2100
ttatttataa agtggagatg atacttcact gcctacttca aaagatgact gtgagaagta   2160
aatgggccta ttttggagaa aattctttta aattgtaata taccatagaa atatgaaata   2220
ttatatataa tatagaatca agaggcctgt ccaaaagtcc tcccaaagta ttataatctt   2280
ttatttcact gggacaaaca tttttaaaat gcatcttaat gtagtgattg tagaaaagta   2340
aaaatttaag acatatttaa aaatgtgtct tgctcaaggc tatattgaga gccactacta   2400
catgattatt gttacctagt gtaaaatgtt gggattgtga tagatggcat ccaagagttc   2460
cttctctctc aacattctgt gattcttaac tcttagacta tcaaatatta taatcataga   2520
atgtgatttt tatgccttcc acattctaat ctcatctggt tctaatgatt ttctatgcag   2580
attggaaaag taatcagcct acatctgtaa taggcattta gatgcagaaa gtctaacatt   2640
ttgcaaagcc aaattaagct aaaaccagtg agtcaactat cacttaacgc tagtcatagg   2700
tacttgagcc ctagtttttc cagttttata atgtaaactc tactggtcca tctttacagt   2760
gacattgaga acagagagaa tggtaaaaac tacatactgc tactccaaat aaaataaatt   2820
ggaaattaat ttctgattct gacctctatg taaactgagc tgatgataat tattattcta   2880
ggccacagaa ctgaaacatc ttcagtgtct agaagaagaa ctcaaacctc tggaggaagt   2940
```

-continued

```
gctaaattta gctcaaagca aaaactttca cttaagaccc agggacttaa tcagcaatat   3000
caacgtaata gttctggaac taaaggtaag gcattacttt atttgctctc ctggaaataa   3060
aaaaaaaaaa gtagggggaa aagtaccaca ttttaaagtg acataacatt tttggtattt   3120
gtaaagtacc catgcatgta attagcctac attttaagta cactgtgaac atgaatcatt   3180
tctaatgtta aatgattaac tggggagtat aagctactga gtttgcacct accatctact   3240
aatggacaag cctcatccca aactccatca cctttcatat taacacaaaa ctgggagtga   3300
gagagaagtg actgagttga gtttcacaga aacgcaggca agattttatt atatattttt   3360
caagttcctt cacagatcat ttactggaat agccaatact gagttacctg aaaggctttt   3420
caaatggtgt ttccttatca tttgatggaa ggactaccca taagagattt gtcttaaaaa   3480
aaaaaactgg agccattaaa atggccagtg gactaaacaa acaacaatct ttttagaggc   3540
aatcccactt tcagaatctt aagtattttt aaatgcacag gaagcataaa atatgcaagg   3600
gactcaggtg atgtaaaaga gattcacttt tgtcttttta tatcccgtct cctaaggtat   3660
aaaattcatg agttaatagg tatcctaaat aagcagcata agtatagtag taaaagacat   3720
tcctaaaagt aactccagtt gtgtccaaat gaatcactta ttagtggact gtttcagttg   3780
aattaaaaaa atacattgag atcaatgtca tctagacatt gacagattca gttccttatc   3840
tatggcaaga gttttactct aaaataatta acatcagaaa actcattctt aactcttgat   3900
acaaatttaa gacaaaacca tgcaaaaatc tgaaaactgt gtttcaaaag ccaaacactt   3960
tttaaaataa aaaaatccca agatatgaca atatttaaac aattatgctt aagaggatac   4020
agaacactgc aacagttttt taaaagagaa tacttattta aagggaacac tctatctcac   4080
ctgcttttgt tcccagggta ggaatcactt caaatttgaa aagctctctt ttaaatctca   4140
ctatatatca aaatagttgc ctccttagct tatcaactag aggaagcgtt taaatagctc   4200
ctttcagcag agaagcctaa tttctaaaaa gccagtccac agaacaaaat ttctaatgtt   4260
taaagctttt aaaagttggc aaattcacct gcattgatac tatgatgggg tagggatagg   4320
tgtaagtatt tatgaagatg ttcattcaca caaatttacc caaacaggaa gcatgtccta   4380
cctagcttac tctagtgtag ctcgtttcgt ctttggggaa aatataagga gattcactta   4440
agtagaaaaa taggagactc taatcaagat ttagaaaaga agaaagtata atgtgcatat   4500
caattcatac atttaactta cacaaatata ggtgtacatt cagaggaaaa gcgatcaagt   4560
ttatttcaca tccagcattt aatatttgtc tagatctatt tttatttaaa tctttatttg   4620
cacccaattt agggaaaaaa tttttgtgtt cattgactga attaacaaat gaggaaaatc   4680
tcagcttctg tgttactatc atttggtatc ataacaaaat acgcaatttt ggcattcatt   4740
ttgatcattt caagaaaatg tgaataatta atatgtttgg taagcttgaa aataaaggca   4800
acaggcctat aagacttcaa ttgggaataa ctgtatataa ggtaaactac tctgtacttt   4860
aaaaaattaa catttttctt ttatagggat ctgaaacaac attcatgtgt gaatatgctg   4920
atgagacagc aaccattgta gaatttctga acagatggat taccttttgt caaagcatca   4980
tctcaacact gacttgataa ttaagtgctt cccacttaaa acatatcagg ccttctattt   5040
atttaaatat ttaaatttta tatttattgt tgaatgtatg gtttgctacc tattgtaact   5100
attattctta atcttaaaac tataaatatg gatcttttat gattcttttt gtaagcccta   5160
ggggctctaa aatggtttca cttatttatc ccaaaatatt tattattatg ttgaatgtta   5220
aatatagtat ctatgtagat tggttagtaa aactatttaa taaatttgat aaatataaac   5280
aagcctggat atttgttatt ttggaaacag cacagagtaa gcatttaaat atttcttagt   5340
```

```
tacttgtgtg aactgtagga tggttaaaat gcttacaaaa gtcactcttt ctctgaagaa   5400

atatgtagaa cagagatgta gacttctcaa aagcccttgc tttgtccttt caagggctga   5460

tcagaccctt agttctggca tctcttagca gattatattt tccttcttct taaaatgcca   5520

aacacaaaca ctcttgaaac tcttcataga tttggtgtgg c                       5561


<210> SEQ ID NO 29
<211> LENGTH: 674
<212> TYPE: DNA
<213> ORGANISM: Homo sapiens

<400> SEQUENCE: 29

gatccaaaca tgagccgcct gcccgtcctg ctcctgctcc aactcctggt ccgccccgga     60

ctccaagctc ccatgaccca gacaacgtcc ttgaagacaa gctgggttaa ctgctctaac    120

atgatcgatg aaattataac acacttaaag cagccacctt tgcctttgct ggacttcaac    180

aacctcaatg gggaagacca agacattctg atggaaaata accttcgaag gccaaacctg    240

gaggcattca acagggctgt caagagttta cagaacgcat cagcaattga gagcattctt    300

aaaaatctcc tgccatgtct gcccctggcc acggccgcac ccacgcgaca tccaatccat    360

atcaaggacg gtgactggaa tgaattccgg aggaaactga cgttctatct gaaaaccctt    420

gagaatgcgc aggctcaaca gacgactttg agcctcgcga tcttttagtc caacgtccag    480

ctcgttctct gggccttctc accacagcgc ctcgggacat caaaaacagc agaacttctg    540

aaacctctgg gtcatctctc acacattcca ggaccagaag catttcacct tttcctgcgg    600

catcagatga attgttaatt atctaatttc tgaaatgtgc agctcccatt tggccttgtg    660

cggttgtgtt ctca                                                      674


<210> SEQ ID NO 30
<211> LENGTH: 9900
<212> TYPE: DNA
<213> ORGANISM: Homo sapiens

<400> SEQUENCE: 30

gaattcaata aaaaacaagc agggcgcgtg gtggggcact gactaggagg gctgatttgt     60

aagttggtaa gactgtagct ctttttccta attagctgag gatgtgttta ggttccattc    120

aaaaagtggg cattcctggc caggcatggt ggctcacacc tgtaatctca gagctttggg    180

agactgaggt aggaggatca cttgagccca ggaatttgag atgagcctag gcaacatagt    240

gagactctta tctctatcaa aaaataaaaa taaaaatgag ccaggcatgg tgcggtggac    300

cacgcaccta ctgctagggg ggctgaggtg ggaggatcat tgagcctggg aggttgaggc    360

tgcagtgatc cctgatcaaa cattgcattt cagcctgggt gacagagtga gaccctgtct    420

cagaaaaaaa aaaaaaaagt cattcctgaa acctcagaat agacctacct tgccaagggc    480

ttccttatgg gtaaggacct tatggacctg ctgggaccca aactaggcct cacctgatac    540

gacctgtcct tctcaaaaca ctaaacttgg gagaacattg tcccccagtg ctggggtagg    600

agagtctgcc tgttattctg cctctatgca gagaaggagc cccagatcat cttttccatg    660

acaggacagt ttccaagatg ccacctgtac ttggaagaag ccaggttaaa atacttttca    720

agtaaaactt tcttgatatt actctatctt tccccaggag gactgcatta caacaaattc    780

ggacacctgt ggcctctccc ttctatgcaa agcaaaaagc cagcagcagc cccaagctga    840

taagattaat ctaaagagca aattatggtg taatttccta tgctgaaact ttgtagttaa    900
```

-continued

```
tttttaaaa aggtttcatt ttcctattgg tctgatttca caggaacatt ttacctgttt    960
gtgaggcatt ttttctcctg gaagagaggt gctgattggc cccaagtgac tgacaatctg   1020
gtgtaacgaa aatttccaat gtaaactcat tttccctcgg tttcagcaat tttaaatcta   1080
tatatagaga tatctttgtc agcattgcat cgttagcttc tcctgataaa ctaattgcct   1140
cacattgtca ctgcaaatcg acacctatta atgggtctca cctcccaact gcttcccccct  1200
ctgttcttcc tgctagcatg tgccggcaac tttgtccacg gacacaagtg cgatatcacc   1260
ttacaggaga tcatcaaaac tttgaacagc ctcacagagc agaaggtgag tacctatctg   1320
gcaccatctc tccagatgtt ctggtgatgc tctcagtatt tctaggcatg aaaacgttaa   1380
cagctgctag agaagttgga actggtggtt ggtggcagtc cagggcacac agcgaggctt   1440
ctccctgcca ctctttttc tgagggtttg taggaagttt cctcagttgg agggagtgag   1500
agctgctcat caaggacttc tctgtccggt tggaggttaa ctctgtctct tgctctctca   1560
tttctgcctg gaccaagact ctgtgcaccg agttgaccgt aacagacatc tttgctgcct   1620
ccaaggtaag aagccgtccc acggtctgtt ttagcaaatg gggagatcca tccccaaatg   1680
tctgaacaag aaacttgtct aatggaaaac gagcgggccc aaattaactc taaggtgtta   1740
gatgttttca aagaacgaga agtctgatct ttactcttaa gcatgttttg gtctttctgg   1800
tttcacttga tttagaagac atgtaataga aagcttacat gctgtagtcc tgactcagat   1860
cctggtcaaa gaaaagccct cttgggtttt acttagcttt ggcatagtgc ctggaacgta   1920
ggaggcactc aataaatgcc tgttgaatga gagaattttt ctggcccata catttctgaa   1980
aaaccaaata ctctcacaga aacagatatt gagatgacag gttgagggag ctttcatttt   2040
gtctaagaga cttcctatgg caacagaaaa ggtatcgcca gagcccctcc tcttccacag   2100
cctggccacc taacagccct ctggttccgg ggctgccgtc cagagctctc agcttgctct   2160
ggccggccga actcccctcc agctcggtct ggaaccatcc tgctgggcag cgtccagcac   2220
atccctgctt cgggctgcct gggcacctcg cctctctgcc tcctgtgctg cctcaccccc   2280
acccctctat ctgtagtggg agggagatag atttgacagc tgatagtgca ttttctctga   2340
caaacacatg actacagccg tatcaatagt tttgtgcatt tcagttcctg ttttcatgga   2400
aacacacggc tgagaatgaa agccccaaag cctcaatttc acagtggtct cctaactacc   2460
tgctttccat gcaaactagg gagatgatat ggccaggagt gaagccctgt gtgttgggca   2520
gggtcacact ccagcaccca gaccatagaa cagggcccat cctgcttcat gagggaaact   2580
gctcttcggg cctttagctg gactatctca tttcattagt tatcccggga gtccgataca   2640
ggatgagatt ctgaagggca aatacacact tttttttttt ttttgagata gggtcttgtt   2700
ctgtcaccca ggctggagtg cagtggtgcg atttcagctc atagcagcct ccacctccca   2760
ggctcaagct atcttcctac ctcagcctcc caagtagccg ggacgacagg tgtgcaccac   2820
cacgcctggc taatttttgt attttttttgt agagatggag tcttgccatt ttgcccaggc  2880
ttgtctcgaa cttctgggct caagcaatcc gtccacctcg gcctctcaaa gtgctgggat   2940
tagccactgc acctgggcaa cagtttatgt gtgtgtgtgt gtgtgtgtgt atatatgtgt   3000
gtgtgtgtat atatatgtgt gtatgtatat atgtgtatgt atatgtgtgt gtgtgtgtgt   3060
gtgtgtgtgt gtgtataaaa tctccaagtc catccaaccg agatggctcc tactagaagc   3120
caagagtcca ccgggttgag cactgggtct ctggaggcct gtcggactgc tgagaaggct   3180
ctaacaaagc caagggaagg gccacctcac tagaagccag gcctggagga agggtgaggg   3240
ctgagggctg gaggtaagac tgcctgtggt tttagaccca ggctctgcca ctgactagct   3300
```

-continued

```
gtgtggctgg ccttcagaca tcttcacagc tctctgcacc tcagtttcca catgtgaaga   3360
tatgaaagtg attctgaagg tgattgcaag gttgattgga atccagctct tgagttagtg   3420
caaagtgtta ttgtgagatg atataaccac gattaaaagc aagaacaggt gcagagaagc   3480
gatgattcta agaaggaggg gaccgggttg gaaaggatca aaccatccag gatgccgagt   3540
ctggggcaat ccatctgggc tgtttctgga agacccccgg gtgcaggcca ggacactgct   3600
gccctcccgt ccttaactcc cctcttcact cagtcctcac tcacctccct ctcacacaca   3660
caaacatctc ctagaataat ccccactgcc tgccttcact cttacccgtc tcatttgcct   3720
cccctgaact tcatcctcct ggagttcacg atctcactct tcactctttt cttcccctcg   3780
aagattcagc actgcttact tacatgttaa gatatttcag aacagtgaaa tgttgctatt   3840
ttcaaaaacc tacaaaggtg gtatgcagag gaaaaggtac ttctttgtgt tcccaaagaa   3900
aacatctttc caaaatccag cctattgatt ttatttcttc gggggaacaa gaattttagt   3960
atctctaagt tgggtagcat tctactcttg gcagttgctg gaaagaaggc actggtctag   4020
gtcctgggct tcacaggtaa cacctgtcag ggtgtctatg aagtcaaggc tgtctgagga   4080
acagcaaagt gggaagaagc aagctggctg gctgatgaag ggtttcttgg gtggacaagt   4140
agttggagcg atttcctatt taccaaagag agctaaagtt cataattcta cagagagttc   4200
cataatgaac ctcaaatacc tctgtttttt gaaggagttt ctcatataca gcactagctg   4260
actatcctgg gcaggatggg agataatgaa tgcagtgcca atcgggctgg atttatatgg   4320
tcctagtgag gctggtcaag aaccgagtta gaactctcac agagtcactg cccacagaag   4380
aaatctccca agtggctgtt tcctgacatt cccgggaggc aggcctcctt ctgagtcact   4440
ccctaagcag ttctgaactg tgaggtcagc caggctgtcc aagtgcactc cctgagccac   4500
tggcagacac actcagcagc cagagctaga caggcaggtg gtaggagtcc agggccacgg   4560
cagggatgga gtgtcgcccc ctcgctgcga taccagagca agtaaaacgt taaggccttg   4620
cactaaagct gcccttagga tgcattcttt taaagttttt ccatttaatg cagactcttt   4680
tcaattctta ttttatcctt gtttccttta gaaagtcctt tgaaaaatat ctttagaggg   4740
ttttttccta tactatgtgg ccatatacgg gtcaaaatta agtttaattt ccaggctcca   4800
agccagcgtt tcagaaaaat ctcaccaagg tttgtggtaa aagaagcaaa gggctgactt   4860
tttggttttc ttgaatctca ctgttccctc tgcagcagca tgcatgtctg cccacctcca   4920
gacacacagg caccatctgc cgccccccat cagcccgtgt cccttccacc tcgactcgcc   4980
tacaaagccc agagaggtct gtttcttggc ccccagagcc caaagatact gacacactct   5040
tacatttcca actagaatca ggaacgagga gtgactctca gtcagttcat taagtaaatg   5100
tctttctaac cgctctgccc atgggacatc acgccccaca ggggaaaggg gaagcttctg   5160
tagcctggga ttctggtgcc tcagtctggg tctagacttt cctgaaaaaa cgttaaaata   5220
tgaactgcat tcctagaatt tagcctacat aaataagaga tgaacacaaa gatttctata   5280
gtttactcac tgccgcttat ttacagaagc aaaaatctgc cacgataggg gcctgacaaa   5340
tgacagtacc actgtgcaat gcgtttctac gcagctctca atcccatgtt ctctaatacc   5400
accgaaggct taggaaatgc ttatggtata tgtaaagagt aaagaagtta caaacagtat   5460
caacagttga cccctatttt aaaaagtatt tttgaaaagt gtgacgatat ttaccaaaat   5520
attaacgagc aatagttacc tctggctggt gggatgagtg aatgtatttt tgttgaatat   5580
atgttacctt tatagtaaat atatgttatc ttgatcatca gaaaaaaaaa tatgtaagaa   5640
```

-continued

```
cttgaaagct gcttggacag cgctgctgat agaaacccct gagcatcttg tcactgttct   5700
tctgattcag agggtctggg tggggcaggg gtggtctgag attctgtatt tctaagaagc   5760
tcccagtgat gtccatgctg ctgtccatgg accacacttt gagtatcaag ggaccagagc   5820
atgtcggggg agaggctggg gatagctttc tttatctgaa ctggataaag gaactgggct   5880
caagctaaga accctctcca ggttctgcat ctttgttctt cagtgaaaaa tgagaggaca   5940
caccaggcca ggttcagact gagacacaat ccctctcctg ggttcccaat gacttgtctc   6000
ttgtccattc ccttctctaa ggctaagggc cccccaggaa gagccatgtg gccagaccct   6060
cacagttgct ggcattccaa ggagattctc actccgcatc attggtccaa aaggcccctt   6120
acagaagctc tgcccaaggc tcagatcaat ggcacctgct cccagagctc ctctgatctc   6180
ccaggacacc tttccctgat ctgtgcactt atctcttgct gcctggcaaa atgtcttagc   6240
tcctcacttg ggccatgtgc tgctctcctc tcccatgggg agagccacac ggagagtgct   6300
ggccaaagca gcagagttca ggccaaagga tgtgcactca tttattcaac aggcatgcag   6360
gatttccagg gaaagctgga ttttaaaacc tctgggaaca agagcagaac ctgactgaga   6420
gctcatgtgg gcacttttca tagcagaata gctcatgagg tatagagaca cggacgcaga   6480
acgtgggctg tagcgacaga tggtcctgca ttctagtccc cactgtgcct tttcctcatg   6540
ggatgacttt attcaggtac cctttcggca aaatcctcca agagaaagga aactgggagg   6600
ttctggggag aaggctgctg cgtttgcaat tgggagaggt tgttgacaga ggtttatgtc   6660
tgtggcaagc agccttcctt cagtggaata cttgaagaca ggtctgtagt tgagcaaact   6720
cacctccatt tgtcctcctg gaaagaagaa atcaagagga aaaatctctc tcccatcctc   6780
caaatggagc tggcacattg ctatctgtgg catttgtctt tccagaacac aactgagaag   6840
gaaaccttct gcagggctgc gactgtgctc cggcagttct acagccacca tgagaaggac   6900
actcgctgcc tgggtgcgac tgcacagcag ttccacaggc acaagcagct gatccgattc   6960
ctgaaacggc tcgacaggaa cctctggggc ctggcgggct tggtaagctg cactgtattc   7020
ctggcaagcc ggccgcgtgg ctcctggtgg acagcagcct cacttctaaa cactccttag   7080
gagctgcagc acccttggtc aacccattca ttcattcact cattcaataa gtatttgctg   7140
aagttccaca agtgctgggt gtggttctag gtgctgagga cgtgtcacta aagacagcag   7200
gccgagtccc tgttctcatg gaatgttcta atgggagagt tagaaaaaca aacatgtaaa   7260
atgatggcca gcagtgatac gtgctacaaa gaaaaacata gaaataaaga acataagagt   7320
catgggggag gggctgact taggagctgg tgacattatc tgagcagata tttgaattga   7380
gggagcaggc cacatgacta actagggaga ccattccagg gagaaggagg aggtatgcaa   7440
aggccttagg atggaaatga actaacttcc tgtatttaaa gaccagtagg aaggccagtg   7500
tggctggatc agagtgagtg aggggtagtt tccaggacag cagatcacac aaggccttta   7560
gattccacca cgagtatgga gggaacacct gcagagcttt gggcaggaca aagactgtac   7620
aatctgattt acgtgattta aaagggtcag tctggctact gtgtggtaaa taggctgaaa   7680
gggggaaagc atagaagcaa gatggcctgt tgggaggcta ccacagtaaa ccaggctaga   7740
gatgatggtg gcgtggacag aatgaagcaa gatggcctgt tgggaggcta ccacagtaaa   7800
ccaggctaga gatgatggtg gcgtggacag aatgaagcaa gatggcctgt tgggaggcta   7860
ccacagtaaa ccaggctaga gatgatggtg gcgtggacaa atggagcagt tgaggtgaac   7920
agatttggga tatgactaaa aataaaacca gaagatttgc tgacagatcg gttgtagggg   7980
gtaagataca ggggaggaaa agatgacctc tttgttcctg cccaaacccc tctggcgatg   8040
```

```
gtcagtactg tttacagaga gatgaaagac tggcggcaag gcagggctgg aggttcagca   8100

gaagatcaag agttcaattt tgtacatcgt acatgtaagg tggctcttgg atagccaagt   8160

gaaggtgttg agaagatggt tagaaaagtc tggaacttag gggagaggtc agaacttgca   8220

atacaaaaag gagagtcctt agatagatac tgctgaaaat ctgaatgaca gaaagggaga   8280

gatcaaagga ctgagcctga gatcaacaca tggaggtcag gagaggagga tccagccaag   8340

gggcctgagg aggagtgacc agtgaggcag gagaacatgg agagtgggcg gtaccccagg   8400

aagccggtga ggacactcaa ggagggaggg ttgactgtgt caaatgtact gaaaggacag   8460

gtcaggtgag gaccaagaaa ggcccctggg tttggctgat ggaggccatg ggtgaggctg   8520

atgtaaatgg agaggcagga aggaaagccc agctggagtg ggctcaccga ggatagggtg   8580

gcgagaggag acaaagaagg aacagtgagg gcagacaact ctttgaagat gtttagctat   8640

aaggctgcag agaaactgag cccacagctg cagggtggtt atggagtgag ggaagctctt   8700

ttaaggttgg gggtataccc agcatgttaa tgcacctggg ggaatggtcc agtggagcag   8760

gaagaactga agagagcaga aagaggaaga atcattaggg ggcagaagtc cttgtagccc   8820

agagtggatg ttatctaata tcgagtggag gaattaattg gctttagagg agaacaagga   8880

catgtatccc ctctctgggc ctatcacctt gtagacaatg ggataggtca tgggatagga   8940

acttggcaca acacatgttc tctcttttaa ttctctccat tatcttatga agcaggcaag   9000

taggcaaaca attgtcccaa ctttacaaaa gaaactgaag cttttataaa ttaagtagta   9060

catcctaagc aatacaatta ataaatggta gagctgagat tcaaactgaa gcagtggcct   9120

gggggtagca tctggaatcc ttcccacctt tagggctgct gtgctgcggt gctgctgttt   9180

aatggcacag agggccagat gactgaatct ctctcagcag tccaggcagt catgcagaag   9240

gcccagtaga gcaccgggca ggtctgagcc agcatcttca agttccaccc tgtgagcaag   9300

cacttagctg tgacacactt ctcgagagac tggactcccc cccgcgcaac ccacccaaaa   9360

gcagataggt aatggtatac agtaaccatt tctagaagtg taagtagtat gcacccaaaa   9420

taggcaaaac ctgctggcct agtgatagag acaactccca gtcaggctag actggaggcc   9480

ttggttttat aagtgttcag gtgacaagtg ccacagtagg cttgatcaag tagacaggca   9540

ggcaagacaa atgcttacca atgcaagcta atgaaatgtt tcttttgcag aattcctgtc   9600

ctgtgaagga agccaaccag agtacgttgg aaaacttctt ggaaaggcta aagacgatca   9660

tgagagagaa atattcaaag tgttcgagct gaatatttta atttatgagt ttttgatagc   9720

tttatttttt aagtatttat atatttataa ctcatcataa aataaagtat atatagaatc   9780

taacagcaat ggcatttaat gtattggcta tgtttacttg acaaatgaaa ttatggtttg   9840

caacttttag ggaaatcaat ttagtttacc aagagactat aaatgctatg gagccaaaac   9900
```

<210> SEQ ID NO 31
<211> LENGTH: 1102
<212> TYPE: DNA
<213> ORGANISM: Homo sapiens

<400> SEQUENCE: 31

```
cagagaagct ctatctcccc tccaggagcc cagctatgaa ctccttctcc acaagcgcct     60

tcggtccagt tgccttctcc ctggggctgc tcctggtgtt gcctgctgcc ttccctgccc    120

cagtaccccc aggagaagat tccaaagatg tagccgcccc acacagacag ccactcacct    180

cttcagaacg aattgacaaa caaattcggt acatcctcga cggcatctca gccctgagaa    240
```

-continued

```
aggagacatg taacaagagt aacatgtgtg aaagcagcaa agaggcactg gcagaaaaca    300

acctgaacct tccaaagatg gctgaaaaag atggatgctt ccaatctgga ttcaatgagg    360

agacttgcct ggtgaaaatc atcactggtc ttttggagtt tgaggtatac ctagagtacc    420

tccagaacag atttgagagt agtgaggaac aagccagagc tgtgcagatg agtacaaaag    480

tcctgatcca gttcctgcag aaaaaggcaa agaatctaga tgcaataacc acccctgacc    540

caaccacaaa tgccagcctg ctgacgaagc tgcaggcaca gaaccagtgg ctgcaggaca    600

tgacaactca tctcattctg cgcagcttta aggagttcct gcagtccagc ctgagggctc    660

ttcggcaaat gtagcatggg cacctcagat tgttgttgtt aatgggcatt ccttcttctg    720

gtcagaaacc tgtccactgg gcacagaact tatgttgttc tctatggaga actaaaagta    780

tgagcgttag gacactattt taattatttt taatttatta atatttaaat atgtgaagct    840

gagttaattt atgtaagtga tatttatatt ttaagaagta ccacttgaaa cattttatgt    900

attagttttg aaataataat ggaaagtggc tatgcagttt gaatatcctt tgtttcagag    960

ccagatcatt tcttggaaag tgtacgctta cctcaaataa atggctaact tatacatatt   1020

tttaaagaaa tatttatatt gtatttatat aatgtataaa atggttttta taccaataaa   1080

tggcatttta aaaaattcag ca                                            1102
```

<210> SEQ ID NO 32
<211> LENGTH: 1589
<212> TYPE: DNA
<213> ORGANISM: Homo sapiens

<400> SEQUENCE: 32

```
gaattcctct ggtcctcatc caggtgcgcg ggaagcaggt gcccaggaga gaggggataa     60

tgaagattcc atgctgatga tcccaaagat tgaacctgca gaccaagcgc aaagtagaaa    120

ctgaaagtac actgctggcg gatcctacgg aagttatgga aaaggcaaag cgcagagcca    180

cgccgtagtg tgtgccgccc cccttgggat ggatgaaact gcagtcgcgg cgtgggtaag    240

aggaaccagc tgcagagatc accctgccca acacagactc ggcaactccg cggaagacca    300

gggtcctggg agtgactatg ggcggtgaga gcttgctcct gctccagttg cggtcatcat    360

gactacgccc gcctcccgca gaccatgttc catgtttctt ttaggtatat ctttggactt    420

cctcccctga tccttgttct gttgccagta gcatcatctg attgtgatat tgaaggtaaa    480

gatggcaaac aatatgagag tgttctaatg gtcagcatcg atcaattatt ggacagcatg    540

aaagaaattg gtagcaattg cctgaataat gaatttaact tttttaaaag acatatctgt    600

gatgctaata aggaaggtat gtttttattc cgtgctgctc gcaagttgag gcaatttctt    660

aaaatgaata gcactggtga ttttgatctc cacttattaa aagtttcaga aggcacaaca    720

atactgttga actgcactgg ccaggttaaa ggaagaaaac cagctgccct gggtgaagcc    780

caaccaacaa agagtttgga agaaaataaa tctttaaagg aacagaaaaa actgaatgac    840

ttgtgtttcc taaagagact attacaagag ataaaaactt gttggaataa aattttgatg    900

ggcactaaag aacactgaaa aatatggagt ggcaatatag aaacacgaac tttagctgca    960

tcctccaaga atctatctgc ttatgcagtt tttcagagtg gaatgcttcc tagaagttac   1020

tgaatgcacc atggtcaaaa cggattaggg catttgagaa atgcatattg tattactaga   1080

agatgaatac aaacaatgga aactgaatgc tccagtcaac aaactatttc ttatatatgt   1140

gaacatttat caatcagtat aattctgtac tgatttttgt aagacaatcc atgtaaggta   1200

tcagttgcaa taatacttct caaacctgtt taaatatttc aagacattaa atctatgaag   1260
```

-continued

```
tatataatgg tttcaaagat tcaaaattga cattgcttta ctgtcaaaat aattttatgg   1320

ctcactatga atctattata ctgtattaag agtgaaaatt gtcttcttct gtgctggaga   1380

tgttttagag ttaacaatga tatatggata atgccggtga gaataagaga gtcataaacc   1440

ttaagtaagc aacagcataa caaggtccaa gatacctaaa agagatttca agagatttaa   1500

ttaatcatga atgtgtaaca cagtgccttc aataaatggt atagcaaatg ttttgacatg   1560

aaaaaaggac aatttcaaaa aaataaaat                                      1589
```

<210> SEQ ID NO 33
<211> LENGTH: 8868
<212> TYPE: DNA
<213> ORGANISM: Homo sapiens

<400> SEQUENCE: 33

```
ccctccaaaa tctatttgca taagcacaca cacacacaca cacacacaca ccccagcagt     60

tcttgcctgc ccagattcct ctgcagctaa agtgatgaaa cttactgggc ggagcttcct    120

aaaaagatta ttagggtctc ctgggttggt gtgcctttaa acctttggac tttaccacct    180

cctatctctc ctatctcctt gcaacaaagg ttaggagaac aagaatgcac aaaaaacggg    240

tcctggatga catctgagtg cctgctttgg gcttcttgat gagtgagaca gaaaataaaa    300

tacaaccccc tcttttaaaa gccatgctta ctcaggtttt ccttcatttg cagctaaata    360

cagaaatgag agaatatttt ggagcaggga tggaagaaga gaggtattcc ccttcccaca    420

accttctgat ttcccactac atcccccact ggaaaaattc atttaaaatc agtataataa    480

gcatttgatt agatgcctac tatgcatctg ggcttgaggg caaactggac tcagcctttt    540

ggcctcaaga agctcacagt gtgagagtgg catttgtgtc ctcttaaatt cacaggacta    600

aattgtccca ggctacattc tatccatcca taggtgcctg ccttctcact tccctctctt    660

catggctctt gccttgtagg aaaatccaaa cccaaatgtg gtgacatgtg agtgttggca    720

ttcatgtctc agacatgacc tatgggcttg ggacttttcc ccgtgtaccc cacgtgactt    780

ttcacgatga acaggtatct ccaaaaactt cgagaaatag gagtcctgtt tgtgtgttct    840

tgttgctttg tcaatatata gagagcacag ggtcatctta taattctaaa aatgttcatt    900

atctatctct tcgacagaaa tactatgaga catacttgat taggagaagc cgttatctcc    960

atatgctaaa tgaggacttg caccagggaa cttgcccatg gttctctcca accacttaaa   1020

ttctgaaatt ttgaaatgag agtggacagt aatttcaaat caatggggaa agaatcaaat   1080

cttcagcaaa tggcttgaga taattagcta cacatttcag aacaaataaa gaagtcagat   1140

ccgggccggg cacagtggct catgctgtaa tctcagcact ctgggaggcc aaggcgggcg   1200

gatcataagg tcaggagatc gagaccatcc tggttaacac agtgaaaccc cgtctctaat   1260

aaaaatacaa aagaaaataa aaaaacttag ccgggcgtgg tgccagcgcc tgtagtccca   1320

gctactcggg agcgtgaggc aggagaatgg cttgaactcg ggaggcagag cttgcagtga   1380

gctgagatca tgccactgca ctccagcctg ggcaacagag cgagactctg tctcaaaaaa   1440

aaaaaaagct agtcagatcc taacctcaac cctatttaac agattataga tgaagaaggt   1500

acaaatggct tttacatacc tcccttctcc ctgacatttt gtatgtgtgt gtgtgtgtat   1560

ttacacacac atctcatata aggaaattga agggaggctg cctgcatccc tgagtcactc   1620

tccctctcct tctgaatgct tacctgtgcc cagaccacct ccttagcctc gcaccctcca   1680

ggcttacagg gcactcttct atgcccatcc caagtatagc tgatacottc caagggccag   1740
```

-continued

```
acttggtgct aagtaccaag tacgcaaaga ttaataaaac aatgtcctgt ttcagggagc   1800
tcaaagctga ttcggcaggg catggtgtgt acatgaatga taaccacgta gggttgcagg   1860
tttcctagtg aggtaagcac aaggcaagat gggaaacaaa ggaaggaggg gttcacagcc   1920
tcacccagag tccagaaccc ctggcctgcc tggtgcccat gctgagtcca cttctggaac   1980
acccagctca gagagggggt tagacctgca ggctaacaca gacacagccc agaaaaccca   2040
ggagccgagg gggaaggaga aaggtgcaag aaggggaaac ccaggtcctg gtccccttct   2100
ctctgcttcc tggcagcaga actcagacag aacccttaag ccagtctaag tctggcagga   2160
ccagtaagtt ctgagttagc tccatactag tttctagcag gctctttctc acttcctgat   2220
tcttaggttt ctacattgac actccctgaa gagttgggaa gagacaccac agtcccctga   2280
ccctgatcca taggtcacac agcagggaca tccacagggt gacgtgggcc ctctcatccc   2340
tccctcccac tcacttcacg ctggctgggc cccaaggtgt ttgcacccct tgcagtgagt   2400
gaccttctct agtgcagcaa gctcagaacc tgctgccact ggagttgtcc cattgctgat   2460
gcagaaaggt gaagaactag cagaacactg gaaatgccct ccatctgggt ccatggctac   2520
ttaagctcaa tgctccctgg caggcaggag gacaggtgct attgccctgt tgggacagat   2580
gaaaaacaga cacagggagg atgagtgatt tgccctgact atagagtggc agggccaagc   2640
agagcccagg cctcctgcac ctaggtcaat gttcctccca gttacagtct aaactggaat   2700
gcaggcaaag cccctgtgga aggggaaggt gaaggctcaa tcaaaggatc cccagagact   2760
ttccagatat ctgaagaagt cctgatgtca ctgccccggt ccttccccag gtagagcaac   2820
actcctcgct gcaacccaac tggctcccct taccttctac acacacacac acacacacac   2880
acacacacac acacacacac acacaaatcc aagacaacac tactaaggct tctttgggag   2940
ggggaagtag ggataggtaa gaggaaagta agggacctcc tatccagcct ccatggaatc   3000
ctgacttctt ttccttgtta tttcaacttc ttccacccca tcttttaaac tttagactcc   3060
agccacagaa gcttacaact aaaagaaact ctaaggccaa tttaatccaa ggtttcattc   3120
tatgtgctgg agatggtgta cagtagggtg aggaaaccaa attctcagtt agcactggtg   3180
tacccttgta caggtgatgt aacatctctg tgcctcagtt tgctcactat aaaatagaga   3240
cggtaggggt catggtgagc actacctgac tagcatataa gaagctttca gcaagtgcag   3300
actactctta cccacttccc ccaagcacag ttggggtggg ggacagctga agaggtggaa   3360
acatgtgcct gagaatccta atgaaatcgg ggtaaaggag cctggaacac atcctgtgac   3420
cccgcctgtc ctgtaggaag ccagtctctg gaaagtaaaa tggaagggct gcttgggaac   3480
tttgaggata tttagcccac cccctcattt ttacttgggg aaactaaggc ccagagacct   3540
aaggtgactg cctaagttag caaggagaag tcttgggtat tcatcccagg ttggggggac   3600
ccaattattt ctcaatccca ttgtattctg gaatgggcaa tttgtccacg tcactgtgac   3660
ctaggaacac gcgaatgaga acccacagct gagggcctct gcggacagaa cagctgttct   3720
ccccaggaaa tcaacttttt ttaattgaga agctaaaaaa ttattctaag agaggtagcc   3780
catcctaaaa atagctgtaa tgcagaagtt catgttcaac caatcatttt tgcttacgat   3840
gcaaaaattg aaaactaagt ttattagaga ggttagagaa ggaggagctc taagcagaaa   3900
aaatcctgtg ccgggaaacc ttgattgtgg ctttttaatg aatgaagagg cctccctgag   3960
cttacaatat aaaagggggga cagagaggtg aaggtctaca catcaggggg ttgctcttgc   4020
aaaaccaaac cacaagacag acttgcaaaa gaaggcatgc acagctcagc actgctctgt   4080
tgcctggtcc tcctgactgg ggtgagggcc agcccaggcc agggcaccca gtctgagaac   4140
```

-continued

```
agctgcaccc acttcccagg caacctgcct aacatgcttc gagatctccg agatgccttc   4200
agcagagtga agactttctt tgtgagtatg attccttcct gtcctttctc tcttcctggg   4260
actgcctgaa ctagacattc tcctggaact ataagaaccc tcctcctgcg cctccacctc   4320
catccccaac acctattccc ccaaacttaa attcttaaga agaaatccta gatcaagcca   4380
tgggttggtc agttaagcta agccagatag atacagtaaa tgtcaggaca cacctgcctt   4440
ataaagtaaa tgcgttcttt ctcgtgctga gaaacttata acgcactcct gctgcgcgcc   4500
tatatcattt attggctagg agaagtaaag aaaggtctga tgtcgaggtg aagatgctcc   4560
ccagtccttg cagcaaggga aatttaaatt gcctctgctt agagcgtttc cagcctgaaa   4620
gaccagtggt ttagggaagc actctaccat gagggaaacc tgcattagaa ggagcttctt   4680
aaatccctgg gatctttcca agctaaactg agtgtctaca gtggggagaa agaaaagcag   4740
agaacaggac atgaggggct caaggccccg aagggttgac ataggtgtcc cttaaagcct   4800
aatgtacgtc cgcagaaaga agaccaggac tgagtcaagc ttctgctttc ccttgaaaat   4860
caggccagat ttttaaaata acttgactct agaggaggag gactgattta agtgatcgtg   4920
tcccatactg ttgaatcctc tgtttttaaa ctcccctttt gtattatatt tggccagagc   4980
caatttgtat taaaaaaaaa aaaatctcta aatgaaaggg catcaaaaat accgcatttc   5040
agttatttcc ccaaacctaa agttcattct cctttttctt cctgcagcaa atgaaggatc   5100
agctggacaa cttgttgtta aaggagtcct tgctggagga ctttaaggtg agagcagggg   5160
cgggggtgct gggggagtgt gcagcatgat taagggaagg gaggctctgc ttcctgattg   5220
tgcagggaat tgggtttgtt tccttggctt gaaaggagaa gtgggaagat gttaactcag   5280
cacatcagca gcagagggtt tacaaagggc tcagtcttcg gggggaggctt ctggtaagga   5340
ggatcgcatg aacaagctgt cctcttaagc tagttgcagc agccctcctc ccagccacct   5400
ccgccaatct ctcactcacc ttcggctcct gccccagggt tacctgggtt gccaagcctt   5460
gtctgagatg atccagtttt acctggagga ggtgatgccc caagctgaga accaagaccc   5520
agacatcaag gcgcatgtga actccctggg ggagaacctg aagaccctca ggctgaggct   5580
acggcgctgt gtaagtagca gatcagttct ttcccttgca gctgccccca aaataccatc   5640
tcctacagac cagcagggac actcacatcc acagacacag caaagagaca cagctgcaag   5700
cgatcgtgta aatgaggaaa gactcctgag tcatagtctc ttctcatttc tctttgagca   5760
ggcgttgggg gtggctgcta ggcatttaca tgtgaaattt gcaaacagct tcctgttatt   5820
tgtgagtcat ttgtgggtta ttaactactc ccctctctct tcataaaagg agcccagagc   5880
ttcagtcagg cctccactgc ctcttttgtac tagacctggg cggggagcta aggttcccaa   5940
agcagaggga aacatcattc acctctttta atctcaatgt ttgaaagcaa agctctaaga   6000
agggcccaat tgactgacag gatttcccct ggcattttag aagggacaag ggggctattc   6060
atccccaggc tagtgtctat gagtaattcc tccaggaatt tatttctcca actgaaatga   6120
tgccgtcact actaatggtt tcccctgttc tgtcaccaat attggaaaat cagttggtgt   6180
ctatttgtag gacaaggcta tgtgaagggt ttggtcccag tagcttccct cctcagatgc   6240
ttagttagtg ttcctccggt ggctgtgact gacggggggg agaacaggag agagaggcag   6300
aaaaggacag gctgaagaat gcctcgctca gcactgcagg agatactgta gagttctggg   6360
ggaggaagga atcccaagac cctgggttgt catccaagcc ttgcaaacat cttggagtga   6420
gtcctggaga aatacattta actcccaggg ccatggaagc agggctcagt tctctctccc   6480
```

-continued

```
agctgtgagg cgaggatttg gataaatctg gcctcctcat gatgcaccag cttgtcccta   6540
agcgtgatgg acatggagct ggaagccagg atcaccaaca ctttctcttt tcttccacag   6600
catcgatttc ttccctgtga aaacaagagc aaggccgtgg agcaggtgaa gaatgccttt   6660
aataaggtag agagggtctc agagcacaac ccatgcccac tccccaaccc caaagcatgg   6720
aaggtggtgg gactcaatag gccccattct tcattgagag agtgtgggaa cctacaatgg   6780
tatgacctct cagccattag gagctgctgc cttgattgta tttgttttct gttaagttgt   6840
ctttgggggt tctaaatgac tgctcgcttg cctttgcagg cttgcgggtc agggctggcc   6900
gcccaggtga acacagatga gctgcatgct ggggagagtg acaaaggaaa cagaaagtac   6960
agaaagtagc ttgttgggaa tctagtctga acccacacgt gcaggaagct ggcacattaa   7020
atgtgcacat tacaaataca cctgggggtg cagcccagat ctcccctagg acctcagaat   7080
gagcaggaag ctggattgct cacttaacct ggagttggtt caagcccgct ttccatctgc   7140
ccttcgcacc tgcggaggtg cctgagaatg tcagtttccc aaacgaaatg ggtttcaca   7200
cttccaactg tgcgtgaact ttttcagtct gatttcccag aaaccgtgcg gcctatgtcc   7260
tcctcgtggg ctggggacag acactgcaca gagtgccaac atcagggggt gtgaatttct   7320
catagtaggt cagggcggca gggagggcct gctcagtgtg ttggtgggag aacacagaca   7380
tttaaaaggc tccctcctct cctctcaccg tcttgctttc gaagcgcttc ctctaatgtc   7440
ttttcatcaa actctgcata atcatcatgt gaatacgtga cctttaaaat tgttgaaaag   7500
gcatcatttt gaagacagtg ctttgcaaaa tgaatgctac cccaattgct agggggaggc   7560
ctggaggaga tgaaaggtca atgcacagcc tttcccaagg cagctaggcc tatcctctgg   7620
tttacttccc agcgtgaggg agaacaagca acctctgcac tcaaggtcat gcccatccat   7680
gagcatgagg gaggggagcc tatttagtcc ccagaaagga ttttaactgt atgtttctta   7740
gctccaagag aaaggcatct acaaagccat gagtgagttt gacatcttca tcaactacat   7800
agaagcctac atgacaatga agatacgaaa ctgagacatc agggtggcga ctctatagac   7860
tctaggacat aaattagagg tctccaaaat cggatctggg gctctgggat agctgaccca   7920
gccccttgag aaaccttatt gtacctctct tatagaatat ttattacctc tgatacctca   7980
acccccattt ctatttattt actgagcttc tctgtgaacg atttagaaag aagcccaata   8040
ttataatttt tttcaatatt tattattttc acctgttttt aagctgtttc catagggtga   8100
cacactatgg tatttgagtg ttttaagata aattataagt tacataaggg aggaaaaaaa   8160
atgttctttg gggagccaac agaagcttcc attccaagcc tgaccacgct ttctagctgt   8220
tgagctgttt tccctgacct ccctctaatt tatcttgtct ctgggcttgg ggcttcctaa   8280
ctgctacaaa tactcttagg aagagaaacc agggagcccc tttgatgatt aattcacctt   8340
ccagtgtctc ggagggattc ccctaacctc attccccaac cacttcattc ttgaaagctg   8400
tggccagctt gttatttata acaacctaaa tttggttcta ggccgggcgc ggtggctcac   8460
gcctgtaatc ccagcacttt gggaggctga ggcgggtgga tcacttgagg tcaggagttc   8520
ctaaccagcc tggtcaacat ggtgaaaccc cgtctctact aaaaatacaa aaattagccg   8580
ggcatggtgg cgcgcacctg taatcccagc tacttgggag gctgaggcaa gagaattgct   8640
tgaacccagg agatggaagt tgcagtgagc tgatatcatg cccctgtact ccagcctggg   8700
tgacagagca agactctgtc tcaaaaaaat aaaaataaaa ataaatttgg ttctaataga   8760
actcagtttt aactagaatt tattcaattc ctctgggaat gttacattgt ttgtctgtct   8820
tcatagcaga ttttaatttt gaataaataa atgtatctta ttcacatc              8868
```

<210> SEQ ID NO 34
<211> LENGTH: 1444
<212> TYPE: DNA
<213> ORGANISM: Homo sapiens

<400> SEQUENCE: 34

```
tttcattttg ggccgagctg gaggcggcgg ggccgtcccg gaacggctgc ggccgggcac     60
cccgggagtt aatccgaaag cgccgcaagc cccgcgggcc ggccgcaccg cacgtgtcac    120
cgagaagctg atgtagagag agacacagaa ggagacagaa agcaagagac cagagtcccg    180
ggaaagtcct gccgcgcctc gggacaatta taaaaatgtg gccccctggg tcagcctccc    240
agccaccgcc ctcacctgcc gcggccacag gtctgcatcc agcggctcgc cctgtgtccc    300
tgcagtgccg gctcagcatg tgtccagcgc gcagcctcct ccttgtggct accctggtcc    360
tcctggacca cctcagtttg gccagaaacc tccccgtggc cactccagac ccaggaatgt    420
tcccatgcct tcaccactcc caaaacctgc tgagggccgt cagcaacatg ctccagaagg    480
ccagacaaac tctagaattt tacccttgca cttctgaaga gattgatcat gaagatatca    540
caaaagataa aaccagcaca gtggaggcct gtttaccatt ggaattaacc aagaatgaga    600
gttgcctaaa ttccagagag acctctttca taactaatgg gagttgcctg gcctccagaa    660
agacctcttt tatgatggcc ctgtgcctta gtagtattta tgaagacttg aagatgtacc    720
aggtggagtt caagaccatg aatgcaaagc ttctgatgga tcctaagagg cagatctttc    780
tagatcaaaa catgctggca gttattgatg agctgatgca ggccctgaat ttcaacagtg    840
agactgtgcc acaaaaatcc tcccttgaag aaccggattt ttataaaact aaaatcaagc    900
tctgcatact tcttcatgct ttcagaattc gggcagtgac tattgataga gtgatgagct    960
atctgaatgc ttcctaaaaa gcgaggtccc tccaaaccgt tgtcattttt ataaaacttt   1020
gaaatgagga aactttgata ggatgtggat taagaactag ggagggggaa agaaggatgg   1080
gactattaca tccacatgat acctctgatc aagtattttt gacatttact gtggataaat   1140
tgtttttaag ttttcatgaa tgaattgcta agaagggaaa atatccatcc tgaaggtgtt   1200
tttcattcac tttaatagaa gggcaaatat ttataagcta tttctgtacc aaagtgtttg   1260
tggaaacaaa catgtaagca taacttattt taaaatattt atttatataa cttggtaatc   1320
atgaaagcat ctgagctaac ttatatttat ttatgttata tttattaaat tatttatcaa   1380
gtgtatttga aaaatatttt taagtgttct aaaaataaaa gtattgaatt aaagtgaaaa   1440
aaaa                                                                1444
```

<210> SEQ ID NO 35
<211> LENGTH: 2347
<212> TYPE: DNA
<213> ORGANISM: Homo sapiens

<400> SEQUENCE: 35

```
ctgtttcagg gccattggac tctccgtcct gcccagagca agatgtgtca ccagcagttg     60
gtcatctctt ggttttccct ggtttttctg gcatctcccc tcgtggccat atgggaactg    120
aagaaagatg tttatgtcgt agaattggat tggtatccgg atgcccctgg agaaatggtg    180
gtcctcacct gtgacacccc tgaagaagat ggtatcacct ggaccttgga ccagagcagt    240
gaggtcttag gctctggcaa aaccctgacc atccaagtca aagagtttgg agatgctggc    300
cagtacacct gtcacaaagg aggcgaggtt ctaagccatt cgctcctgct gcttcacaaa    360
```

-continued

```
aaggaagatg gaatttggtc cactgatatt ttaaaggacc agaaagaacc caaaaataag    420

acctttctaa gatgcgaggc caagaattat tctggacgtt tcacctgctg gtggctgacg    480

acaatcagta ctgatttgac attcagtgtc aaaagcagca gaggctcttc tgaccccaa     540

ggggtgacgt gcggagctgc tacactctct gcagagagag tcagagggga caacaaggag    600

tatgagtact cagtggagtg ccaggaggac agtgcctgcc cagctgctga ggagagtctg    660

cccattgagg tcatggtgga tgccgttcac aagctcaagt atgaaaacta caccagcagc    720

ttcttcatca gggacatcat caaacctgac ccacccaaga acttgcagct gaagccatta    780

aagaattctc ggcaggtgga ggtcagctgg gagtaccctg acacctggag tactccacat    840

tcctacttct ccctgacatt ctgcgttcag gtccagggca agagcaagag agaaaagaaa    900

gatagagtct tcacggacaa gacctcagcc acggtcatct gccgcaaaaa tgccagcatt    960

agcgtgcggg cccaggaccg ctactatagc tcatcttgga gcgaatgggc atctgtgccc   1020

tgcagttagg ttctgatcca ggatgaaaat ttggaggaaa agtggaagat attaagcaaa   1080

atgtttaaag acacaacgga atagacccaa aaagataatt tctatctgat ttgctttaaa   1140

acgttttttt aggatcacaa tgatatcttt gctgtatttg tatagttaga tgctaaatgc   1200

tcattgaaac aatcagctaa tttatgtata gattttccag ctctcaagtt gccatgggcc   1260

ttcatgctat ttaaatattt aagtaattta tgtatttatt agtatattac tgttatttaa   1320

cgtttgtctg ccaggatgta tggaatgttt catactctta tgacctgatc catcaggatc   1380

agtccctatt atgcaaaatg tgaatttaat tttatttgta ctgacaactt ttcaagcaag   1440

gctgcaagta catcagtttt atgacaatca ggaagaatgc agtgttctga taccagtgcc   1500

atcatacact tgtgatggat gggaacgcaa gagatactta catggaaacc tgacaatgca   1560

aacctgttga gaagatccag gagaacaaga tgctagttcc catgtctgtg aagacttcct   1620

ggagatggtg ttgataaagc aatttagggc cacttacact tctaagcaag tttaatcttt   1680

ggatgcctga attttaaaag ggctagaaaa aaatgattga ccagcctggg aaacataaca   1740

agaccccgtc tctacaaaaa aaatttaaaa ttagccaggc gtggtggctc atgcttgtgg   1800

tcccagctgt tcaggaggat gaggcaggag gatctcttga gcccaggagg tcaaggctat   1860

ggtgagccgt gattgtgcca ctgcatacca gcctaggtga cagaatgaga ccctgtctca   1920

aaaaaaaaaa tgattgaaat taaaattcag ctttagcttc catggcagtc ctcacccccca  1980

cctctctaaa agacacagga ggatgacaca gaaacaccgt aagtgtctgg aaggcaaaaa   2040

gatcttaaga ttcaagagag aggacaagta gttatggcta aggacatgaa attgtcagaa   2100

tggcaggtgg cttcttaaca gccctgtgag aagcagacag atgcaaagaa aatctggaat   2160

ccctttctca ttagcatgaa tgaacctgat acacaattat gaccagaaaa tatggctcca   2220

tgaaggtgct acttttaagt aatgtatgtg cgctctgtaa agtgattaca tttgtttcct   2280

gtttgtttat ttatttattt atttttgcat tctgaggctg aactaataaa aactcttctt   2340

tgtaatc                                                              2347


<210> SEQ ID NO 36
<211> LENGTH: 1202
<212> TYPE: DNA
<213> ORGANISM: Homo sapiens

<400> SEQUENCE: 36

tgtccggcgc cccccgggag ggaactgggt ggccgcaccc tcccggctgc ggtggctgtc     60

gccccccacc ctgcagccag gactcgatgg agaatccatt ccaatatatg gccatgtggc    120
```

-continued

```
tctttggagc aatgttccat catgttccat gctgctgctg acgtcacatg gagcacagaa    180
atcaatgtta gcagatagcc agcccataca agatcgtatt gtattgtagg aggcatcgtg    240
gatggatggc tgctggaaac cccttgccat agccagctct tcttcaatac ttaaggattt    300
accgtggctt tgagtaatga gaatttcgaa accacatttg agaagtattt ccatccagtg    360
ctacttgtgt ttacttctaa acagtcattt tctaactgaa gctggcattc atgtcttcat    420
tttgggctgt ttcagtgcag ggcttcctaa aacagaagcc aactgggtga atgtaataag    480
tgatttgaaa aaaattgaag atcttattca atctatgcat attgatgcta ctttatatac    540
ggaaagtgat gttcacccca gttgcaaagt aacagcaatg aagtgctttc tcttggagtt    600
acaagttatt tcacttgagt ccggagatgc aagtattcat gatacagtag aaaatctgat    660
catcctagca aacaacagtt tgtcttctaa tgggaatgta acagaatctg gatgcaaaga    720
atgtgaggaa ctggaggaaa aaaatattaa agaatttttg cagagttttg tacatattgt    780
ccaaatgttc atcaacactt cttgattgca attgattctt tttaaagtgt ttctgttatt    840
aacaaacatc actctgctgc ttagacataa caaaacactc ggcatttaaa atgtgctgtc    900
aaaacaagtt tttctgtcaa gaagatgatc agaccttgga tcagatgaac tcttagaaat    960
gaaggcagaa aaatgtcatt gagtaatata gtgactatga acttctctca gacttacttt   1020
actcattttt ttaatttatt attgaaattg tacatatttg tggaataatg taaaatgttg   1080
aataaaaata tgtacaagtg ttgtttttta agttgcactg atattttacc tcttattgca   1140
aaatagcatt tgtttaaggg tgatagtcaa attatgtatt ggtggggctg ggtaccaatg   1200
ct                                                                  1202
```

<210> SEQ ID NO 37
<211> LENGTH: 306
<212> TYPE: DNA
<213> ORGANISM: Homo sapiens

<400> SEQUENCE: 37

```
atcgtcaacc tcaaggacga gctgctgttt cccagctggg aggctctgtt ctcaggctct     60
gagggtccgc tgaagcccgg ggcacgcatc ttctcctttg acggcaagga cgtcctgagg    120
caccccaccc ggccccagaa gagcgtgtgg catggctcgg accccaacgg gcgcaggctg    180
accgagagct actgtgagac gtggcggacg gaggctccct cggccacggg ccaggcctcc    240
tcgctgctgg ggggcaggct cctggggcag agtgccgcga gcagccatca cgcctacatc    300
gtgcta                                                               306
```

<210> SEQ ID NO 38
<211> LENGTH: 1062
<212> TYPE: DNA
<213> ORGANISM: Homo sapiens

<400> SEQUENCE: 38

```
tcagagtgca agactgggaa tggaaagaac tacagaggga cgatgtccaa aacaaaaaat     60
ggcatcacct gtcaaaaatg gagttccact tctccccaca gacctagatt ctcacctgct    120
acacacccct cagagggact ggaggagaac tactgcagga atccagacaa cgatccgcag    180
gggccctggt gctatactac tgatccagaa aagagatatg actactgcga cattcttgag    240
tgtgaagagg aatgtatgca ttgcagtgga gaaaactatg acggcaaaat ttccaagacc    300
atgtctggac tggaatgcca ggcctgggac tctcagagcc cacacgctca tggatacatt    360
```

```
ccttccaaat ttccaaacaa gaacctgaag aagaattact gtcgtaaccc cgatagggag    420
ctgcggcctt ggtgtttcac caccgacccc aacaagcgct gggaactttg cgacatcccc    480
cgctgcacaa cacctccacc atcttctggt cccacctacc agtgtctgaa gggaacaggt    540
gaaaactatc gcgggaatgt ggctgttacc gtttccgggc acacctgtca gcactggagt    600
gcacagaccc ctcacacaca taacaggaca ccagaaaact tcccctgcaa aaatttggat    660
gaaaactact gccgcaatcc tgacggaaaa agggccccat ggtgccatac aaccaacagc    720
caagtgcggt gggagtactg taagataccg tcctgtgact cctccccagt atccacggaa    780
caattggctc ccacagcacc acctgagcta acccctgtgg tccaggactg ctaccatggt    840
gatggacaga gctaccgagg cacatcctcc accaccacca caggaaagaa gtgtcagtct    900
tggtcatcta tgacaccaca ccggcaccag aagaccccag aaaactaccc aaatgctggc    960
ctgacaatga actactgcag gaatccagat gccgataaag gcccctggtg ttttaccaca   1020
gaccccagcg tcaggtggga gtactgcaac ctgaaaaaat gc                      1062
```

<210> SEQ ID NO 39
<211> LENGTH: 738
<212> TYPE: DNA
<213> ORGANISM: Homo sapiens

<400> SEQUENCE: 39

```
ccaggtttga aaggaaaacg tggagacagt ggatcacctg caacctggac aacgagaggc     60
tttgtcttca cccgacacag tcaaaccaca gcaattcctt catgtccaga ggggacagtg    120
ccactctaca gtgggttttc ttttcttttt gtacaaggaa atcaacgagc ccacggacaa    180
gaccttggaa ctcttggcag ctgcctgcag cgatttacca caatgccatt cttattctgc    240
aatgtcaatg atgtatgtaa ttttgcatct cgaaatgatt attcatactg gctgtcaaca    300
ccagctctga tgccaatgaa catggctccc attactggca gagcccttga gccttatata    360
agcagatgca ctgtttgtga aggtcctgcg atcgccatag ccgttcacag ccaaaccact    420
gacattcctc catgtcctca cggctggatt tctctctgga aaggattttc attcatcatg    480
ttcacaagtg caggttctga gggcaccggg caagcactgg cctcccctgg ctcctgcctg    540
gaagaattcc gagccagccc atttctagaa tgtcatggaa gaggaacgtg caactactat    600
tcaaattcct acagtttctg gctggcttca ttaaacccag aaagaatgtt cagaaagcct    660
attccatcaa ctgtgaaagc tggggaatta gaaaaaataa taagtcgctg tcaggtgtgc    720
atgaagaaaa gacactga                                                  738
```

<210> SEQ ID NO 40
<211> LENGTH: 2780
<212> TYPE: DNA
<213> ORGANISM: Homo sapiens

<400> SEQUENCE: 40

```
cccgggagcc cagtgcagca gcttccccga tgggtcctgg tcatgcggct tctgccctgt     60
gggcttcttg ggcaatggca cccactgtga ggacctggac gagtgtgccc tggtccccga    120
catctgcttc tccaccagca aggtgcctcg ctgtgtcaac actcagcctg gcttccactg    180
cctgccctgc ccgccccgat acagagggaa ccagcccgtc ggggtcggcc tggaagcagc    240
caagacggaa aagcaagtgt gtgagcccga aaacccatgc aaggacaaga cacacaactg    300
ccacaagcac gcggagtgca tctacctggg tcacttcagc gaccccatgt acaagtgcga    360
gtgccagaca ggctacgcgg gcgacgggct catctgcggg gaggactcgg acctggacgg    420
```

-continued

```
ctggcccaac ctcaatctgg tctgcgccac caacgccacc taccactgca tcaaggataa    480
ctgcccccat ctgccaaatt ctgggcagga agactttgac aaggacggga ttggcgatgc    540
ctgtgatgat gacgatgaca atgacggtgt gaccgatgag aaggacaact gccagctcct    600
cttcaatccc cgccaggctg actatgacaa ggatgaggtt ggggaccgct gtgacaactg    660
cccttacgtg cacaaccctg cccagatcga cacagacaac aatggagagg gtgacgcctg    720
ctccgtggac attgatgggg acgatgtctt caatgaacga gacaattgtc cctacgtcta    780
caacactgac cagagggaca cggatggtga cggtgtgggg gatcactgtg acaactgccc    840
cctggtgcac aaccctgacc agaccgacgt ggacaatgac cttgttgggg accagtgtga    900
caacaacgag gacatagatg acgacggcca ccagaacaac caggacaact gcccctacat    960
ctccaacgcc aaccaggctg accatgacag agacggccag ggcgacgcct gtgaccctga   1020
tgatgacaac gatggcgtcc ccgatgacag ggacaactgc cggcttgtgt tcaacccaga   1080
ccaggaggac ttggacggtg atggacgggg tgatatttgt aaagatgatt ttgacaatga   1140
caacatccca gatattgatg atgtgtgtcc tgaaaacaat gccatcagtg agacagactt   1200
caggaacttc cagatggtcc ccttggatcc caaagggacc acccaaattg atcccaactg   1260
ggtcattcgc catcaaggca aggagctggt tcagacagcc aactcggacc ccggcatcgc   1320
tgtaggtttt gacgagtttg ggtctgtgga cttcagtggc acattctacg taaacactga   1380
ccgggacgac gactatgctg gcttcgtctt tggttaccag tcaagcagcc gcttctatgt   1440
ggtgatgtgg aagcaggtga cgcagaccta ctgggaggac cagcccacgc gggcctatgg   1500
ctactccggc gtgtccctca aggtggtgaa ctccaccacg gggacgggcg agcacctgag   1560
gaacgcgctg tggcacacgg ggaacacgcc ggggcaggtg cgaaccttat ggcacgaccc   1620
caggaacatt ggctggaagg actacacggc ctataggtgg cacctgactc acaggcccaa   1680
gaccggctac atcagagtct tagtgcatga aggaaaacag gtcatggcag actcaggacc   1740
tatctatgac caaacctacg ctggcgggcg gctgggtcta tttgtcttct ctcaagaaat   1800
ggtctatttc tcagacctca agtacgaatg cagagatatt taaacaagat ttgctgcatt   1860
tccggcaatg ccctgtgcat gccatggtcc ctagacacct cagttcattg tggtccttgc   1920
ggcttctctc tctagcagca cctcctgtcc cttgacctta actctgatgg ttcttcacct   1980
cctgccagca accccaaacc caagtgcctt cagaggataa atatcaatgg aactcagaga   2040
tgaacatcta acccactaga ggaaaccagt ttggtgatat atgagacttt atgtggagtg   2100
aaaattgggc atgccattac attgcttttt cttgtttgtt taaaaagaat gacgtttaca   2160
tataaaatgt aattacttat tgtatttatg tgtatatgga gttgaaggga atactgtgca   2220
taagccatta tgataaatta agcatgaaaa atattgctga actacttttg gtgcttaaag   2280
ttgtcactat tcttgaatta gagttgctct acaatgacac acaaatcccg ctaaataaat   2340
tataaacaag ggtcaattca aatttgaagt aatgttttag taaggagaga ttagaagaca   2400
acaggcatag caaatgacat aagctaccga ttaactaatc ggaacatgta aaacagttac   2460
aaaaataaac gaactctcct cttgtcctac aatgaaagcc ctcatgtgca gtagagatgc   2520
agtttcatca aagaacaaac atccttgcaa atgggtgtga cgcggttcca gatgtggatt   2580
tggcaaaacc tcatttaagt aaaaggttag cagagcaaag tgcggtgctt tagctgctgc   2640
ttgtgccgtt gtggcgtcgg ggaggctcct gcctgagctt ccttccccag ctttgctgcc   2700
tgagaggaac cagagcagac gcacaggccg gaaaaggcgc atctaacgcg tatctaggct   2760
```

-continued

```
ttggtaactg cggacaagcc                                                2780

<210> SEQ ID NO 41
<211> LENGTH: 966
<212> TYPE: DNA
<213> ORGANISM: Aequorea victoria

<400> SEQUENCE: 41

tacacacgaa taaaagataa caaagatgag taaaggagaa gaacttttca ctggagttgt      60

cccaattctt gttgaattag atggtgatgt taatgggcac aaattttctg tcagtggaga     120

gggtgaaggt gatgcaacat acggaaaact tacccttaaa tttatttgca ctactggaaa     180

actacctgtt ccatggccaa cacttgtcac tactttctct tatggtgttc aatgcttttc     240

aagataccca gatcatatga aacagcatga ctttttcaag agtgccatgc ccgaaggtta     300

tgtacaggaa agaactatat ttttcaaaga tgacgggaac tacaagacac gtgctgaagt     360

caagtttgaa ggtgataccc ttgttaatag aatcgagtta aaaggtattg attttaaaga     420

agatggaaac attcttggac acaaattgga atacaactat aactcacaca atgtatacat     480

catggcagac aaacaaaaga atggaatcaa agttaacttc aaaattagac acaacattga     540

agatggaagc gttcaactag cagaccatta tcaacaaaat actccaattg gcgatggccc     600

tgtcctttta ccagacaacc attacctgtc cacacaatct gccctttcga aagatcccaa     660

cgaaaagaga gaccacatgg tccttcttga gtttgtaaca gctgctggga ttacacatgg     720

catggatgaa ctatacaaat aaatgtccag acttccaatt gacactaaag tgtccgaaca     780

attactaaaa tctcagggtt cctggttaaa ttcaggctga gatattattt atatatttat     840

agattcatta aaattgtatg aataatttat tgatgttatt gatagaggtt attttcttat     900

taaacaggct acttggagtg tattcttaat tctatattaa ttacaatttg atttgacttg     960

ctcaaa                                                                966

<210> SEQ ID NO 42
<211> LENGTH: 2387
<212> TYPE: DNA
<213> ORGANISM: Photinus pyralis

<400> SEQUENCE: 42

ctgcagaaat aactaggtac taagcccgtt tgtgaaaagt ggccaaaccc ataaatttgg      60

caattacaat aaagaagcta aaattgtggt caaactcaca aacattttta ttatatacat     120

tttagtagct gatgcttata aaagcaatat ttaaatcgta aacaacaaat aaaataaaat     180

ttaaacgatg tgattaagag ccaaaggtcc tctagaaaaa ggtatttaag caacggaatt     240

cctttgtgtt acattcttga atgtcgctcg cagtgacatt agcattccgg tactgttggt     300

aaaatggaag acgccaaaaa cataaagaaa ggcccggcgc cattctatcc tctagaggat     360

ggaaccgctg gagagcaact gcataaggct atgaagagat acgccctggt tcctggaaca     420

attgcttttg tgagtatttc tgtctgattt ctttcgagtt aacgaaatgt tcttatgttt     480

ctttagacag atgcacatat cgaggtgaac atcacgtacg cggaatactt cgaaatgtcc     540

gttcggttgg cagaagctat gaaacgatat gggctgaata caaatcacag aatcgtcgta     600

tgcagtgaaa actctcttca attctttatg ccggtgttgg gcgcgttatt tatcggagtt     660

gcagttgcgc ccgcgaacga catttataat gaacgtaagc accctcgcca tcagaccaaa     720

gggaatgacg tatttaattt ttaaggtgaa ttgctcaaca gtatgaacat ttcgcagcct     780

accgtagtgt ttgtttccaa aaaggggttg caaaaaattt tgaacgtgca aaaaaaatta     840
```

-continued

```
ccaataatcc agaaaattat tatcatggat tctaaaacgg attaccaggg atttcagtcg    900
atgtacacgt tcgtcacatc tcatctacct cccggtttta atgaatacga ttttgtacca    960
gagtcctttg atcgtgacaa aacaattgca ctgataatga attcctctgg atctactggg   1020
ttacctaagg gtgtggccct tccgcataga actgcctgcg tcagattctc gcatgccagg   1080
tatgtcgtat aacaagagat taagtaatgt tgctacacac attgtagaga tcctattttt   1140
ggcaatcaaa tcattccgga tactgcgatt ttaagtgttg ttccattcca tcacggtttt   1200
ggaatgttta ctacactcgg atatttgata tgtggatttc gagtcgtctt aatgtataga   1260
tttgaagaag agctgttttt acgatccctt caggattaca aaattcaaag tgcgttgcta   1320
gtaccaaccc tattttcatt cttcgccaaa agcactctga ttgacaaata cgatttatct   1380
aatttacacg aaattgcttc tgggggcgca cctctttcga aagaagtcgg ggaagcggtt   1440
gcaaaacggt gagttaagcg cattgctagt atttcaaggc tctaaaacgg cgcgtagctt   1500
ccatcttcca gggatacgac aaggatatgg gctcactgag actacatcag ctattctgat   1560
tacacccgag gggatgata aaccgggcgc ggtcggtaaa gttgttccat tttttgaagc   1620
gaaggttgtg gatctggata ccgggaaaac gctgggcgtt aatcagagag gcgaattatg   1680
tgtcagagga cctatgatta tgtccggtta tgtaaacaat ccggaagcga ccaacgcctt   1740
gattgacaag gatggatggc tacattctgg agacatagct tactgggacg aagacgaaca   1800
cttcttcata gttgaccgct tgaagtcttt aattaaatac aaaggatatc aggtaatgaa   1860
gatttttaca tgcacacacg ctacaatacc tgtaggtggc cccgctgaa ttggaatcga   1920
tattgttaca acaccccaac atcttcgacg cgggcgtggc aggtcttccc gacgatgacg   1980
ccggtgaact tcccgccgcc gttgttgttt tggagcacgg aaagacgatg acggaaaaag   2040
agatcgtgga ttacgtcgcc agtaaatgaa ttcgttttac gttactcgta ctacaattct   2100
tttcataggt caagtaacaa ccgcgaaaaa gttgcgcgga ggagttgtgt ttgtggacga   2160
agtaccgaaa ggtcttaccg gaaaactcga cgcaagaaaa atcagagaga tcctcataaa   2220
ggccaagaag ggcggaaagt ccaaattgta aaatgtaact gtattcagcg atgacgaaat   2280
tcttagctat tgtaatatta tatgcaaatt gatgaatggt aattttgtaa ttgtgggtca   2340
ctgtactatt ttaacgaata ataaaatcag gtataggtaa ctaaaaa                 2387
```